(12) United States Patent
Nakagawa et al.

(10) Patent No.: US 10,563,199 B2
(45) Date of Patent: Feb. 18, 2020

(54) ANTISENSE NUCLEIC ACID FOR TREATING AMYOTROPHY

(71) Applicants: NIPPON SHINYAKU CO., LTD., Kyoto-shi, Kyoto (JP); Kawasaki Gakuen Educational Foundation, Kurashiki-shi, Okayama (JP)

(72) Inventors: Shinichiro Nakagawa, Ibaraki (JP); Seigo Nagata, Kyoto (JP); Yoshihide Sunada, Okayama (JP); Yutaka Ohsawa, Okayama (JP); Shin-ichiro Nishimatsu, Okayama (JP)

(73) Assignees: NIPPON SHINYAKU CO., LTD., Kyoto-shi, Kyoto (JP); KAWASAKI GAKUEN EDUCATIONAL FOUNDATION, Kurashiki-shi, Okaayama (JP)

( * ) Notice: Subject to any disclaimer, the term of this patent is extended or adjusted under 35 U.S.C. 154(b) by 0 days.

(21) Appl. No.: 15/759,305

(22) PCT Filed: Sep. 16, 2016

(86) PCT No.: PCT/JP2016/077416
§ 371 (c)(1),
(2) Date: Mar. 12, 2018

(87) PCT Pub. No.: WO2017/047741
PCT Pub. Date: Mar. 23, 2017

(65) Prior Publication Data
US 2018/0251760 A1 Sep. 6, 2018

(30) Foreign Application Priority Data
Sep. 16, 2015 (JP) .................................. 2015-182614

(51) Int. Cl.
*C12N 15/113* (2010.01)

(52) U.S. Cl.
CPC ........ *C12N 15/113* (2013.01); *C12N 2310/11* (2013.01); *C12N 2310/31* (2013.01); *C12N 2310/3233* (2013.01)

(58) Field of Classification Search
CPC .............. C12N 15/113; C12N 2310/11; C12N 2310/31; C12N 2310/32; C12N 2310/33; A01K 2207/05
See application file for complete search history.

(56) References Cited

U.S. PATENT DOCUMENTS

| 7,888,012 B2 * | 2/2011 | Iversen | C07H 21/00 |
| | | | 435/6.16 |
| 2009/0311788 A1 * | 12/2009 | Pachuk | C12N 15/79 |
| | | | 435/455 |
| 2013/0085139 A1 * | 4/2013 | Dickson | C07H 21/04 |
| | | | 514/232.5 |
| 2017/0204410 A1 * | 7/2017 | Watanabe | A61K 48/00 |
| 2018/0355358 A1 * | 12/2018 | Schnell | C12N 15/1136 |

FOREIGN PATENT DOCUMENTS

| JP | 2007-104971 A | 4/2007 | |
| WO | WO-91/09033 A1 | 6/1991 | |
| WO | WO-2006/000057 A1 | 1/2006 | |
| WO | WO-2006/086667 A2 | 8/2006 | |
| WO | WO-2009/064471 A1 | 5/2009 | |
| WO | WO-2012/029986 A1 | 3/2012 | |
| WO | WO-2013040429 A1 * | 3/2013 | ........... C12N 15/113 |
| WO | WO-2015/194520 A1 | 12/2015 | |

OTHER PUBLICATIONS

Gonzalez-Cadavid et al. PNAS 95, 14938-14943 (Year: 1998).*
O'Donovan et al. Nucleic Acid Therapeutics vol. 0 pp. 1-10 (Year: 2014).*
Sazani et al. International Journal of Toxicology 30, 313-321 (Year: 2011).*
Amantana et al. Current Opinion in Pharamacology 5: 550-555 (Year: 2005).*
Alul, Rushdi H., et al., "Oxalyl-CPG: a labile support for synthesis of sensitive oligonucleotide derivatives," Nucleic Acids Research, vol. 19, No. 7, 1991, pp. 1527-1532.
Aoki, Yoshitsugu, et al., "Feasibility and Effectiveness of Exon 51 skipping in Human-Like mdx Mutation," Molecular Therapy, vol. 18, Supplement 1, May 2010, pp. S218-S219.
Bestas, Burcu, et al., "Design and Application of Bispecific Splice-Switching Oligonucleiotides," Nucleic Acid Therapeutics, vol. 24, No. 1, 2014, pp. 13-24.
Christensen, Leif, et al., "Solid-phase Synthesis of Peptide Nucleic Acids," Journal of Peptide Science, vol. 3, 1995, pp. 175-183.
Dueholm, Kim L., et al., "Sysnthesis of Peptide Nucleic Acid Monomers Containing the Four Natural Nucleobases: Thymine, Cytosine, Adenine, and Guanine and Their Oligomerization," J. Org. Chem. 59, 1994, pp. 5767-5773.
Egholm, Michael, et al., "Peptide Nucleic Acids (PNA). Oligonucleotide Analogues with an Achiral Peptide Backbone," J. Am. Chem. Soc. 114, 1992, pp. 1895-1897.
Janson, J.A.M, et al., "G.P.87 Prospects for single antisense oligonucleotide-induces multiple exon skipping for rare non-hotspot mutations in Duchenne muscular dystrophy," Neuromusclar Disorders, 24, 2014, pp. 820-821.
Kang, Jagjeet K., et al., "Antisense-induced Myostatin Exon Skipping Leads to Muscle Hypertrophy in Mice Following Octaguanidine Morpholino Oligomer Treatment," Molecular Therapy, vol. 19, No. 1, Jan. 2011, pp. 159-164.
Karlin, Samuel, et al., "Methods for assessing the statistical significance of molecular sequence features by using general scoring schemes," Proc. Natl. Acad. Sci., vol. 87, Mar. 1990, pp. 2264-2268.

(Continued)

*Primary Examiner* — Brian Whiteman
(74) *Attorney, Agent, or Firm* — Drinker Biddle & Reath LLP

(57) ABSTRACT

There has been a demand for a novel antisense nucleic acid or the like capable of inhibiting myostatin at the mRNA level. The present invention provides a specific antisense oligomer which allows exon 2 skipping in the myostatin gene or induces degradation of mRNA of the myostatin gene.

12 Claims, 5 Drawing Sheets

Specification includes a Sequence Listing.

(56) References Cited

OTHER PUBLICATIONS

Karling, Samuel, et al., "Applications and statistics for multiple high-scoring segments in moluecular sequences," Proc. Natl. Acad. Sci., vol. 90, Jun. 1993, pp. 5873-5877.

Kemaladewi, Dwi U., et al., "Dual exon skipping in myostatin and dystrophin for Duchenne muscular dystrophy," BMC Medical Genomics, 4:36, 2011, 10 pages.

Koch, Troels, et al., "Improvements in automated PNA synthesis using Boc/Z monomers," J. Peptide Res. 49, 1997, pp. 80-88.

Lu-Nguyen, Ngoc B, et al., "Combination Antisense Treatment for Destructive Exon Skipping of Myostatin and Open Reading Frame Rescue of Dystrophin in Neonatal mdx Mice," Molecular Therapy, vol. 23, No. 8, Aug. 2015, pp. 1341-1348.

Malerba, Alberto, et al., "Dual Myostatin and Dystrophin Exon Skipping by Morpholino Nucleic Acid Oligomers Conjugated to a Cell-penetrating Peptide Is a Promising Therapeutic Strategy for the Treatment of Duchenne Muscular Dystrophy," Molecular Therapy-Nucleic Acids (2012) 1, e62, 8 pages.

Nielsen, Peter E., et al., "Sequence-Selective Recognition of DNA by Strand Displacement with a Thymine-Substituted Polyamide," Science, vol. 254, 1991, pp. 1497-1500.

Pao, Peng Wen, et al., "Dual Masking of Specific Negative Splicing Regulatory Elements Resulted in Mximal Exon 7 Including of SMN2 Gene," Molecular Therapy, The American Society of Gene & Cell Therapy, vol. 22, No. 4, Apr. 2014, pp. 854-861.

Wright, Peter, et al., "Large Scale Sysnthesis of Oligonucleotides via Phosphoramidite Nucleisides and a High-loaded Polystyrene Support," Tetrahedron Letters, vol. 34, No. 21, 1993, pp. 3373-3376.

Database GenBank, Accession No. NM_005259.2, "*Homo sapiens* myostatin (MSTN), mRNA" Mar. 15, 2015, [online] https://www.ncbi.nlm.nih.gov/nuccore/149408158?sat=21&satkey=48990432, Mar. 15, 2015, 4 pages.

International Search Report dated Oct. 18, 2016 for PCT/JP2016/077416.

Writtein Opinion dated Oct. 18, 2016 for PCT/JP2016/077416.

Extended European search report dated Apr. 5, 2019 issued in European patent application No. EP16846612.6.

Database GenBank, Accession No. NM_010834.3, "Mus musculus myostatin (Mstn), mRNA", Mar. 12, 2019, 6 pages.

Aartsma-Rus, A., et al., "Antisense-Induced Multiexon Skipping for Duchenne Muscular Dystrophy Makes More Sense," American Journal of Human Gene, American Society of Human Genetics, Chicago, IL, US, vol. 74, No. 1, Jan. 1, 2004, pp. 83-92.

\* cited by examiner

ANTISENSE NUCLEIC ACID FOR TREATING AMYOTROPHY

CROSS REFERENCES TO RELATED APPLICATIONS

This application is the National Stage of International Application No. PCT/JP2016/077416, filed Sep. 16, 2016, and claims benefit of Japanese Application No. 2015-182614, filed on Sep. 16, 2015.

REFERENCE TO A SEQUENCE LISTING

The instant application contains a sequence listing which has been submitted in ASCII format via EFS-Web and is hereby incorporated by reference in its entirety. Said ASCII copy, created on Sep. 16, 2016, is named P245070_Seq_List.txt and is 71,669 bytes in size.

TECHNICAL FIELD

The present invention relates to an antisense oligomer which allows exon 2 skipping in the myostatin gene, and a pharmaceutical composition comprising such an oligomer.

BACKGROUND ART

Myostatin (also known as GDF-8) was discovered in 1997 as a novel cytokine belonging to the TGF-β superfamily. Its expression is specific to skeletal muscle which is a primary tissue responsible for movement and metabolism. Myostatin-deficient mutant animals show significant muscle hypertrophy where skeletal muscle mass is increased twice as much as in wild-type animals, so that myostatin is considered to be a negative control factor for skeletal muscle mass.

Based on the above findings, a therapeutic strategy can be designed to treat amyotrophic diseases or muscle wasting diseases through inhibition of myostatin. Skeletal muscle atrophy will induce not only limitation of daily living activities due to muscle weakness, but also serious systemic complications such as undernutrition and respiratory failure. Target diseases of this therapeutic strategy may include myogenic amyotrophy (e.g., muscular dystrophy, congenital myopathy, inclusion body myositis), neurogenic amyotrophy (e.g., amyotrophic lateral sclerosis, spinal muscular atrophy, spinal and bulbar muscular atrophy), disuse amyotrophy (e.g., apoplexy-induced disuse syndrome), muscle wasting diseases (e.g., cancer cachexia, sepsis-related amyotrophy), various types of sarcopenia including age-related skeletal muscle loss (age-related sarcopenia), etc.

The human myostatin gene is located on the long arm of chromosome 2. From three exons constituting this gene, mature mRNA having a chain length of approximately 2.8 kilobases is transcribed and further translated into a precursor polypeptide consisting of 375 amino acid residues. Myostatin precursor polypeptide molecules form a dimer through disulfide bonding between their C-terminal domains, and then cleaved between amino acid residues at positions 266 and 267 (R-D) in endoplasmic reticulum by the actin of a protease of the Furin family, so that the precursor dimer is divided into an N-terminal propeptide and a C-terminal domain dimer which will function later as active myostatin. These peptides are associated through non-covalent bonding and secreted as an inactive complex into the extracellular environment. This complex is further dissociated when the N-terminal propeptide is cleaved off between amino acid residues at positions 98 and 99 (R-D) by the action of a matrix metalloprotease of the BMP1/Tolloid family, whereby an active myostatin dimer appears.

In recent years, attention has been focused on antisense nucleic acid drugs, which are designed and chemically synthesized as short antisense artificial nucleic acids binding complementarily to a part of precursor mRNA in an attempt to inhibit mRNA function. In the normal mechanism of gene transcription, introns in precursor mRNA are cleaved and removed by the action of an enzyme complex called spliceosome to thereby generate mature mRNA. An antisense nucleic acid for exon skipping is designed to modify this spliceosome-mediated splicing regulatory mechanism and induce the generation of mRNA different from normal mature mRNA, thereby inhibiting the function of the gene. Moreover, mRNA is associated not only with the spliceosome, but also with an mRNA-stabilizing protein or an expression/translation regulatory factor (including miRNA) for regulation of mRNA degradation, expression and translation. An antisense nucleic acid is also considered to inhibit the association of such an mRNA-binding protein to its target mRNA, thereby inhibiting the function of the gene.

Currently, some antisense nucleic acids have been known to cause exon skipping in myostatin (Patent Documents 1 to 3 and Non-patent Documents 1 to 4).

PRIOR ART DOCUMENTS

Patent Documents

Patent Document 1: US2013/0085139A1
Patent Document 2: WO2006/086667A2
Patent Document 3: JP2007-104971A

Non-Patent Documents

Non-patent Document 1: Kang J K et al., Mol. Ther. (2011) 19(1):159-164
Non-patent Document 2: Kemaladewi et al., BMC Med Genomics. (2011) 4:36
Non-patent Document 3: Alberto Malerba et al., Mol. Ther. Nucleic Acids. (2012) 1:e62
Non-patent Document 4: Bestas B et al., Nucleic Acid Ther. (2014) 24(1):13-24

SUMMARY OF THE INVENTION

Problem to be Solved by the Invention

Under such circumstances as described above, there has been a demand for a novel antisense nucleic acid capable of inhibiting myostatin at the mRNA level.

Means to Solve the Problem

As a result of repeating extensive and intensive efforts to solve the problem stated above, the inventors of the present invention have found that myostatin can be efficiently inhibited at the mRNA level when a particular function inhibitory antisense nucleic acid is applied to the myostatin gene. This finding led to the completion of the present invention.

Namely, the present invention is as follows.

[1]
An antisense oligomer of 14 to 30 bases in length comprising the following unit oligomers connected together:
(a) a first unit oligomer comprising a nucleotide sequence complementary to a first nucleotide sequence consisting of contiguous 7 to 15 bases in exon 2 of the human or mouse myostatin gene; and (b) a second unit oligomer comprising a nucleotide sequence complementary to a second nucleotide sequence consisting of contiguous 7 to 15 bases in said exon 2, wherein the first nucleotide sequence and the second nucleotide sequence are not contiguous to each other or do not overlap with each other, or a pharmaceutically acceptable salt or hydrate thereof.

[2]

The antisense oligomer or pharmaceutically acceptable salt or hydrate thereof according to [1] above, wherein the antisense oligomer is (c) or (d) shown below:

(c) an antisense oligomer of 14 to 30 bases in length comprising connected two unit oligomers selected from the group consisting of unit oligomers (c-1) to (c-6) shown below:

(c-1) a unit oligomer consisting of a nucleotide sequence complementary to a nucleotide sequence consisting of contiguous 7 to 15 bases selected from a nucleotide sequence located at positions −10 to 45 from the 5'-terminal end of exon 2 in the human myostatin gene;

(c-2) a unit oligomer consisting of a nucleotide sequence complementary to a nucleotide sequence consisting of contiguous 7 to 15 bases selected from a nucleotide sequence located at positions 91 to 135 from the 5'-terminal end of exon 2 in the human myostatin gene;

(c-3) a unit oligomer consisting of a nucleotide sequence complementary to a nucleotide sequence consisting of contiguous 7 to 15 bases selected from a nucleotide sequence located at positions 121 to 155 from the 5'-terminal end of exon 2 in the human myostatin gene;

(c-4) a unit oligomer consisting of a nucleotide sequence complementary to a nucleotide sequence consisting of contiguous 7 to 15 bases selected from a nucleotide sequence located at positions 166 to 210 from the 5'-terminal end of exon 2 in the human myostatin gene;

(c-5) a unit oligomer consisting of a nucleotide sequence complementary to a nucleotide sequence consisting of contiguous 7 to 15 bases selected from a nucleotide sequence located at positions 204 to 233 from the 5'-terminal end of exon 2 in the human myostatin gene; and (c-6) a unit oligomer consisting of a nucleotide sequence complementary to a nucleotide sequence consisting of contiguous 7 to 15 bases selected from a nucleotide sequence located at positions 326 to 374 from the 5'-terminal end of exon 2 in the human myostatin gene; or (d) an antisense oligomer of 14 to 30 bases in length comprising connected two unit oligomers selected from the group consisting of unit oligomers (d-1) to (d-7) shown below:

(d-1) a unit oligomer consisting of a nucleotide sequence complementary to a nucleotide sequence consisting of contiguous 7 to 15 bases selected from a nucleotide sequence located at positions −10 to 65 from the 5'-terminal end of exon 2 in the mouse myostatin gene;

(d-2) a unit oligomer consisting of a nucleotide sequence complementary to a nucleotide sequence consisting of contiguous 7 to 15 bases selected from a nucleotide sequence located at positions 91 to 135 from the 5'-terminal end of exon 2 in the mouse myostatin gene;

(d-3) a unit oligomer consisting of a nucleotide sequence complementary to a nucleotide sequence consisting of contiguous 7 to 15 bases selected from a nucleotide sequence located at positions 121 to 155 from the 5'-terminal end of exon 2 in the mouse myostatin gene;

(d-4) a unit oligomer consisting of a nucleotide sequence complementary to a nucleotide sequence consisting of contiguous 7 to 15 bases selected from a nucleotide sequence located at positions 151 to 210 from the 5'-terminal end of exon 2 in the mouse myostatin gene;

(d-5) a unit oligomer consisting of a nucleotide sequence complementary to a nucleotide sequence consisting of contiguous 7 to 15 bases selected from a nucleotide sequence located at positions 196 to 233 from the 5'-terminal end of exon 2 in the mouse myostatin gene;

(d-6) a unit oligomer consisting of a nucleotide sequence complementary to a nucleotide sequence consisting of contiguous 7 to 15 bases selected from a nucleotide sequence located at positions 266 to 295 from the 5'-terminal end of exon 2 in the mouse myostatin gene; and (d-7) a unit oligomer consisting of a nucleotide sequence complementary to a nucleotide sequence consisting of contiguous 7 to 15 bases selected from a nucleotide sequence located at positions 326 to 374 from the 5'-terminal end of exon 2 in the mouse myostatin gene.

[3]

The antisense oligomer or pharmaceutically acceptable salt or hydrate thereof according to [1] above, wherein the antisense oligomer is (e) or (f) shown below:

(e) an antisense oligomer of 14 to 30 bases in length comprising connected two unit oligomers selected from the group consisting of unit oligomers (e-1) to (e-6) shown below:

(e-1) a unit oligomer consisting of a nucleotide sequence complementary to a nucleotide sequence consisting of contiguous 7 to 15 bases selected from a nucleotide sequence located at positions −4 to 25 from the 5'-terminal end of exon 2 in the human myostatin gene;

(e-2) a unit oligomer consisting of a nucleotide sequence complementary to a nucleotide sequence consisting of contiguous 7 to 15 bases selected from a nucleotide sequence located at positions 112 to 131 from the 5'-terminal end of exon 2 in the human myostatin gene;

(e-3) a unit oligomer consisting of a nucleotide sequence complementary to a nucleotide sequence consisting of contiguous 7 to 15 bases selected from a nucleotide sequence located at positions 128 to 142 from the 5'-terminal end of exon 2 in the human myostatin gene;

(e-4) a unit oligomer consisting of a nucleotide sequence complementary to a nucleotide sequence consisting of contiguous 7 to 15 bases selected from a nucleotide sequence located at positions 169 to 206 from the 5'-terminal end of exon 2 in the human myostatin gene;

(e-5) a unit oligomer consisting of a nucleotide sequence complementary to a nucleotide sequence consisting of contiguous 7 to 15 bases selected from a nucleotide sequence located at positions 209 to 228 from the 5'-terminal end of exon 2 in the human myostatin gene; and (e-6) a unit oligomer consisting of a nucleotide sequence complementary to a nucleotide sequence consisting of contiguous 7 to 15 bases selected from a nucleotide sequence located at positions 331 to 365 from the 5'-terminal end of exon 2 in the human myostatin gene; or (f) an antisense oligomer of 14 to 30 bases in length comprising connected two unit oligomers selected from the group consisting of unit oligomers (f-1) to (f-7) shown below:

(f-1) a unit oligomer consisting of a nucleotide sequence complementary to a nucleotide sequence consisting of contiguous 7 to 15 bases selected from a nucleotide sequence located at positions 1 to 18 from the 5'-terminal end of exon 2 in the mouse myostatin gene;

(f-2) a unit oligomer consisting of a nucleotide sequence complementary to a nucleotide sequence consisting of contiguous 7 to 15 bases selected from a nucleotide sequence located at positions 116 to 131 from the 5'-terminal end of exon 2 in the mouse myostatin gene;

(f-3) a unit oligomer consisting of a nucleotide sequence complementary to a nucleotide sequence consisting of contiguous 7 to 15 bases selected from a nucleotide sequence located at positions 130 to 140 from the 5'-terminal end of exon 2 in the mouse myostatin gene;

(f-4) a unit oligomer consisting of a nucleotide sequence complementary to a nucleotide sequence consisting of contiguous 7 to 15 bases selected from a nucleotide sequence located at positions 160 to 206 from the 5'-terminal end of exon 2 in the mouse myostatin gene;

(f-5) a unit oligomer consisting of a nucleotide sequence complementary to a nucleotide sequence consisting of contiguous 7 to 15 bases selected from a nucleotide sequence located at positions 211 to 225 from the 5'-terminal end of exon 2 in the mouse myostatin gene;

(f-6) a unit oligomer consisting of a nucleotide sequence complementary to a nucleotide sequence consisting of contiguous 7 to 15 bases selected from a nucleotide sequence located at positions 271 to 282 from the 5'-terminal end of exon 2 in the mouse myostatin gene; and (f-7) a unit oligomer consisting of a nucleotide sequence complementary to a nucleotide sequence consisting of contiguous 7 to 15 bases selected from a nucleotide sequence located at positions 341 to 365 from the 5'-terminal end of exon 2 in the mouse myostatin gene.

[4]

The antisense oligomer or pharmaceutically acceptable salt or hydrate thereof according to [2] above, wherein the antisense oligomer (c) consists of any one nucleotide sequence selected from the group consisting of SEQ ID NO: 103 (NMS-48), SEQ ID NO: 116 (NMS-89), SEQ ID NO: 117 (NMS-90), SEQ ID NO: 120 (NMS-93), SEQ ID NO: 128 (NMS-101), SEQ ID NO: 131 (NMS-104), SEQ ID NO: 136 (NMS-113), SEQ ID NO: 137 (NMS-117), SEQ ID NO: 140 (NMS-123), SEQ ID NO: 145 (NMS-136), SEQ ID NO: 146 (NMS-139), SEQ ID NO: 147 (NMS-140), SEQ ID NO: 148 (NMS-141), SEQ ID NO: 149 (NMS-142), SEQ ID NO: 152 (NMS-145), SEQ ID NO: 155 (NMS-148), SEQ ID NO: 156 (NMS-149), SEQ ID NO: 157 (NMS-150), SEQ ID NO: 159 (NMS-152), SEQ ID NO: 162 (NMS-156), SEQ ID NO: 163 (NMS-157), SEQ ID NO: 165 (NMS-162), SEQ ID NO: 166 (NMS-163), SEQ ID NO: 167 (NMS-164), SEQ ID NO: 168 (NMS-166), SEQ ID NO: 169 (NMS-167), SEQ ID NO: 170 (NMS-168), SEQ ID NO: 171 (NMS-169), SEQ ID NO: 176 (NMS-174), SEQ ID NO: 177 (NMS-175), SEQ ID NO: 178 (NMS-176), SEQ ID NO: 179 (NMS-177), SEQ ID NO: 180 (NMS-178), SEQ ID NO: 183 (NMS-181), SEQ ID NO: 187 (NMS-185), SEQ ID NO: 189 (NMS-188), SEQ ID NO: 190 (NMS-189), SEQ ID NO: 191 (NMS-190), SEQ ID NO: 192 (NMS-191), SEQ ID NO: 193 (NMS-192), SEQ ID NO: 196 (NMS-195), SEQ ID NO: 199 (NMS-198), SEQ ID NO: 200 (NMS-199), SEQ ID NO: 201 (NMS-200), SEQ ID NO: 203 (NMS-202), SEQ ID NO: 204 (NMS-203), SEQ ID NO: 206 (NMS-206), SEQ ID NO: 208 (NMS-208), SEQ ID NO: 212 (NMS-212), SEQ ID NO: 213 (NMS-213), SEQ ID NO: 214 (NMS-214), SEQ ID NO: 215 (NMS-215), SEQ ID NO: 217 (NMS-217), SEQ ID NO: 225 (NMS-225), SEQ ID NO: 226 (NMS-228), SEQ ID NO: 228 (NMS-230), SEQ ID NO: 229 (NMS-231), SEQ ID NO: 231 (NMS-233), SEQ ID NO: 232 (NMS-234), SEQ ID NO: 233 (NMS-235), SEQ ID NO: 236 (NMS-240), SEQ ID NO: 237 (NMS-241), SEQ ID NO: 240 (NMS-244), SEQ ID NO: 243 (NMS-247), SEQ ID NO: 244 (NMS-248), SEQ ID NO: 245 (NMS-249), SEQ ID NO: 246 (NMS-250), SEQ ID NO: 247 (NMS-251), SEQ ID NO: 248 (NMS-252), SEQ ID NO: 252 (NMS-256), SEQ ID NO: 261 (NMS-272), SEQ ID NO: 273 (NMS-284), SEQ ID NO: 274 (NMS-285), SEQ ID NO: 275 (NMS-286) and SEQ ID NO: 277 (NMS-297).

[5]

The antisense oligomer or pharmaceutically acceptable salt or hydrate thereof according to [2] above, wherein the antisense oligomer (d) consists of any one nucleotide sequence selected from the group consisting of SEQ ID NO: 95 (NMS-38), SEQ ID NO: 96 (NMS-39), SEQ ID NO: 107 (NMS-66), SEQ ID NO: 223 (NMS-223), SEQ ID NO: 234 (NMS-238), SEQ ID NO: 235 (NMS-239), SEQ ID NO: 242 (NMS-246), SEQ ID NO: 249 (NMS-253), SEQ ID NO: 250 (NMS-254), SEQ ID NO: 251 (NMS-255), SEQ ID NO: 257 (NMS-268), SEQ ID NO: (NMS-280), SEQ ID NO: (NMS-281), SEQ ID NO: (NMS-282), SEQ ID NO: (NMS-288), SEQ ID NO: (NMS-289), SEQ ID NO: (NMS-290), SEQ ID NO: (NMS-292), SEQ ID NO: (NMS-293), SEQ ID NO: (NMS-294), SEQ ID NO: (NMS-295), SEQ ID NO: (NMS-298), SEQ ID NO: (NMS-299), SEQ ID NO: (NMS-300), SEQ ID NO: (NMS-302) and SEQ ID NO: (NMS-303).

[6]

The antisense oligomer or pharmaceutically acceptable salt or hydrate thereof according to any one of [1] to [5] above, wherein the antisense oligomer is an oligonucleotide.

[7]

The antisense oligomer or pharmaceutically acceptable salt or hydrate thereof according to [6] above, wherein at least one sugar moiety and/or at least one phosphate bond moiety in nucleotides constituting the oligonucleotide is modified.

[8]

The antisense oligomer or pharmaceutically acceptable salt or hydrate thereof according to [7] above, wherein the at least one sugar moiety in nucleotides constituting the oligonucleotide is a ribose in which the —OH group at the 2'-position is substituted with any group selected from the group consisting of OR, R, R'OR, SH, SR, $NH_2$, NHR, $NR_2$, $N_3$, CN, F, Cl, Br and I (wherein R represents alkyl or aryl, and R' represents alkylene).

[9]

The antisense oligomer or pharmaceutically acceptable salt or hydrate thereof according to [7] or [8] above, wherein the at least one phosphate bond moiety in nucleotides constituting the oligonucleotide is any one selected from the group consisting of a phosphorothioate bond, a phosphorodithioate bond, an alkylphosphonate bond, a phosphoroamidate bond and a boranophosphate bond.

[10]

The antisense oligomer or pharmaceutically acceptable salt or hydrate thereof according to any one of [1] to [5] above, wherein the antisense oligomer is a morpholino oligomer.

[11]

The antisense oligomer or pharmaceutically acceptable salt or hydrate thereof according to [10] above, wherein the morpholino oligomer is a phosphorodiamidate morpholino oligomer.

[12]

The antisense oligomer or pharmaceutically acceptable salt or hydrate thereof according to [10] or [11] above, whose 5'-terminal end is any one of the groups represented by chemical formulae (1) to (3) shown below.

[Formula 1]

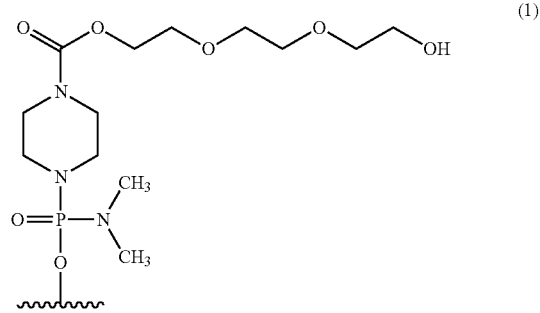

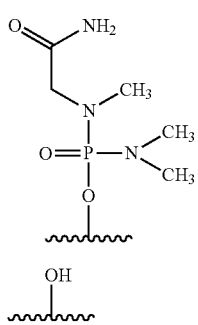

(2)

(3)

[13]
The antisense oligomer or pharmaceutically acceptable salt or hydrate thereof according to any one of [4] and [6] to [12] above, wherein the antisense oligomer consists of any one nucleotide sequence selected from the group consisting of SEQ ID NO: 171 (NMS-169), SEQ ID NO: 192 (NMS-191), SEQ ID NO: 245 (NMS-249) and SEQ ID NO: 231 (NMS-233).

[14]
A pharmaceutical composition comprising the antisense oligomer or pharmaceutically acceptable salt or hydrate thereof according to any one of [3] to [13] above.

[15]
The pharmaceutical composition according to [14] above, which further comprises a pharmaceutically acceptable carrier.

[16]
The pharmaceutical composition according to [14] or [15] above for use in the treatment of an amyotrophic disease or a muscle wasting disease.

[17]
The pharmaceutical composition according to [16] above for use in the treatment of muscular dystrophy.

[18]
A method for prevention or treatment of an amyotrophic disease or a muscle wasting disease, which comprises administering a subject in need of prevention or treatment of an amyotrophic disease or a muscle wasting disease with a therapeutically effective amount of the antisense oligomer or pharmaceutically acceptable salt or hydrate thereof according to any one of [1] to [13] above.

[19]
The method according to [18] above, wherein the amyotrophic disease or muscle wasting disease is muscular dystrophy.

[20]
The method according to [18] or [19] above, wherein the subject is a human subject.

[21]
Use of the antisense oligomer or pharmaceutically acceptable salt or hydrate thereof according to any one of [1] to [13] above in the manufacture of a pharmaceutical composition for treatment of an amyotrophic disease or a muscle wasting disease.

[22]
The antisense oligomer or pharmaceutically acceptable salt or hydrate thereof according to any one of [1] to [13] above for use in the treatment of an amyotrophic disease or a muscle wasting disease.

[23]
Any one antisense oligomer selected from the group consisting of (A) to (H) shown below or a pharmaceutically acceptable salt or hydrate thereof:
(A) an antisense oligomer consisting of a nucleotide sequence complementary to a nucleotide sequence of contiguous 14 to 30 bases in length selected from a nucleotide sequence located at positions −10 to 45 from the 5'-terminal end of exon 2 in the human myostatin gene;
(B) an antisense oligomer consisting of a nucleotide sequence complementary to a nucleotide sequence of contiguous 14 to 30 bases in length selected from a nucleotide sequence located at positions 91 to 145 from the 5'-terminal end of exon 2 in the human myostatin gene;
(C) an antisense oligomer consisting of a nucleotide sequence complementary to a nucleotide sequence of contiguous 14 to 30 bases in length selected from a nucleotide sequence located at positions 146 to 180 from the 5'-terminal end of exon 2 in the human myostatin gene;
(D) an antisense oligomer consisting of a nucleotide sequence complementary to a nucleotide sequence of contiguous 14 to 30 bases in length selected from a nucleotide sequence located at positions 331 to 374 from the 5'-terminal end of exon 2 in the human myostatin gene;
(E) an antisense oligomer consisting of a nucleotide sequence complementary to a nucleotide sequence of contiguous 14 to 30 bases in length selected from a nucleotide sequence located at positions −10 to 31 from the 5'-terminal end of exon 2 in the mouse myostatin gene;
(F) an antisense oligomer consisting of a nucleotide sequence complementary to a nucleotide sequence of contiguous 14 to 30 bases in length selected from a nucleotide sequence located at positions 111 to 162 from the 5'-terminal end of exon 2 in the mouse myostatin gene;
(G) an antisense oligomer consisting of a nucleotide sequence complementary to a nucleotide sequence of contiguous 14 to 30 bases in length selected from a nucleotide sequence located at positions 166 to 195 from the 5'-terminal end of exon 2 in the mouse myostatin gene; and
(H) an antisense oligomer consisting of a nucleotide sequence complementary to a nucleotide sequence of contiguous 14 to 30 bases in length selected from a nucleotide sequence located at positions 331 to 374 from the 5'-terminal end of exon 2 in the mouse myostatin gene.

[24]
Any one antisense oligomer selected from the group consisting of (I) to (L) shown below or a pharmaceutically acceptable salt or hydrate thereof:
(I) an antisense oligomer consisting of a nucleotide sequence complementary to a nucleotide sequence of contiguous 14 to 30 bases in length selected from a nucleotide sequence located at positions −10 to 31 from the 5'-terminal end of exon 2 in the human myostatin gene;
(J) an antisense oligomer consisting of a nucleotide sequence complementary to a nucleotide sequence of contiguous 14 to 30 bases in length selected from a nucleotide sequence located at positions 111 to 140 from the 5'-terminal end of exon 2 in the human myostatin gene, wherein the 3'-terminal base of the nucleotide sequence of 14 to 30 bases in length is a base located at position 140 from the 5'-terminal end of said exon 2; (K) an antisense oligomer consisting of a nucleotide sequence complementary to a nucleotide sequence of contiguous 14 to 30 bases in length selected from a nucleotide sequence located at positions 146 to 180 from the 5'-terminal end of exon 2 in the human myostatin gene; and (L) an antisense oligomer consisting of a nucleotide sequence complementary to a nucleotide sequence of contiguous 14 to 30 bases in length selected from a nucleotide sequence located at positions 331 to 374 from the 5'-terminal end of exon 2 in the human myostatin gene.

[25]

The antisense oligomer or pharmaceutically acceptable salt or hydrate thereof according to [23] above, wherein the antisense oligomer (A) consists of any one nucleotide sequence selected from the group consisting of SEQ ID NO: 13 (NMS-17), SEQ ID NO: 76 (NMS-138), SEQ ID NO: 68 (NMS-120), SEQ ID NO: 75 (NMS-137), SEQ ID NO: 51 (NMS-76), SEQ ID NO: 52 (NMS-79), SEQ ID NO: 54 (NMS-81), SEQ ID NO: 55 (NMS-82), SEQ ID NO: 56 (NMS-83), SEQ ID NO: 53 (NMS-80), SEQ ID NO: 33 (NMS-49), SEQ ID NO: 63 (NMS-114), SEQ ID NO: 69 (NMS-124), SEQ ID NO: 70 (NMS-125), SEQ ID NO: 61 (NMS-110), SEQ ID NO: 31 (NMS-46), SEQ ID NO: 34 (NMS-50), SEQ ID NO: 50 (NMS-75), SEQ ID NO: 45 (NMS-67) and SEQ ID NO: 64 (NMS-115).

[26]

The antisense oligomer or pharmaceutically acceptable salt or hydrate thereof according to [23] above, wherein the antisense oligomer (B) consists of any one nucleotide sequence selected from the group consisting of SEQ ID NO: 3 (NMS-6), SEQ ID NO: 66 (NMS-118), SEQ ID NO: 67 (NMS-119), SEQ ID NO: 28 (NMS-33), SEQ ID NO: 72 (NMS-127), SEQ ID NO: 16 (NMS-20), SEQ ID NO: 82 (NMS-187) and SEQ ID NO: 25 (NMS-30).

[27]

The antisense oligomer or pharmaceutically acceptable salt or hydrate thereof according to [23] above, wherein the antisense oligomer (C) consists of a nucleotide sequence shown in SEQ ID NO: 12 (NMS-16).

[28]

The antisense oligomer or pharmaceutically acceptable salt or hydrate thereof according to [23] above, wherein the antisense oligomer (D) consists of a nucleotide sequence shown in SEQ ID NO: 4 (NMS-7).

[29]

The antisense oligomer or pharmaceutically acceptable salt or hydrate thereof according to [23] above, wherein the antisense oligomer (E) consists of a nucleotide sequence shown in SEQ ID NO: 90 (NMS-51).

[30]

The antisense oligomer or pharmaceutically acceptable salt or hydrate thereof according to [23] above, wherein the antisense oligomer (F) consists of any one nucleotide sequence selected from the group consisting of SEQ ID NO: 91 (NMS-52), SEQ ID NO: 28 (NMS-33) and SEQ ID NO: 25 (NMS-30), SEQ ID NO: 41 (NMS-61), SEQ ID NO: 24 (NMS-29), SEQ ID NO: 42 (NMS-62), SEQ ID NO: 43 (NMS-63), SEQ ID NO: 11 (NMS-15), SEQ ID NO: 67 (NMS-119), SEQ ID NO: 80 (NMS-161) and SEQ ID NO: 82 (NMS-187).

[31]

The antisense oligomer or pharmaceutically acceptable salt or hydrate thereof according to [23] above, wherein the antisense oligomer (G) consists of a nucleotide sequence shown in SEQ ID NO: 7 (NMS-10).

[32]

The antisense oligomer or pharmaceutically acceptable salt or hydrate thereof according to [23] above, wherein the antisense oligomer (H) consists of any one nucleotide sequence selected from the group consisting of SEQ ID NO: 4 (NMS-7), SEQ ID NO: 9 (NMS-12), SEQ ID NO: 10 (NMS-14) and SEQ ID NO: 14 (NMS-18).

[33]

The antisense oligomer or pharmaceutically acceptable salt or hydrate thereof according to any one of [23] to [32] above, wherein the antisense oligomer is an oligonucleotide.

[34]

The antisense oligomer or pharmaceutically acceptable salt or hydrate thereof according to [33] above, wherein at least one sugar moiety and/or at least one phosphate bond moiety in nucleotides constituting the oligonucleotide is modified.

[35]

The antisense oligomer or pharmaceutically acceptable salt or hydrate thereof according to [34] above, wherein the at least one sugar moiety in nucleotides constituting the oligonucleotide is a ribose in which the —OH group at the 2'-position is substituted with any group selected from the group consisting of OR, R, R'OR, SH, SR, $NH_2$, NHR, $NR_2$, $N_3$, CN, F, Cl, Br and I (wherein R represents alkyl or aryl, and R' represents alkylene).

[36]

The antisense oligomer or pharmaceutically acceptable salt or hydrate thereof according to [34] or [35] above, wherein the at least one phosphate bond moiety in nucleotides constituting the oligonucleotide is any one selected from the group consisting of a phosphorothioate bond, a phosphorodithioate bond, an alkylphosphonate bond, a phosphoroamidate bond and a boranophosphate bond.

[37]

The antisense oligomer or pharmaceutically acceptable salt or hydrate thereof according to any one of [23] to [32] above, wherein the antisense oligomer is a morpholino oligomer.

[38]

The antisense oligomer or pharmaceutically acceptable salt or hydrate thereof according to [37] above, wherein the morpholino oligomer is a phosphorodiamidate morpholino oligomer.

[39]

The antisense oligomer or pharmaceutically acceptable salt or hydrate thereof according to [37] or [38] above, whose 5'-terminal end is any one of the groups represented by chemical formulae (1) to (3) shown below.

[Formula 2]

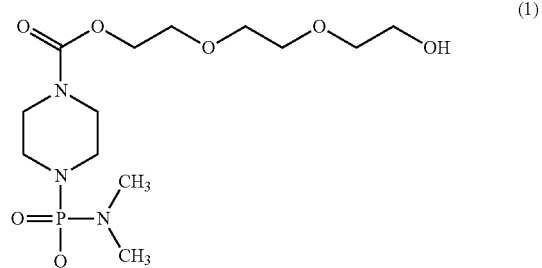

(1)

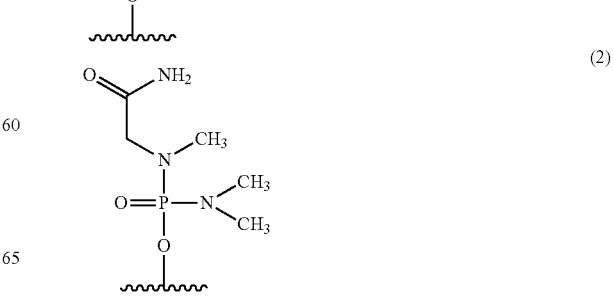

(2)

-continued

(3)

[40]

A pharmaceutical composition comprising the antisense oligomer or pharmaceutically acceptable salt or hydrate thereof according to any one of [23] to [39] above.

[41]

The pharmaceutical composition according to [40] above, which further comprises a pharmaceutically acceptable carrier.

[42]

The pharmaceutical composition according to [40] or [41] above for use in the treatment of an amyotrophic disease or a muscle wasting disease.

[43]

The pharmaceutical composition according to [42] above for use in the treatment of muscular dystrophy.

[44]

A method for prevention or treatment of an amyotrophic disease or a muscle wasting disease, which comprises administering a subject in need of prevention or treatment of an amyotrophic disease or a muscle wasting disease with a therapeutically effective amount of the antisense oligomer or pharmaceutically acceptable salt or hydrate thereof according to any one of [23] to [39] above.

[45]

The method according to [44] above, wherein the amyotrophic disease or muscle wasting disease is muscular dystrophy.

[46]

The method according to [44] or [45] above, wherein the subject is a human subject.

[47]

Use of the antisense oligomer or pharmaceutically acceptable salt or hydrate thereof according to any one of [23] to [39] above in the manufacture of a pharmaceutical composition for treatment of an amyotrophic disease or a muscle wasting disease.

[48]

The antisense oligomer or pharmaceutically acceptable salt or hydrate thereof according to any one of [23] to [39] above for use in the treatment of an amyotrophic disease or a muscle wasting disease.

Effects of the Invention

Antisense oligomers according to some embodiments of the present invention allow induction of exon skipping in the myostatin gene. In addition, an amyotrophic disease or a muscle wasting disease can be prevented or treated when an antisense oligomer according to a preferred embodiment of the present invention or a pharmaceutically acceptable salt or hydrate thereof is administered to a subject in need of prevention or treatment of an amyotrophic disease or a muscle wasting disease.

DESCRIPTION OF EMBODIMENTS

Figure 1:
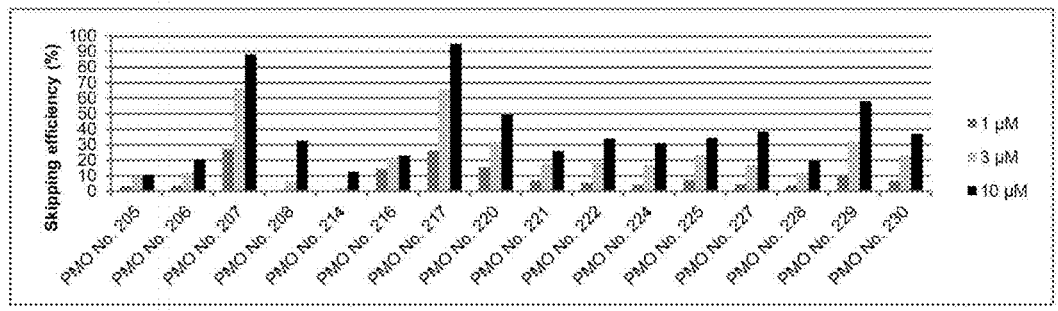
FIG. 1 is a graph showing the efficiency of exon 2 skipping in the human myostatin gene in a human rhabdomyosarcoma cell line (RD cells).
Figure 2:
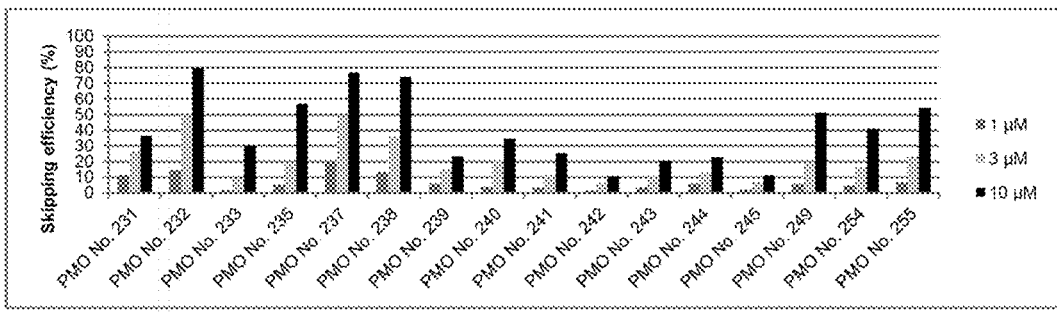
FIG. 2 is a graph showing the efficiency of exon 2 skipping in the human myostatin gene in a human rhabdomyosarcoma cell line (RD cells).
Figure 3:
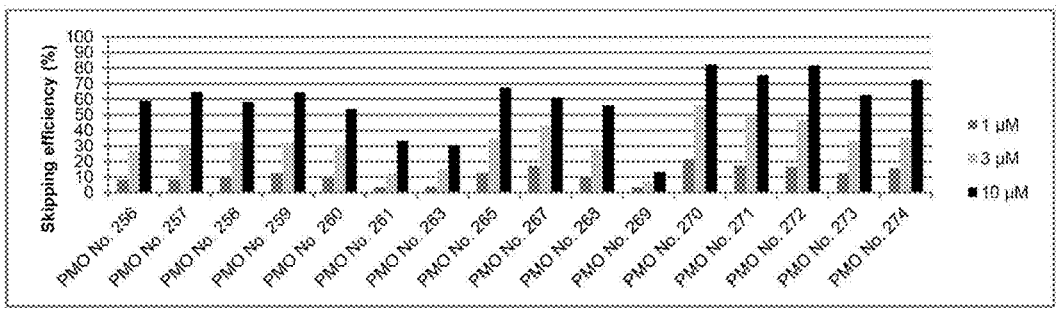
FIG. 3 is a graph showing the efficiency of exon 2 skipping in the human myostatin gene in a human rhabdomyosarcoma cell line (RD cells).
Figure 4:
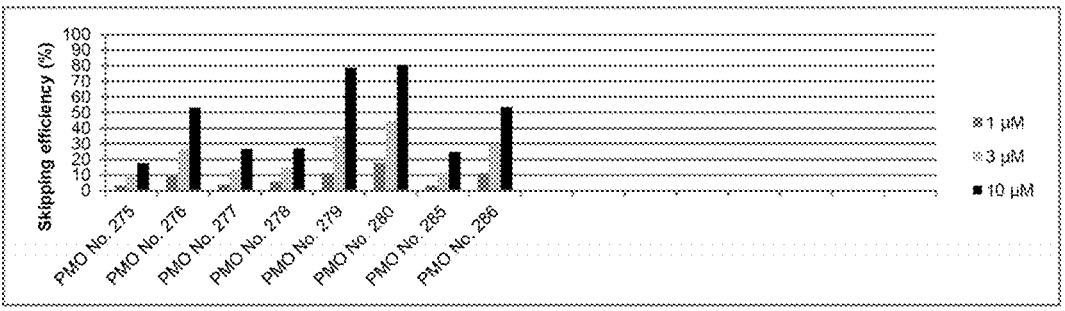
FIG. 4 is a graph showing the efficiency of exon 2 skipping in the human myostatin gene in a human rhabdomyosarcoma cell line (RD cells).
Figure 5:
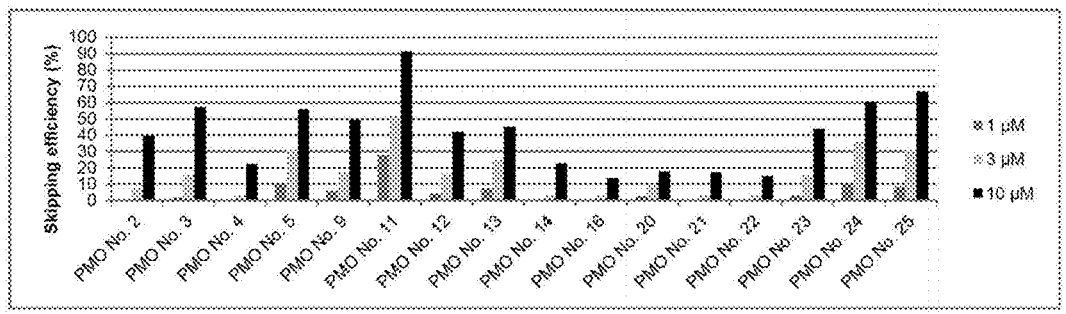
FIG. 5 is a graph showing the efficiency of exon 2 skipping in the human myostatin gene in a human rhabdomyosarcoma cell line (RD cells).
Figure 6:
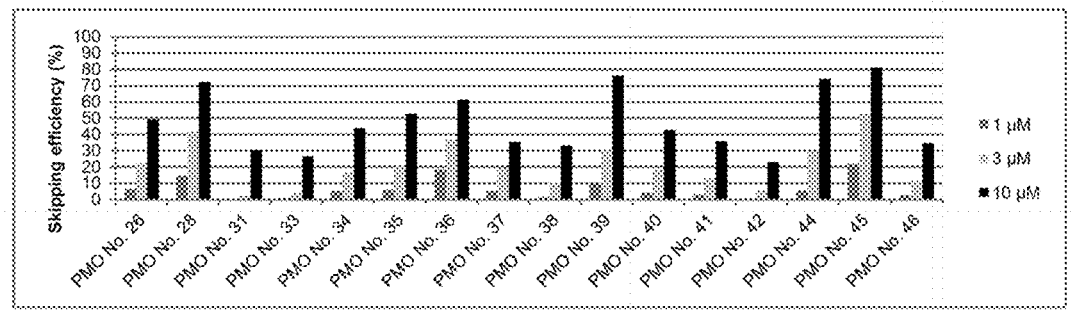
FIG. 6 is a graph showing the efficiency of exon 2 skipping in the human myostatin gene in a human rhabdomyosarcoma cell line (RD cells).
Figure 7:
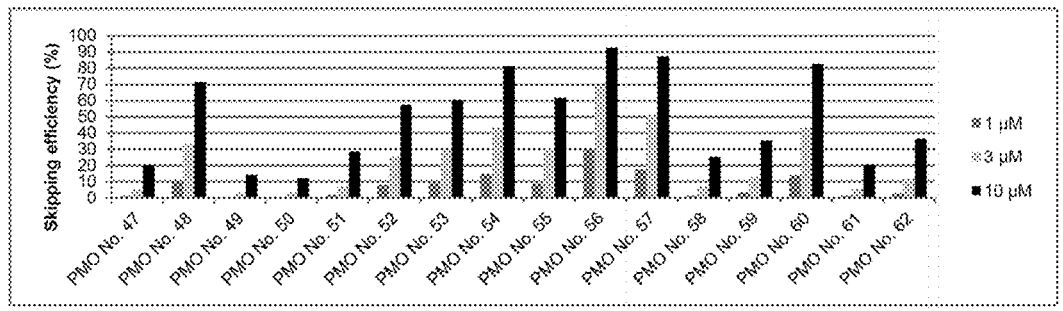
FIG. 7 is a graph showing the efficiency of exon 2 skipping in the human myostatin gene in a human rhabdomyosarcoma cell line (RD cells).
Figure 8:
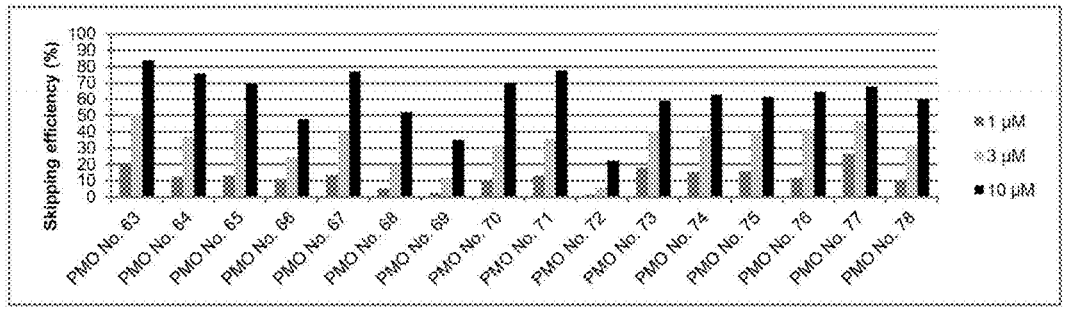
FIG. 8 is a graph showing the efficiency of exon 2 skipping in the human myostatin gene in a human rhabdomyosarcoma cell line (RD cells).
Figure 9:
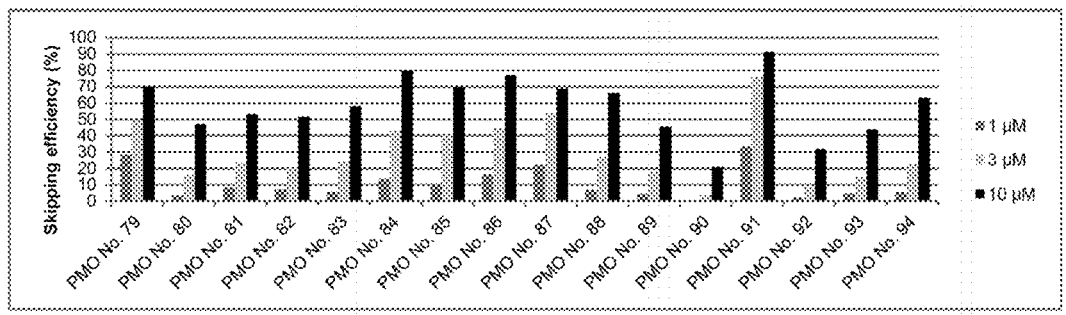
FIG. 9 is a graph showing the efficiency of exon 2 skipping in the human myostatin gene in a human rhabdomyosarcoma cell line (RD cells).
Figure 10:
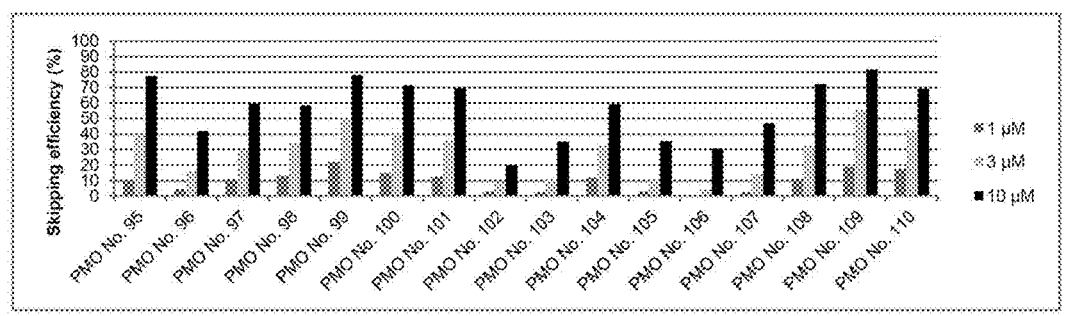
FIG. 10 is a graph showing the efficiency of exon 2 skipping in the human myostatin gene in a human rhabdomyosarcoma cell line (RD cells).
Figure 11:
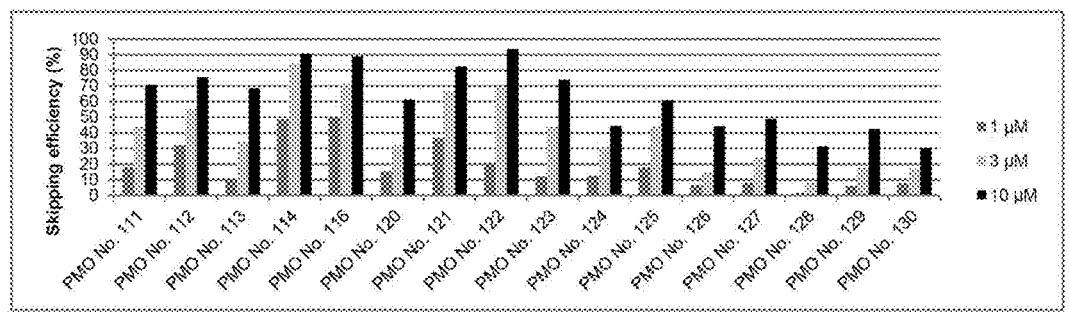
FIG. 11 is a graph showing the efficiency of exon 2 skipping in the human myostatin gene in a human rhabdomyosarcoma cell line (RD cells).
Figure 12:
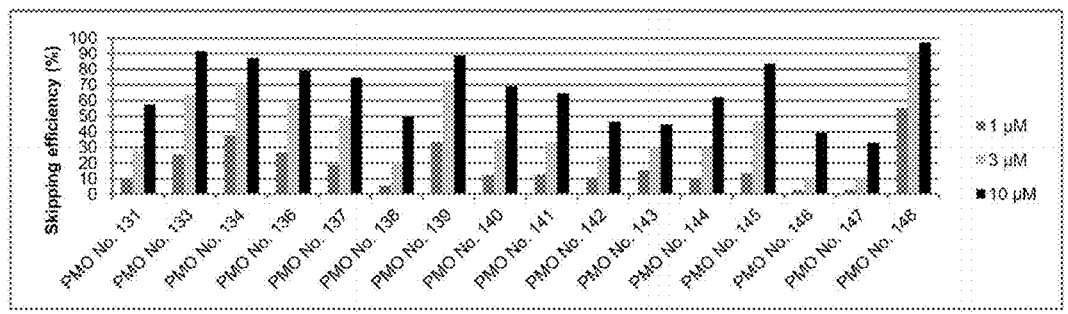
FIG. 12 is a graph showing the efficiency of exon 2 skipping in the human myostatin gene in a human rhabdomyosarcoma cell line (RD cells).
Figure 13:
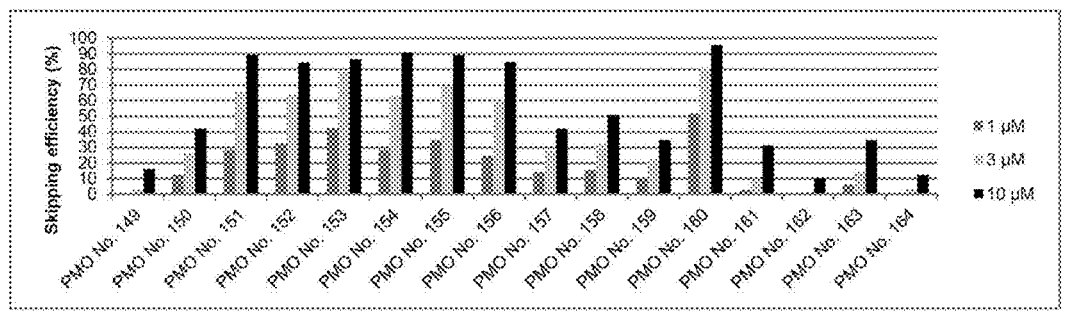
FIG. 13 is a graph showing the efficiency of exon 2 skipping in the human myostatin gene in a human rhabdomyosarcoma cell line (RD cells).
Figure 14:
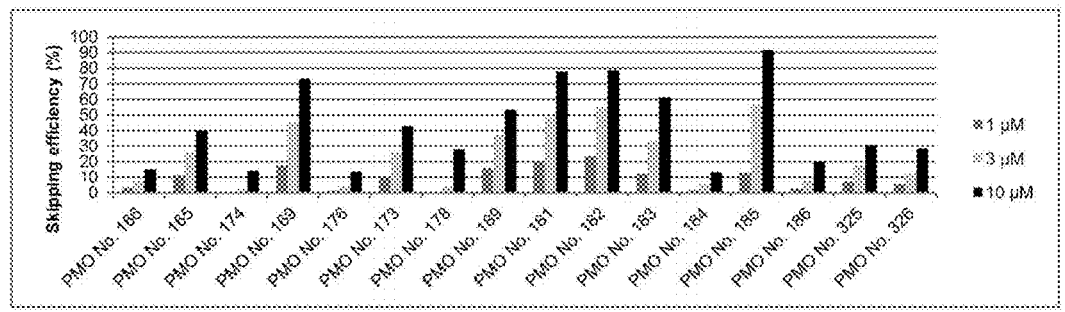
FIG. 14 is a graph showing the efficiency of exon 3 skipping in the human myostatin gene in a human rhabdomyosarcoma cell line (RD cells).

The present invention will be described in more detail below. The following embodiments are illustrated to describe the present invention, and it is not intended to limit the present invention only to these embodiments. The present invention can be implemented in various modes without departing from the spirit of the present invention.

It should be noted that all publications cited herein, including prior art documents, patent gazettes and other patent documents, are incorporated herein by reference. Moreover, this specification incorporates the contents disclosed in the specification and drawings of Japanese Patent Application No. 2015-18214 (filed on Sep. 16, 2015), based on which the present application claims priority.

1. Antisense Oligomer of the Present Invention or a Pharmaceutically Acceptable Salt or Hydrate Thereof The present invention provides an antisense oligomer which allows exon 2 skipping in the myostatin gene, or a pharmaceutically acceptable salt or hydrate thereof (hereinafter collectively referred to as "the antisense oligomer of the present invention").

The following "antisense oligomer A of the present invention" and "antisense oligomer B of the present invention" may also be collectively referred to as "the antisense oligomer of the present invention."

1.1. Antisense Oligomer A of the Present Invention

The antisense oligomer A of the present invention is an antisense oligomer of 14 to 30 bases in length comprising connected two unit oligomers selected from the group consisting of (a) and (b) shown below, or a pharmaceutically acceptable salt or hydrate thereof:
(a) a first unit oligomer comprising a nucleotide sequence complementary to a first nucleotide sequence consisting of contiguous 7 to 15 bases in exon 2 of the human or mouse myostatin gene; and
(b) a second unit oligomer comprising a nucleotide sequence complementary to a second nucleotide sequence consisting of contiguous 7 to 15 bases in said exon 2,
wherein the first nucleotide sequence and the second nucleotide sequence are not contiguous to each other or do not overlap with each other.

The antisense oligomer A of the present invention is more specifically an antisense oligomer shown in (c) or (d) below, or a pharmaceutically acceptable salt or hydrate thereof:
(c) an antisense oligomer of 14 to 30 bases in length comprising connected two unit oligomers selected from the group consisting of unit oligomers (c-1) to (c-6) shown below:
  (c-1) a unit oligomer consisting of a nucleotide sequence complementary to a nucleotide sequence consisting of contiguous 7 to 15 bases selected from a nucleotide sequence located at positions −10 to 45 from the 5'-terminal end of exon 2 in the human myostatin gene;
  (c-2) a unit oligomer consisting of a nucleotide sequence complementary to a nucleotide sequence consisting of contiguous 7 to 15 bases selected from a nucleotide sequence located at positions 91 to 135 from the 5'-terminal end of exon 2 in the human myostatin gene;
  (c-3) a unit oligomer consisting of a nucleotide sequence complementary to a nucleotide sequence consisting of contiguous 7 to 15 bases selected from a nucleotide sequence located at positions 121 to 155 from the 5'-terminal end of exon 2 in the human myostatin gene;
  (c-4) a unit oligomer consisting of a nucleotide sequence complementary to a nucleotide sequence consisting of contiguous 7 to 15 bases selected from a nucleotide sequence located at positions 166 to 210 from the 5'-terminal end of exon 2 in the human myostatin gene;
  (c-5) a unit oligomer consisting of a nucleotide sequence complementary to a nucleotide sequence consisting of contiguous 7 to 15 bases selected from a nucleotide sequence located at positions 204 to 233 from the 5'-terminal end of exon 2 in the human myostatin gene; and
  (c-6) a unit oligomer consisting of a nucleotide sequence complementary to a nucleotide sequence consisting of contiguous 7 to 15 bases selected from a nucleotide sequence located at positions 326 to 374 from the 5'-terminal end of exon 2 in the human myostatin gene; or
(d) an antisense oligomer of 14 to 30 bases in length comprising connected two unit oligomers selected from the group consisting of unit oligomers (d-1) to (d-7) shown below:
  (d-1) a unit oligomer consisting of a nucleotide sequence complementary to a nucleotide sequence consisting of contiguous 7 to 15 bases selected from a nucleotide sequence located at positions −1 to 65 from the 5'-terminal end of exon 2 in the mouse myostatin gene;
  (d-2) a unit oligomer consisting of a nucleotide sequence complementary to a nucleotide sequence consisting of contiguous 7 to 15 bases selected from a nucleotide sequence located at positions 91 to 135 from the 5'-terminal end of exon 2 in the mouse myostatin gene;
  (d-3) a unit oligomer consisting of a nucleotide sequence complementary to a nucleotide sequence consisting of contiguous 7 to 15 bases selected from a nucleotide sequence located at positions 121 to 155 from the 5'-terminal end of exon 2 in the mouse myostatin gene;
  (d-4) a unit oligomer consisting of a nucleotide sequence complementary to a nucleotide sequence consisting of contiguous 7 to 15 bases selected from a nucleotide sequence located at positions 151 to 210 from the 5'-terminal end of exon 2 in the mouse myostatin gene;
  (d-5) a unit oligomer consisting of a nucleotide sequence complementary to a nucleotide sequence consisting of contiguous 7 to 15 bases selected from a nucleotide sequence located at positions 196 to 233 from the 5'-terminal end of exon 2 in the mouse myostatin gene;
  (d-6) a unit oligomer consisting of a nucleotide sequence complementary to a nucleotide sequence consisting of contiguous 7 to 15 bases selected from a nucleotide sequence located at positions 266 to 295 from the 5'-terminal end of exon 2 in the mouse myostatin gene; and
  (d-7) a unit oligomer consisting of a nucleotide sequence complementary to a nucleotide sequence consisting of contiguous 7 to 15 bases selected from a nucleotide sequence located at positions 326 to 374 from the 5'-terminal end of exon 2 in the mouse myostatin gene.

Further, the antisense oligomer A of the present invention is more specifically an antisense oligomer shown in (e) or (f) below, or a pharmaceutically acceptable salt or hydrate thereof:
(e) an antisense oligomer of 14 to 30 bases in length comprising connected two unit oligomers selected from the group consisting of unit oligomers (e-1) to (e-6) shown below:
  (e-1) a unit oligomer consisting of a nucleotide sequence complementary to a nucleotide sequence consisting of contiguous 7 to 15 bases selected from a nucleotide sequence located at positions −4 to 25 from the 5'-terminal end of exon 2 in the human myostatin gene;
  (e-2) a unit oligomer consisting of a nucleotide sequence complementary to a nucleotide sequence consisting of contiguous 7 to 15 bases selected from a nucleotide sequence located at positions 112 to 131 from the 5'-terminal end of exon 2 in the human myostatin gene;
  (e-3) a unit oligomer consisting of a nucleotide sequence complementary to a nucleotide sequence consisting of contiguous 7 to 15 bases selected from a nucleotide sequence located at positions 128 to 142 from the 5'-terminal end of exon 2 in the human myostatin gene;
  (e-4) a unit oligomer consisting of a nucleotide sequence complementary to a nucleotide sequence consisting of contiguous 7 to 15 bases selected from a nucleotide sequence located at positions 169 to 206 from the 5'-terminal end of exon 2 in the human myostatin gene;
  (e-5) a unit oligomer consisting of a nucleotide sequence complementary to a nucleotide sequence consisting of contiguous 7 to 15 bases selected from a nucleotide sequence located at positions 209 to 228 from the 5'-terminal end of exon 2 in the human myostatin gene; and
  (e-6) a unit oligomer consisting of a nucleotide sequence complementary to a nucleotide sequence consisting of contiguous 7 to 15 bases selected from a nucleotide sequence located at positions 331 to 365 from the 5'-terminal end of exon 2 in the human myostatin gene; or
(f) an antisense oligomer of 14 to 30 bases in length comprising connected two unit oligomers selected from the group consisting of unit oligomers (f-1) to (f-7) shown below:

(f-1) a unit oligomer consisting of a nucleotide sequence complementary to a nucleotide sequence consisting of contiguous 7 to 15 bases selected from a nucleotide sequence located at positions 1 to 18 from the 5'-terminal end of exon 2 in the mouse myostatin gene;

(f-2) a unit oligomer consisting of a nucleotide sequence complementary to a nucleotide sequence consisting of contiguous 7 to 15 bases selected from a nucleotide sequence located at positions 116 to 131 from the 5'-terminal end of exon 2 in the mouse myostatin gene;

(f-3) a unit oligomer consisting of a nucleotide sequence complementary to a nucleotide sequence consisting of contiguous 7 to 15 bases selected from a nucleotide sequence located at positions 130 to 140 from the 5'-terminal end of exon 2 in the mouse myostatin gene;

(f-4) a unit oligomer consisting of a nucleotide sequence complementary to a nucleotide sequence consisting of contiguous 7 to 15 bases selected from a nucleotide sequence located at positions 160 to 206 from the 5'-terminal end of exon 2 in the mouse myostatin gene;

(f-5) a unit oligomer consisting of a nucleotide sequence complementary to a nucleotide sequence consisting of contiguous 7 to 15 bases selected from a nucleotide sequence located at positions 211 to 225 from the 5'-terminal end of exon 2 in the mouse myostatin gene;

(f-6) a unit oligomer consisting of a nucleotide sequence complementary to a nucleotide sequence consisting of contiguous 7 to 15 bases selected from a nucleotide sequence located at positions 271 to 282 from the 5'-terminal end of exon 2 in the mouse myostatin gene; and (f-7) a unit oligomer consisting of a nucleotide sequence complementary to a nucleotide sequence consisting of contiguous 7 to 15 bases selected from a nucleotide sequence located at positions 341 to 365 from the 5'-terminal end of exon 2 in the mouse myostatin gene.

In the antisense oligomer A of the present invention, the term "gene" is intended to include not only a genomic gene, but also cDNA, precursor mRNA, and mRNA. The gene is preferably precursor mRNA, i.e., pre-mRNA.

Pre-mRNA transcribed from the myostatin gene contains three exons and two introns in the order of (5'-terminal end) exon 1, intron 1, exon 2, intron 2 and exon 3 (3'-terminal end). Pre-mRNA is spliced to generate mature mRNA. The nucleotide sequences of the human and mouse wild-type myostatin genes are known (RefSeq Accession No. NM_005259 (human) and RefSeq Accession No. NM_010834 (mouse), respectively). The nucleotide sequence of exon 2 in the wild-type myostatin gene is as shown below:

exon 2 (human): SEQ ID NO: 323; and
exon 2 (mouse): SEQ ID NO: 324.

In the above unit oligomer (c-1), the "nucleotide sequence located at positions −10 to 45 from the 5'-terminal end of exon 2 in the human myostatin gene" is shown in SEQ ID NO: 337.

In the above unit oligomer (c-2), the "nucleotide sequence located at positions 91 to 135 from the 5'-terminal end of exon 2 in the human myostatin gene" is shown in SEQ ID NO: 338.

In the above unit oligomer (c-3), the "nucleotide sequence located at positions 121 to 155 from the 5'-terminal end of exon 2 in the human myostatin gene" is shown in SEQ ID NO: 339.

In the above unit oligomer (c-4), the "nucleotide sequence located at positions 166 to 210 from the 5'-terminal end of exon 2 in the human myostatin gene" is shown in SEQ ID NO: 340.

In the above unit oligomer (c-5), the "nucleotide sequence located at positions 204 to 233 from the 5'-terminal end of exon 2 in the human myostatin gene" is shown in SEQ ID NO: 341.

In the above unit oligomer (c-6), the "nucleotide sequence located at positions 326 to 374 from the 5'-terminal end of exon 2 in the human myostatin gene" is shown in SEQ ID NO: 342.

In the above unit oligomer (d-1), the "nucleotide sequence located at positions −10 to 65 from the 5'-terminal end of exon 2 in the mouse myostatin gene" is shown in SEQ ID NO: 343.

In the above unit oligomer (d-2), the "nucleotide sequence located at positions 91 to 135 from the 5'-terminal end of exon 2 in the mouse myostatin gene" is shown in SEQ ID NO: 344.

In the above unit oligomer (d-3), the "nucleotide sequence located at positions 121 to 155 from the 5'-terminal end of exon 2 in the mouse myostatin gene" is shown in SEQ ID NO: 345.

In the above unit oligomer (d-4), the "nucleotide sequence located at positions 151 to 210 from the 5'-terminal end of exon 2 in the mouse myostatin gene" is shown in SEQ ID NO: 346.

In the above unit oligomer (d-5), the "nucleotide sequence located at positions 196 to 233 from the 5'-terminal end of exon 2 in the mouse myostatin gene" is shown in SEQ ID NO: 347.

In the above unit oligomer (d-6), the "nucleotide sequence located at positions 266 to 295 from the 5'-terminal end of exon 2 in the mouse myostatin gene" is shown in SEQ ID NO: 364.

In the above unit oligomer (d-7), the "nucleotide sequence located at positions 326 to 374 from the 5'-terminal end of exon 2 in the mouse myostatin gene" is shown in SEQ ID NO: 348.

In the above unit oligomer (e-1), the "nucleotide sequence located at positions −4 to 25 from the 5'-terminal end of exon 2 in the human myostatin gene" is shown in SEQ ID NO: 349.

In the above unit oligomer (e-2), the "nucleotide sequence located at positions 112 to 131 from the 5'-terminal end of exon 2 in the human myostatin gene" is shown in SEQ ID NO: 350.

In the above unit oligomer (e-3), the "nucleotide sequence located at positions 128 to 142 from the 5'-terminal end of exon 2 in the human myostatin gene" is shown in SEQ ID NO: 351.

In the above unit oligomer (e-4), the "nucleotide sequence located at positions 169 to 206 from the 5'-terminal end of exon 2 in the human myostatin gene" is shown in SEQ ID NO: 352.

In the above unit oligomer (e-5), the "nucleotide sequence located at positions 209 to 228 from the 5'-terminal end of exon 2 in the human myostatin gene" is shown in SEQ ID NO: 353.

In the above unit oligomer (e-6), the "nucleotide sequence located at positions 331 to 365 from the 5'-terminal end of exon 2 in the human myostatin gene" is shown in SEQ ID NO: 354.

In the above unit oligomer (f-1), the "nucleotide sequence located at positions 1 to 18 from the 5'-terminal end of exon 2 in the mouse myostatin gene" is shown in SEQ ID NO: 355.

In the above unit oligomer (f-2), the "nucleotide sequence located at positions 116 to 131 from the 5'-terminal end of exon 2 in the mouse myostatin gene" is shown in SEQ ID NO: 356.

In the above unit oligomer (f-3), the "nucleotide sequence located at positions 130 to 140 from the 5'-terminal end of exon 2 in the mouse myostatin gene" is shown in SEQ ID NO: 357.

In the above unit oligomer (f-4), the "nucleotide sequence located at positions 160 to 206 from the 5'-terminal end of exon 2 in the mouse myostatin gene" is shown in SEQ ID NO: 358.

In the above unit oligomer (f-5), the "nucleotide sequence located at positions 211 to 225 from the 5'-terminal end of exon 2 in the mouse myostatin gene" is shown in SEQ ID NO: 359.

In the above unit oligomer (f-6), the "nucleotide sequence located at positions 271 to 282 from the 5'-terminal end of exon 2 in the mouse myostatin gene" is shown in SEQ ID NO: 365.

In the above unit oligomer (f-7), the "nucleotide sequence located at positions 341 to 365 from the 5'-terminal end of exon 2 in the mouse myostatin gene" is shown in SEQ ID NO: 366.

The antisense oligomer A of the present invention has now been prepared to cause exon 2 skipping in the myostatin gene with the aim of modifying a protein encoded by the myostatin gene into a mutant protein lacking the function of myostatin. The "function of myostatin" refers to, for example, the function or activity to negatively control skeletal muscle mass. Thus, exon 2 in the myostatin gene to be skipped by the antisense oligomer A of the present invention includes not only wild-type, but also mutated forms.

More specifically, mutated exon 2 in the myostatin gene or a portion thereof is a polynucleotide shown in (a) or (b) below:

(a) a polynucleotide hybridizable under stringent conditions with a polynucleotide consisting of a nucleotide sequence complementary to any nucleotide sequence selected from the group consisting of SEQ ID NO: 323 (exon 2 in the human myostatin gene), SEQ ID NO: 337 (a nucleotide sequence located at positions −10 to 45 from the 5'-terminal end of exon 2 in the human myostatin gene), SEQ ID NO: 338 (a nucleotide sequence located at positions 91 to 135 from the 5'-terminal end of exon 2 in the human myostatin gene), SEQ ID NO: 339 (a nucleotide sequence located at positions 121 to 155 from the 5'-terminal end of exon 2 in the human myostatin gene), SEQ ID NO: 340 (a nucleotide sequence located at positions 166 to 210 from the 5'-terminal end of exon 2 in the human myostatin gene), SEQ ID NO: 341 (a nucleotide sequence located at positions 204 to 233 from the 5'-terminal end of exon 2 in the human myostatin gene), SEQ ID NO: 342 (a nucleotide sequence located at positions 326 to 374 from the 5'-terminal end of exon 2 in the human myostatin gene), SEQ ID NO: 349 (a nucleotide sequence located at positions −4 to 25 from the 5'-terminal end of exon 2 in the human myostatin gene), SEQ ID NO: 350 (a nucleotide sequence located at positions 112 to 131 from the 5'-terminal end of exon 2 in the human myostatin gene), SEQ ID NO: 351 (a nucleotide sequence located at positions 128 to 142 from the 5'-terminal end of exon 2 in the human myostatin gene), SEQ ID NO: 352 (a nucleotide sequence located at positions 169 to 206 from the 5'-terminal end of exon 2 in the human myostatin gene), SEQ ID NO: 353 (a nucleotide sequence located at positions 209 to 228 from the 5'-terminal end of exon 2 in the human myostatin gene), SEQ ID NO: 354 (a nucleotide sequence located at positions 331 to 365 from the 5'-terminal end of exon 2 in the human myostatin gene), SEQ ID NO: 324 (exon 2 in the mouse myostatin gene), SEQ ID NO: 343 (a nucleotide sequence located at positions −10 to 65 from the 5'-terminal end of exon 2 in the mouse myostatin gene), SEQ ID NO: 344 (a nucleotide sequence located at positions 91 to 135 from the 5'-terminal end of exon 2 in the mouse myostatin gene), SEQ ID NO: 345 (a nucleotide sequence located at positions 121 to 155 from the 5'-terminal end of exon 2 in the mouse myostatin gene) and SEQ ID NO: 346 (a nucleotide sequence located at positions 151 to 210 from the 5'-terminal end of exon 2 in the mouse myostatin gene), SEQ ID NO: 347 (a nucleotide sequence located at positions 196 to 233 from the 5'-terminal end of exon 2 in the mouse myostatin gene), SEQ ID NO: 364 (a nucleotide sequence located at positions 266 to 295 from the 5'-terminal end of exon 2 in the mouse myostatin gene), SEQ ID NO: 348 (a nucleotide sequence located at positions 326 to 374 from the 5'-terminal end of exon 2 in the mouse myostatin gene), SEQ ID NO: 355 (a nucleotide sequence located at positions 1 to 18 from the 5'-terminal end of exon 2 in the mouse myostatin gene), SEQ ID NO: 356 (a nucleotide sequence located at positions 116 to 131 from the 5'-terminal end of exon 2 in the mouse myostatin gene), SEQ ID NO: 357 (a nucleotide sequence located at positions 130 to 140 from the 5'-terminal end of exon 2 in the mouse myostatin gene), SEQ ID NO: 358 (a nucleotide sequence located at positions 160 to 206 from the 5'-terminal end of exon 2 in the mouse myostatin gene), SEQ ID NO: 359 (a nucleotide sequence located at positions 211 to 255 from the 5'-terminal end of exon 2 in the mouse myostatin gene), SEQ ID NO: 365 (a nucleotide sequence located at positions 271 to 282 from the 5'-terminal end of exon 2 in the mouse myostatin gene) and SEQ ID NO: 366 (a nucleotide sequence located at positions 341 to 365 from the 5'-terminal end of exon 2 in the mouse myostatin gene); or (b) a polynucleotide consisting of a nucleotide sequence sharing an identity of 90% or more with any nucleotide sequence selected from the group consisting of SEQ ID NO: 323 (exon 2 in the human myostatin gene), SEQ ID NO: 337 (a nucleotide sequence located at positions −10 to 45 from the 5'-terminal end of exon 2 in the human myostatin gene), SEQ ID NO: 338 (a nucleotide sequence located at positions 91 to 135 from the 5'-terminal end of exon 2 in the human myostatin gene), SEQ ID NO: 339 (a nucleotide sequence located at positions 121 to 155 from the 5'-terminal end of exon 2 in the human myostatin gene), SEQ ID NO: 340 (a nucleotide sequence located at positions 166 to 210 from the 5'-terminal end of exon 2 in the human myostatin gene), SEQ ID NO: 341 (a nucleotide sequence located at positions 204 to 233 from the 5'-terminal end of exon 2 in the human myostatin gene), SEQ ID NO: 342 (a nucleotide sequence located at positions 326 to 374 from the 5'-terminal end of exon 2 in the human myostatin gene), SEQ ID NO: 349 (a nucleotide sequence located at positions −4 to 25 from the 5'-terminal end of exon 2 in the human myostatin gene), SEQ ID NO: 350 (a nucleotide sequence located at positions 112 to 131 from the 5'-terminal end of exon 2 in the human myostatin gene), SEQ ID NO: 351 (a nucleotide sequence located at positions 128 to 142 from the 5'-terminal end of exon 2 in the human myostatin gene), SEQ ID NO: 352 (a nucleotide sequence located at positions 169 to 206 from the 5'-terminal end of exon 2 in the human myostatin gene), SEQ ID NO: 353 (a nucleotide sequence located at positions 209 to 228 from the 5'-terminal end of exon 2 in the human myostatin gene), SEQ ID NO: 354 (a nucleotide sequence located at positions 331 to 365 from the 5'-terminal end of exon 2 in the human myostatin gene), SEQ ID NO: 324 (exon 2 in the mouse myostatin gene), SEQ ID NO: 343 (a nucleotide sequence located at positions −10 to 65 from the 5'-terminal end of exon 2 in the mouse myostatin gene), SEQ ID NO: 344 (a nucleotide sequence located at positions 91 to 135 from the 5'-terminal end of exon 2 in the mouse myostatin gene), SEQ ID NO: 345 (a nucleotide sequence located at positions 121 to 155 from the 5'-terminal end of exon 2 in the mouse myostatin gene) and SEQ ID NO: 346 (a nucleotide sequence located at positions 151 to 210 from the 5'-terminal end of exon 2 in the mouse myostatin gene), SEQ ID NO: 347 (a nucleotide sequence located at positions 196 to 233 from the 5'-terminal end of exon 2 in the mouse myostatin gene), SEQ ID NO: 364 (a nucleotide sequence located at positions 266 to 295 from the 5'-terminal end of exon 2 in the mouse myostatin gene), SEQ ID NO: 348 (a nucleotide sequence located at positions 326 to 374 from the 5'-terminal end of exon 2 in the mouse myostatin gene), SEQ ID NO: 355 (a nucleotide sequence located at positions 1 to 18 from the 5'-terminal end of exon 2 in the mouse myostatin gene), SEQ ID NO: 356 (a nucleotide sequence located at positions 116 to 131 from the 5'-terminal end of exon 2 in the mouse myostatin gene), SEQ ID NO: 357 (a nucleotide sequence located at positions 130 to 140 from the 5'-terminal end of exon 2 in the mouse myostatin gene), SEQ ID NO: 358 (a nucleotide sequence located at positions 160 to 206 from the 5'-terminal end of exon 2 in the mouse myostatin gene), SEQ ID NO: 359 (a nucleotide sequence located at positions 211 to 255 from the 5'-terminal end of exon 2 in the mouse myostatin gene), SEQ ID NO: 365 (a nucleotide sequence located at positions 271 to 282 from the 5'-terminal end of exon 2 in the mouse myostatin gene) and SEQ ID NO: 366 (a nucleotide sequence located at positions 341 to 365 from the 5'-terminal end of exon 2 in the mouse myostatin gene).

As used herein, the term "polynucleotide" is intended to mean DNA or RNA.

As used herein, the expression "nucleotide sequence complementary" is not limited only to a nucleotide sequence forming Watson-Crick pairs with a target nucleotide sequence and also includes nucleotide sequences forming wobble base pairs with a target nucleotide sequence. In this regard, a Watson-Crick pair is intended to mean a base pair which forms hydrogen bonding between adenine and thymine, between adenine and uracil or between guanine and cytosine, whereas a wobble base pair is intended to mean a base pair which forms hydrogen bonding between guanine and uracil, between inosine and uracil, between inosine and adenine or between inosine and cytosine. Moreover, such a "nucleotide sequence complementary" does not necessarily have 100% complementarity to a target nucleotide sequence and may contain non-complementary bases (e.g., 1 to 3 bases, 1 or 2 bases, or a single base) to the target nucleotide sequence.

As used herein, the expression "polynucleotide hybridizable under stringent conditions" is intended to mean, for example, an antisense oligomer that can be obtained by means of colony hybridization, plaque hybridization, Southern hybridization or other hybridization techniques using, as a probe, the whole or a part of a polynucleotide consisting of a nucleotide sequence complementary to any nucleotide sequence selected from the group consisting of SEQ ID NO: 323 (exon 2 in the human myostatin gene), SEQ ID NO: 337 (a nucleotide sequence located at positions −10 to 45 from the 5'-terminal end of exon 2 in the human myostatin gene), SEQ ID NO: 338 (a nucleotide sequence located at positions 91 to 135 from the 5'-terminal end of exon 2 in the human myostatin gene), SEQ ID NO: 339 (a nucleotide sequence located at positions 121 to 155 from the 5'-terminal end of exon 2 in the human myostatin gene), SEQ ID NO: 340 (a nucleotide sequence located at positions 166 to 210 from the 5'-terminal end of exon 2 in the human myostatin gene), SEQ ID NO: 341 (a nucleotide sequence located at positions 204 to 233 from the 5'-terminal end of exon 2 in the human myostatin gene), SEQ ID NO: 342 (a nucleotide sequence located at positions 326 to 374 from the 5'-terminal end of exon 2 in the human myostatin gene), SEQ ID NO: 349 (a nucleotide sequence located at positions −4 to 25 from the 5'-terminal end of exon 2 in the human myostatin gene), SEQ ID NO: 350 (a nucleotide sequence located at positions 112 to 131 from the 5'-terminal end of exon 2 in the human myostatin gene), SEQ ID NO: 351 (a nucleotide sequence located at positions 128 to 142 from the 5'-terminal end of exon 2 in the human myostatin gene), SEQ ID NO: 352 (a nucleotide sequence located at positions 169 to 206 from the 5'-terminal end of exon 2 in the human myostatin gene), SEQ ID NO: 353 (a nucleotide sequence located at positions 209 to 228 from the 5'-terminal end of exon 2 in the human myostatin gene), SEQ ID NO: 354 (a nucleotide sequence located at positions 331 to 365 from the 5'-terminal end of exon 2 in the human myostatin gene), SEQ ID NO: 324 (exon 2 in the mouse myostatin gene), SEQ ID NO: 343 (a nucleotide sequence located at positions −10 to 65 from the 5'-terminal end of exon 2 in the mouse myostatin gene), SEQ ID NO: 344 (a nucleotide sequence located at positions 91 to 135 from the 5'-terminal end of exon 2 in the mouse myostatin gene), SEQ ID NO: 345 (a nucleotide sequence located at positions 121 to 155 from the 5'-terminal end of exon 2 in the mouse myostatin gene) and SEQ ID NO: 346 (a nucleotide sequence located at positions 151 to 210 from the 5'-terminal end of exon 2 in the mouse myostatin gene), SEQ ID NO: 347 (a nucleotide sequence located at positions 196 to 233 from the 5'-terminal end of exon 2 in the mouse myostatin gene), SEQ ID NO: 364 (a nucleotide sequence located at positions 266 to 295 from the 5'-terminal end of exon 2 in the mouse myostatin gene), SEQ ID NO: 348 (a nucleotide sequence located at positions 326 to 374 from the 5'-terminal end of exon 2 in the mouse myostatin gene), SEQ ID NO: 355 (a nucleotide sequence located at positions 1 to 18 from the 5'-terminal end of exon 2 in the mouse myostatin gene), SEQ ID NO: 356 (a nucleotide sequence located at positions 116 to 131 from the 5'-terminal end of exon 2 in the mouse myostatin gene), SEQ ID NO: 357 (a nucleotide sequence located at positions 130 to 140 from the 5'-terminal end of exon 2 in the mouse myostatin gene), SEQ ID NO: 358 (a nucleotide sequence located at positions 160 to 206 from the 5'-terminal end of exon 2 in the mouse myostatin gene), SEQ ID NO: 359 (a nucleotide sequence located at positions 211 to 255 from the 5'-terminal end of exon 2 in the mouse myostatin gene), SEQ ID NO: 365 (a nucleotide sequence located at positions 271 to 282 from the 5'-terminal end of exon 2 in the mouse myostatin gene) and SEQ ID NO: 366 (a nucleotide sequence located at positions 341 to 365 from the 5'-terminal end of exon 2 in the mouse myostatin gene). For hybridization, it is possible to use techniques as described in, e.g., "Sambrook & Russell, Molecular Cloning: A Laboratory Manual (Fourth Edition), Cold Spring Harbor, Laboratory Press 2012" and "Ausubel, Current Protocols in Molecular Biology, John Wiley & Sons 1987-1997."

As used herein, the term "stringent conditions" may be any of low stringent conditions, moderately stringent conditions and high stringent conditions. "Low stringent conditions" refer to, for example, conditions of 5×SSC, 5×Denhardt's solution, 0.5% SDS, 50% formamide and 32° C. Likewise, "moderately stringent conditions" refer to, for example, conditions of 5×SSC, 5×Denhardt's solution, 0.5% SDS, 50% formamide and 42° C. or conditions of 5×SSC, 1% SDS, 50 mM Tris-HCl (pH 7.5), 50% formamide and 42° C. "High stringent conditions" refer to, for example, conditions of (1) 5×SSC, 5×Denhardt's solution, 0.5% SDS, 50% formamide and 50° C., (2) 0.2×SSC, 0.1% SDS and 60° C., (3) 0.2×SSC, 0.1% SDS and 62° C., (4) 0.2×SSC, 0.1% SDS and 65° C., or (5) 0.1×SSC, 0.1% SDS and 65° C., but are not limited thereto. Under these conditions, it can be expected that an antisense oligomer having a higher sequence identity is more efficiently obtained at a higher temperature. However, the stringency of hybridization would be affected by a plurality of factors, including temperature, probe concentration, probe length, ionic strength, reaction time, salt concentration and so on. Those skilled in the art would be able to achieve the same stringency by selecting these factors as appropriate.

It should be noted that if a commercially available kit is used for hybridization, an Alkphos Direct Labelling and Detection System (GE Healthcare) may be used for this purpose, by way of example. In this case, hybridization may be accomplished in accordance with the protocol attached to the kit, i.e., a membrane may be incubated overnight with a labeled probe and then washed with a primary washing buffer containing 0.1% (w/v) SDS under conditions of 55° C. to detect the hybridized antisense oligomer. Alternatively, if a commercially available reagent (e.g., PCR labeling mix (Roche Diagnostics)) is used for digoxigenin (DIG) labeling of a probe during probe preparation based on the whole or a part of a nucleotide sequence complementary to any nucleotide sequence selected from the group consisting of SEQ ID NO: 323 (exon 2 in the human myostatin gene), SEQ ID NO: 337 (a nucleotide sequence located at positions −10 to 45 from the 5'-terminal end of exon 2 in the human myostatin gene), SEQ ID NO: 338 (a nucleotide sequence located at positions 91 to 135 from the 5'-terminal end of exon 2 in the human myostatin gene), SEQ ID NO: 339 (a nucleotide sequence located at positions 121 to 155 from the 5'-terminal end of exon 2 in the human myostatin gene), SEQ ID NO: 340 (a nucleotide sequence located at positions 166 to 210 from the 5'-terminal end of exon 2 in the human myostatin gene), SEQ ID NO: 341 (a nucleotide sequence located at positions 204 to 233 from the 5'-terminal end of exon 2 in the human myostatin gene), SEQ ID NO: 342 (a nucleotide sequence located at positions 326 to 374 from the 5'-terminal end of exon 2 in the human myostatin gene), SEQ ID NO: 349 (a nucleotide sequence located at positions −4 to 25 from the 5'-terminal end of exon 2 in the human myostatin gene), SEQ ID NO: 350 (a nucleotide sequence located at positions 112 to 131 from the 5'-terminal end of exon 2 in the human myostatin gene), SEQ ID NO: 351 (a nucleotide sequence located at positions 128 to 142 from the 5'-terminal end of exon 2 in the human myostatin gene), SEQ ID NO: 352 (a nucleotide sequence located at positions 169 to 206 from the 5'-terminal end of exon 2 in the human myostatin gene), SEQ ID NO: 353 (a nucleotide sequence located at positions 209 to 228 from the 5'-terminal end of exon 2 in the human myostatin gene), SEQ ID NO: 354 (a nucleotide sequence located at positions 331 to 365 from the 5'-terminal end of exon 0.2 in the human myostatin gene), SEQ ID NO: 324 (exon 2 in the mouse myostatin gene), SEQ ID NO: 343 (a nucleotide sequence located at positions −10 to 65 from the 5'-terminal end of exon 2 in the mouse myostatin gene), SEQ ID NO: 344 (a nucleotide sequence located at positions 91 to 135 from the 5'-terminal end of exon 2 in the mouse myostatin gene), SEQ ID NO: 345 (a nucleotide sequence located at positions 121 to 155 from the 5'-terminal end of exon 2 in the mouse myostatin gene) and SEQ ID NO: 346 (a nucleotide sequence located at positions 151 to 210 from the 5'-terminal end of exon 2 in the mouse myostatin gene), SEQ ID NO: 347 (a nucleotide sequence located at positions 196 to 233 from the 5'-terminal end of exon 2 in the mouse myostatin gene), SEQ ID NO: 364 (a nucleotide sequence located at positions 266 to 295 from the 5'-terminal end of exon 2 in the mouse myostatin gene), SEQ ID NO: 348 (a nucleotide sequence located at positions 326 to 374 from the 5'-terminal end of exon 2 in the mouse myostatin gene), SEQ ID NO: 355 (a nucleotide sequence located at positions 1 to 18 from the 5'-terminal end of exon 2 in the mouse myostatin gene), SEQ ID NO: 356 (a nucleotide sequence located at positions 116 to 131 from the 5'-terminal end of exon 2 in the mouse myostatin gene), SEQ ID NO: 357 (a nucleotide sequence located at positions 130 to 140 from the 5'-terminal end of exon 2 in the mouse myostatin gene), SEQ ID NO: 358 (a nucleotide sequence located at positions 160 to 206 from the 5'-terminal end of exon 2 in the mouse myostatin gene), SEQ ID NO: 359 (a nucleotide sequence located at positions 211 to 255 from the 5'-terminal end of exon 2 in the mouse myostatin gene), SEQ ID NO: 365 (a nucleotide sequence located at positions 271 to 282 from the 5'-terminal end of exon 2 in the mouse myostatin gene) and SEQ ID NO: 366 (a nucleotide sequence located at positions 341 to 365 from the 5'-terminal end of exon 2 in the mouse myostatin gene), a DIG nucleic acid detection kit (Roche Diagnostics) may be used for detection of hybridization.

In addition to those listed above, other hybridizable antisense oligomers include polynucleotides sharing an identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with any nucleotide sequence selected from the group consisting of SEQ ID NO: 323 (exon 2 in the human myostatin gene), SEQ ID NO: 337 (a nucleotide sequence located at positions −10 to 45 from the 5'-terminal end of exon 2 in the human myostatin gene), SEQ ID NO: 338 (a nucleotide sequence located at positions 91 to 135 from the 5'-terminal end of exon 2 in the human myostatin gene), SEQ ID NO: 339 (a nucleotide sequence located at positions 121 to 155 from the 5'-terminal end of exon 2 in the human myostatin gene), SEQ ID NO: 340 (a nucleotide sequence located at positions 166 to 210 from the 5'-terminal end of exon 2 in the human myostatin gene), SEQ ID NO: 341 (a nucleotide sequence located at positions 204 to 233 from the 5'-terminal end of exon 2 in the human myostatin gene), SEQ ID NO: 342 (a nucleotide sequence located at positions 326 to 374 from the 5'-terminal end of exon 2 in the human myostatin gene), SEQ ID NO: 349 (a nucleotide sequence located at positions −4 to 25 from the 5'-terminal end of exon 2 in the human myostatin gene), SEQ ID NO: 350 (a nucleotide sequence located at positions 112 to 131 from the 5'-terminal end of exon 2 in the human myostatin gene), SEQ ID NO: 351 (a nucleotide sequence located at positions 128 to 142 from the 5'-terminal end of exon 2 in the human myostatin gene), SEQ ID NO: 352 (a nucleotide sequence located at positions 169 to 206 from the 5'-terminal end of exon 2 in the human myostatin gene), SEQ ID NO: 353 (a nucleotide sequence located at positions 209 to 228 from the 5'-terminal end of exon 2 in the human myostatin gene), SEQ ID NO: 354 (a nucleotide sequence located at positions 331 to 365 from the 5'-terminal end of exon 2 in the human myostatin gene), SEQ ID NO: 324 (exon 2 in the mouse myostatin gene), SEQ ID NO: 343 (a nucleotide sequence located at positions −10 to 65 from the 5'-terminal end of exon 2 in the mouse myostatin gene), SEQ ID NO: 344 (a nucleotide sequence located at positions 91 to 135 from the 5'-terminal end of exon 2 in the mouse myostatin gene), SEQ ID NO: 345 (a nucleotide sequence located at positions 121 to 155 from the 5'-terminal end of exon 2 in the mouse myostatin gene) and SEQ ID NO: 346 (a nucleotide sequence located at positions 151 to 210 from the 5'-terminal end of exon 2 in the mouse myostatin gene), SEQ ID NO: 347 (a nucleotide sequence located at positions 196 to 233 from the 5'-terminal end of exon 2 in the mouse myostatin gene), SEQ ID NO: 364 (a nucleotide sequence located at positions 266 to 295 from the 5'-terminal end of exon 2 in the mouse myostatin gene), SEQ ID NO: 348 (a nucleotide sequence located at positions 326 to 374 from the 5'-terminal end of exon 2 in the mouse myostatin gene), SEQ ID NO: 355 (a nucleotide sequence located at positions 1 to 18 from the 5'-terminal end of exon 2 in the mouse myostatin gene), SEQ ID NO: 356 (a nucleotide sequence located at positions 116 to 131 from the 5'-terminal end of exon 2 in the mouse myostatin gene), SEQ ID NO: 357 (a nucleotide sequence located at positions 130 to 140 from the 5'-terminal end of exon 2 in the mouse myostatin gene), SEQ ID NO: 358 (a nucleotide sequence located at positions 160 to 206 from the 5'-terminal end of exon 2 in the mouse myostatin gene), SEQ ID NO: 359 (a nucleotide sequence located at positions 211 to 255 from the 5'-terminal end of exon 2 in the mouse myostatin gene), SEQ ID NO: 365 (a nucleotide sequence located at positions 271 to 282 from the 5'-terminal end of exon 2 in the mouse myostatin gene) and SEQ ID NO: 366 (a nucleotide sequence located at positions 341 to 365 from the 5'-terminal end of exon 2 in the mouse myostatin gene), as calculated by the homology search software BLAST using default parameters.

It should be noted that the identity of nucleotide sequences can be determined by BLAST (Basic Local Alignment Search Tool) (Proc. Natl. Acad. Sci. USA 872264-2268, 1990; Proc. Natl. Acad. Sci. USA 90: 5873, 1993). If BLAST is used, default parameters in each program may be used.

The unit oligomers (hereinafter also simply referred to as "units") shown in (c) to (f) above each have a size of 7 to 15 bases in length, preferably 8 to 15 bases in length, 9 to 15 bases in length, 10 to 15 bases in length, 10 to 14 bases in length, 10 to 13 bases in length or 11 to 13 bases in length. The respective units shown in (c) to (f) above may be of the same or different size.

In the above antisense oligomer (c), either of two units selected from the group consisting of the above units (c-1) to (c-6) may be located at the 5'-terminal side.

In the above antisense oligomer (d), either of two units selected from the group consisting of the above units (d-1) to (d-7) may be located at the 5'-terminal side.

In the above antisense oligomer (e), either of two units selected from the group consisting of the above units (e-1) to (e-6) may be located at the 5'-terminal side.

In the above antisense oligomer (f), either of two units selected from the group consisting of the above units (f-1) to (f-7) may be located at the 5'-terminal side.

As used here, the term "connected" is intended to mean that two units are directly connected to each other. Namely, when two units are connected, it means that the 3'-terminal end of the unit located at the 5'-terminal side and the 5'-terminal end of the unit located at the 3'-terminal side form a phosphate bond or any of the following groups:

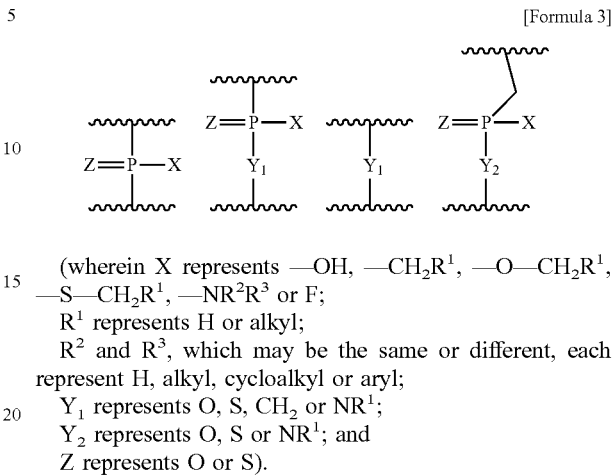

[Formula 3]

(wherein X represents —OH, —CH$_2$R$^1$, —O—CH$_2$R$^1$, —S—CH$_2$R$^1$, —NR$^2$R$^3$ or F;
R$^1$ represents H or alkyl;
R$^2$ and R$^3$, which may be the same or different, each represent H, alkyl, cycloalkyl or aryl;
Y$_1$ represents O, S, CH$_2$ or NR$^1$;
Y$_2$ represents O, S or NR$^1$; and
Z represents O or S).

In a preferred embodiment of the antisense oligomer A of the present invention, the above antisense oligomer (c) consists of any one nucleotide sequence selected from the group consisting of SEQ ID NO: 103 (NMS-48), SEQ ID NO: 116 (NMS-89), SEQ ID NO: 117 (NMS-90), SEQ ID NO: 120 (NMS-93), SEQ ID NO: 128 (NMS-101), SEQ ID NO: 131 (NMS-104), SEQ ID NO: 136 (NMS-113), SEQ ID NO: 137 (NMS-117), SEQ ID NO: 140 (NMS-123), SEQ ID NO: 145 (NMS-136), SEQ ID NO: 146 (NMS-139), SEQ ID NO: 147 (NMS-140), SEQ ID NO: 148 (NMS-141), SEQ ID NO: 149 (NMS-142), SEQ ID NO: 152 (NMS-145), SEQ ID NO: 155 (NMS-148), SEQ ID NO: 156 (NMS-149), SEQ ID NO: 157 (NMS-150), SEQ ID NO: 159 (NMS-152), SEQ ID NO: 162 (NMS-156), SEQ ID NO: 163 (NMS-157), SEQ ID NO: 165 (NMS-162), SEQ ID NO: 166 (NMS-163), SEQ ID NO: 167 (NMS-164), SEQ ID NO: 168 (NMS-166), SEQ ID NO: 169 (NMS-167), SEQ ID NO: 170 (NMS-168), SEQ ID NO: 171 (NMS-169), SEQ ID NO: 176 (NMS-174), SEQ ID NO: 177 (NMS-175), SEQ ID NO: 178 (NMS-176), SEQ ID NO: 179 (NMS-177), SEQ ID NO: 180 (NMS-178), SEQ ID NO: 183 (NMS-181), SEQ ID NO: 187 (NMS-185), SEQ ID NO: 189 (NMS-188), SEQ ID NO: 190 (NMS-189), SEQ ID NO: 191 (NMS-190), SEQ ID NO: 192 (NMS-191), SEQ ID NO: 193 (NMS-192), SEQ ID NO: 196 (NMS-195), SEQ ID NO: 199 (NMS-198), SEQ ID NO: 200 (NMS-199), SEQ ID NO: 201 (NMS-200), SEQ ID NO: 203 (NMS-202), SEQ ID NO: 204 (NMS-203), SEQ ID NO: 206 (NMS-206), SEQ ID NO: 208 (NMS-208), SEQ ID NO: 212 (NMS-212), SEQ ID NO: 213 (NMS-213), SEQ ID NO: 214 (NMS-214), SEQ ID NO: 215 (NMS-215), SEQ ID NO: 217 (NMS-217), SEQ ID NO: 225 (NMS-225), SEQ ID NO: 226 (NMS-228), SEQ ID NO: 228 (NMS-230), SEQ ID NO: 229 (NMS-231), SEQ ID NO: 231 (NMS-233), SEQ ID NO: 232 (NMS-234), SEQ ID NO: 233 (NMS-235), SEQ ID NO: 236 (NMS-240), SEQ ID NO: 237 (NMS-241), SEQ ID NO: 240 (NMS-244), SEQ ID NO: 243 (NMS-247), SEQ ID NO: 244 (NMS-248), SEQ ID NO: 245 (NMS-249), SEQ ID NO: 246 (NMS-250), SEQ ID NO: 247 (NMS-251), SEQ ID NO: 248 (NMS-252), SEQ ID NO: 252 (NMS-256), SEQ ID NO: 261 (NMS-272), SEQ ID NO: 273 (NMS-284), SEQ ID NO: 274 (NMS-285), SEQ ID NO: 275 (NMS-286) and SEQ ID NO: 277 (NMS-297).

In another preferred embodiment of the antisense oligomer A of the present invention, the above antisense oligomer (d) consists of any one nucleotide sequence selected from the group consisting of SEQ ID NO: 95

(NMS-38), SEQ ID NO: 96 (NMS-39), SEQ ID NO: 107 (NMS-66), SEQ ID NO: 223 (NMS-223), SEQ ID NO: 234 (NMS-238), SEQ ID NO: 235 (NMS-239), SEQ ID NO: 242 (NMS-246), SEQ ID NO: 249 (NMS-253), SEQ ID NO: 250 (NMS-254), SEQ ID NO: 251 (NMS-255), SEQ ID NO: 257 (NMS-268), SEQ ID NO: (NMS-280), SEQ ID NO: (NMS-281), SEQ ID NO: (NMS-282), SEQ ID NO: (NMS-288), SEQ ID NO: (NMS-289), SEQ ID NO: (NMS-290), SEQ ID NO: (NMS-292), SEQ ID NO: (NMS-293), SEQ ID NO: (NMS-294), SEQ ID NO: (NMS-295), SEQ ID NO: (NMS-298), SEQ ID NO: (NMS-299), SEQ ID NO: (NMS-300), SEQ ID NO: (NMS-302) and SEQ ID NO: (NMS-303).

In a particularly preferred embodiment of the antisense oligomer A of the present invention, the above antisense oligomer (c) or (e) consists of any one nucleotide sequence selected from the group consisting of SEQ ID NO: 171 (NMS-169), SEQ ID NO: 192 (NMS-191), SEQ ID NO: 245 (NMS-249) and SEQ ID NO: 231 (NMS-233).

The expression "allowing exon 2 skipping in the myostatin gene" is intended to mean that upon binding the antisense oligomer A of the present invention to a transcript (e.g., pre-mRNA) of the human myostatin gene, the transcript is spliced to delete the whole or a part of exon 2 to thereby form mature mRNA which encodes mutant myostatin lacking the function of myostatin.

The antisense oligomer A of the present invention does not necessarily have a nucleotide sequence which is 100% complementary to a target sequence, as long as it allows exon 2 skipping in the myostatin gene. For example, the oligomer B of the present invention may contain non-complementary bases (e.g., 1 to 3 bases, 1 or 2 bases, or a single base) to the target sequence.

The term "binding" is used here to mean that once the antisense oligomer A of the present invention has been mixed with a transcript of the myostatin gene, both will be hybridized with each other under physiological conditions to form a duplex. The expression "under physiological conditions" is used here to mean conditions adjusted to mimic in vivo pH, salt composition and temperature, as exemplified by conditions of 25° C. to 40° C., preferably 37° C., pH 5 to 8, preferably pH 7.4, and a sodium chloride concentration of 150 mM.

The efficiency of skipping is as described later.

The antisense oligomer A of the present invention may be an oligonucleotide, a morpholino oligomer or a peptide nucleic acid oligomer. Such an oligonucleotide, a morpholino oligomer or a peptide nucleic acid oligomer is as described later.

1.2. Antisense Oligomer B of the Present Invention

The antisense oligomer B of the present invention is any one antisense oligomer selected from the group consisting of (A) to (H) shown below, or a pharmaceutically acceptable salt or hydrate thereof:

(A) an antisense oligomer consisting of a nucleotide sequence complementary to a nucleotide sequence of contiguous 14 to 30 bases in length selected from a nucleotide sequence located at positions −10 to 45 from the 5'-terminal end of exon 2 in the human myostatin gene;
(B) an antisense oligomer consisting of a nucleotide sequence complementary to a nucleotide sequence of contiguous 14 to 30 bases in length selected from a nucleotide sequence located at positions 91 to 145 from the 5'-terminal end of exon 2 in the human myostatin gene;
(C) an antisense oligomer consisting of a nucleotide sequence complementary to a nucleotide sequence of contiguous 14 to 30 bases in length selected from a nucleotide sequence located at positions 146 to 180 from the 5'-terminal end of exon 2 in the human myostatin gene;
(D) an antisense oligomer consisting of a nucleotide sequence complementary to a nucleotide sequence of contiguous 14 to 30 bases in length selected from a nucleotide sequence located at positions 331 to 374 from the 5'-terminal end of exon 2 in the human myostatin gene;
(E) an antisense oligomer consisting of a nucleotide sequence complementary to a nucleotide sequence of contiguous 14 to 30 bases in length selected from a nucleotide sequence located at positions −10 to 31 from the 5'-terminal end of exon 2 in the mouse myostatin gene;
(F) an antisense oligomer consisting of a nucleotide sequence complementary to a nucleotide sequence of contiguous 14 to 30 bases in length selected from a nucleotide sequence located at positions 111 to 162 from the 5'-terminal end of exon 2 in the mouse myostatin gene;
(G) an antisense oligomer consisting of a nucleotide sequence complementary to a nucleotide sequence of contiguous 14 to 30 bases in length selected from a nucleotide sequence located at positions 166 to 195 from the 5'-terminal end of exon 2 in the mouse myostatin gene; and
(H) an antisense oligomer consisting of a nucleotide sequence complementary to a nucleotide sequence of contiguous 14 to 30 bases in length selected from a nucleotide sequence located at positions 331 to 374 from the 5'-terminal end of exon 2 in the mouse myostatin gene.

In a more preferred embodiment, the antisense oligomer B of the present invention is any one antisense oligomer selected from the group consisting of (I) to (L) shown below, or a pharmaceutically acceptable salt or hydrate thereof:
(I) an antisense oligomer consisting of a nucleotide sequence complementary to a nucleotide sequence of contiguous 14 to 30 bases in length selected from a nucleotide sequence located at positions −10 to 31 from the 5'-terminal end of exon 2 in the human myostatin gene;
(J) an antisense oligomer consisting of a nucleotide sequence complementary to a nucleotide sequence of contiguous 14 to 30 bases in length selected from a nucleotide sequence located at positions 111 to 140 from the 5'-terminal end of exon 2 in the human myostatin gene, wherein the 3'-terminal base of the nucleotide sequence of 14 to 30 bases in length is a base located at position 140 from the 5'-terminal end of said exon 2;
(K) an antisense oligomer consisting of a nucleotide sequence complementary to a nucleotide sequence of contiguous 14 to 30 bases in length selected from a nucleotide sequence located at positions 146 to 180 from the 5'-terminal end of exon 2 in the human myostatin gene; and
(L) an antisense oligomer consisting of a nucleotide sequence complementary to a nucleotide sequence of contiguous 14 to 30 bases in length selected from a nucleotide sequence located at positions 331 to 374 from the 5'-terminal end of exon 2 in the human myostatin gene.

In the antisense oligomer B of the present invention, the term "gene" is intended to include not only a genomic gene, but also cDNA, precursor mRNA, and mRNA. The gene is preferably precursor mRNA, i.e., pre-mRNA.

Pre-mRNA transcribed from the myostatin gene contains three exons and two introns in the order of (5'-terminal end) exon 1, intron 1, exon 2, intron 2 and exon 3 (3'-terminal end). Pre-mRNA is spliced to generate mature mRNA. The nucleotide sequences of the human and mouse wild-type myostatin genes are known (RefSeq Accession No. NM_005259 (human) and RefSeq Accession No. NM_010834 (mouse)). The nucleotide sequence of exon 2 in the wild-type myostatin gene is as shown below:
    exon 2 (human): SEQ ID NO: 323; and
    exon 2 (mouse): SEQ ID NO: 324.

A nucleotide sequence located at position −10 from the 5'-terminal end up to the 3'-terminal end of exon 2 (human) is shown in SEQ ID NO: 325.

A nucleotide sequence located at position −10 from the 5'-terminal end up to the 3'-terminal end of exon 2 (mouse) is shown in SEQ ID NO: 326.

In the above antisense oligomer (A), the "nucleotide sequence located at positions −10 to 45 from the 5'-terminal end of exon 2 in the human myostatin gene" is shown in SEQ ID NO: 327.

In the above antisense oligomer (B), the "nucleotide sequence located at positions 91 to 145 from the 5'-terminal end of exon 2 in the human myostatin gene" is shown in SEQ ID NO: 328.

In the above antisense oligomer (C), the "nucleotide sequence located at positions 146 to 180 from the 5'-terminal end of exon 2 in the human myostatin gene" is shown in SEQ ID NO: 329.

In the above antisense oligomer (D), the "nucleotide sequence located at positions 331 to 374 from the 5'-terminal end of exon 2 in the human myostatin gene" is shown in SEQ ID NO: 330.

In the above antisense oligomer (E), the "nucleotide sequence located at positions −10 to 31 from the 5'-terminal end of exon 2 in the mouse myostatin gene" is shown in SEQ ID NO: 331.

In the above antisense oligomer (F), the "nucleotide sequence located at positions 111 to 162 from the 5'-terminal end of exon 2 in the mouse myostatin gene" is shown in SEQ ID NO: 332.

In the above antisense oligomer (G), the "nucleotide sequence located at positions 166 to 195 from the 5'-terminal end of exon 2 in the mouse myostatin gene" is shown in SEQ ID NO: 333.

In the above antisense oligomer (H), the "nucleotide sequence located at positions 331 to 374 from the 5'-terminal end of exon 2 in the mouse myostatin gene" is shown in SEQ ID NO: 334.

In the above antisense oligomer (I), the "nucleotide sequence located at positions −10 to 31 from the 5'-terminal end of exon 2 in the human myostatin gene" is shown in SEQ ID NO: 335.

In the above antisense oligomer (J), the "nucleotide sequence located at positions 111 to 140 from the 5'-terminal end of exon 2 in the human myostatin gene" is shown in SEQ ID NO: 336.

In the above antisense oligomer (K), the "nucleotide sequence located at positions 146 to 180 from the 5'-terminal end of exon 2 in the human myostatin gene" is shown in SEQ ID NO: 362.

In the above antisense oligomer (L), the "nucleotide sequence located at positions 331 to 374 from the 5'-terminal end of exon 2 in the human myostatin gene" is shown in SEQ ID NO: 363.

The antisense oligomer B of the present invention has now been prepared to cause exon 2 skipping in the myostatin gene with the aim of modifying a protein encoded by the myostatin gene into a mutant protein lacking the function of myostatin. The "function of myostatin" refers to, for example, the function or activity to negatively control skeletal muscle mass. Thus, exon 2 in the myostatin gene to be skipped by the antisense oligomer B of the present invention includes not only wild-type, but also mutated forms.

More specifically, mutated exon 2 in the myostatin gene or a portion thereof is a polynucleotide shown in (a) or (b) below:

(a) a polynucleotide hybridizable under stringent conditions with a polynucleotide consisting of a nucleotide sequence complementary to any nucleotide sequence selected from the group consisting of SEQ ID NO: 323 (exon 2 in the human myostatin gene), SEQ ID NO: 325 (a nucleotide sequence located at position −10 from the 5'-terminal end up to the 3'-terminal end of exon 2 in the human myostatin gene), SEQ ID NO: 327 (a nucleotide sequence located at positions −10 to 45 from the 5'-terminal end of exon 2 in the human myostatin gene), SEQ ID NO: 328 (a nucleotide sequence located at positions 91 to 145 from the 5'-terminal end of exon 2 in the human myostatin gene), SEQ ID NO: 329 (a nucleotide sequence located at positions 146 to 180 from the 5'-terminal end of exon 2 in the human myostatin gene), SEQ ID NO: 330 (a nucleotide sequence located at positions 331 to 374 from the 5'-terminal end of exon 2 in the human myostatin gene), SEQ ID NO: 335 (a nucleotide sequence located at positions −10 to 31 from the 5'-terminal end of exon 2 in the human myostatin gene), SEQ ID NO: 336 (a nucleotide sequence located at positions 111 to 140 from the 5'-terminal end of exon 2 in the human myostatin gene), SEQ ID NO: 362 (a nucleotide sequence located at positions 146 to 180 from the 5'-terminal end of exon 2 in the human myostatin gene), SEQ ID NO: 363 (a nucleotide sequence located at positions 331 to 374 from the 5'-terminal end of exon 2 in the human myostatin gene), SEQ ID NO: 324 (exon 2 in the mouse myostatin gene), SEQ ID NO: 326 (a nucleotide sequence located at position −10 from the 5'-terminal end up to the 3'-terminal end of exon 2 in the mouse myostatin gene), SEQ ID NO: 331 (a nucleotide sequence located at positions −10 to 31 from the 5'-terminal end of exon 2 in the mouse myostatin gene), SEQ ID NO: 332 (a nucleotide sequence located at positions 111 to 162 from the 5'-terminal end of exon 2 in the mouse myostatin gene), SEQ ID NO: 333 (a nucleotide sequence located at positions 166 to 195 from the 5'-terminal end of exon 2 in the mouse myostatin gene) and SEQ ID NO: 334 (a nucleotide sequence located at positions 331 to 374 from the 5'-terminal end of exon 2 in the mouse myostatin gene); or (b) a polynucleotide consisting of a nucleotide sequence sharing an identity of 90% or more with any nucleotide sequence selected from the group consisting of SEQ ID NO: 323 (exon 2 in the human myostatin gene), SEQ ID NO: 325 (a nucleotide sequence located at position −10 from the 5'-terminal end up to the 3'-terminal end of exon 2 in the human myostatin gene), SEQ ID NO: 327 (a nucleotide sequence located at positions −10 to 45 from the 5'-terminal end of exon 2 in the human myostatin gene), SEQ ID NO: 328 (a nucleotide sequence located at positions 91 to 145 from the 5'-terminal end of exon 2 in the human myostatin gene), SEQ ID NO: 329 (a nucleotide sequence located at positions 146 to 180 from the 5'-terminal end of exon 2 in the human myostatin gene), SEQ ID NO: 330 (a nucleotide sequence located at positions 331 to 374 from the 5'-terminal end of exon 2 in the human myostatin gene), SEQ ID NO: 335 (a nucleotide sequence located at positions −10 to 31 from the 5'-terminal end of exon 2 in the human myostatin gene), SEQ ID NO: 336 (a nucleotide sequence located at positions 111 to 140 from the 5'-terminal end of exon 2 in the human myostatin gene), SEQ ID NO: 362 (a nucleotide sequence located at positions 146 to 180 from the 5'-terminal end of exon 2 in the human myostatin gene), SEQ ID NO: 363 (a nucleotide sequence located at positions 331 to 374 from the 5'-terminal end of exon 2 in the human myostatin gene), SEQ ID NO: 324 (exon 2 in the mouse myostatin gene), SEQ ID NO: 326 (a nucleotide sequence located at position −10 from the 5'-terminal end up to the 3'-terminal end of exon 2 in the mouse myostatin gene), SEQ ID NO: 331 (a nucleotide sequence located at positions −10 to 31 from the 5'-terminal end of exon 2 in the mouse myostatin gene), SEQ ID NO: 332 (a nucleotide sequence located at positions 111 to 162 from the 5'-terminal end of exon 2 in the mouse myostatin gene), SEQ ID NO: 333 (a nucleotide sequence located at positions 166 to 195 from the 5'-terminal end of exon 2 in the mouse myostatin gene) and SEQ ID NO: 334 (a nucleotide sequence located at positions 331 to 374 from the 5'-terminal end of exon 2 in the mouse myostatin gene).

As used herein, the term "polynucleotide" is intended to mean DNA or RNA.

As used herein, the expression "nucleotide sequence complementary" is not limited only to a nucleotide sequence forming Watson-Crick pairs with a target nucleotide sequence and also includes nucleotide sequences forming wobble base pairs with a target nucleotide sequence. In this regard, a Watson-Crick pair is intended to mean a base pair which forms hydrogen bonding between adenine and thymine, between adenine and uracil or between guanine and cytosine, whereas a wobble base pair is intended to mean a base pair which forms hydrogen bonding between guanine and uracil, between inosine and uracil, between inosine and adenine or between inosine and cytosine. Moreover, such a "nucleotide sequence complementary" does not necessarily have 100% complementarity to a target nucleotide sequence and may contain non-complementary bases (e.g., 1 to 3 bases, 1 or 2 bases, or a single base) to the target nucleotide sequence.

As used herein, the expression "polynucleotide hybridizable under stringent conditions" is intended to mean, for example, an antisense oligomer that can be obtained by means of colony hybridization, plaque hybridization, Southern hybridization or other hybridization techniques using, as a probe, the whole or a part of a polynucleotide consisting of a nucleotide sequence complementary to any nucleotide sequence selected from the group consisting of SEQ ID NO: 323 (exon 2 in the human myostatin gene), SEQ ID NO: 325 (a nucleotide sequence located at position −10 from the 5'-terminal end up to the 3'-terminal end of exon 2 in the human myostatin gene), SEQ ID NO: 327 (a nucleotide sequence located at positions −10 to 45 from the 5'-terminal end of exon 2 in the human myostatin gene), SEQ ID NO: 328 (a nucleotide sequence located at positions 91 to 145 from the 5'-terminal end of exon 2 in the human myostatin gene), SEQ ID NO: 329 (a nucleotide sequence located at positions 146 to 180 from the 5'-terminal end of exon 2 in the human myostatin gene), SEQ ID NO: 330 (a nucleotide sequence located at positions 331 to 374 from the 5'-terminal end of exon 2 in the human myostatin gene), SEQ ID NO: 335 (a nucleotide sequence located at positions −10 to 31 from the 5'-terminal end of exon 2 in the human myostatin gene), SEQ ID NO: 336 (a nucleotide sequence located at positions 111 to 140 from the 5'-terminal end of exon 2 in the human myostatin gene), SEQ ID NO: 362 (a nucleotide sequence located at positions 146 to 180 from the 5'-terminal end of exon 2 in the human myostatin gene), SEQ ID NO: 363 (a nucleotide sequence located at positions 331 to 374 from the 5'-terminal end of exon 2 in the human myostatin gene), SEQ ID NO: 324 (exon 2 in the mouse myostatin gene), SEQ ID NO: 326 (a nucleotide sequence located at position −10 from the 5'-terminal end up to the 3'-terminal end of exon 2 in the mouse myostatin gene), SEQ ID NO: 331 (a nucleotide sequence located at positions −10 to 31 from the 5'-terminal end of exon 2 in the mouse myostatin gene), SEQ ID NO: 332 (a nucleotide sequence located at positions 111 to 162 from the 5'-terminal end of exon 2 in the mouse myostatin gene), SEQ ID NO: 333 (a nucleotide sequence located at positions 166 to 195 from the 5'-terminal end of exon 2 in the mouse myostatin gene) and SEQ ID NO: 334 (a nucleotide sequence located at positions 331 to 374 from the 5'-terminal end of exon 2 in the mouse myostatin gene). For hybridization, it is possible to use techniques as described in, e.g., "Sambrook & Russell, Molecular Cloning: A Laboratory Manual (Fourth Edition), Cold Spring Harbor, Laboratory Press 2012" and "Ausubel, Current Protocols in Molecular Biology, John Wiley & Sons 1987-1997."

As used herein, the term "stringent conditions" may be any of low stringent conditions, moderately stringent conditions and high stringent conditions. "Low stringent conditions" refer to, for example, conditions of 5×SSC, 5×Denhardt's solution, 0.5% SDS, 50% formamide and 32° C. Likewise, "moderately stringent conditions" refer to, for example, conditions of 5×SSC, 5×Denhardt's solution, 0.5% SDS, 50% formamide and 42° C. or conditions of 5×SSC, 1% SDS, 50 mM Tris-HCl (pH 7.5), 50% formamide and 42° C. "High stringent conditions" refer to, for example, conditions of (1) 5×SSC, 5×Denhardt's solution, 0.5% SDS, 50% formamide and 50° C., (2) 0.2×SSC, 0.1% SDS and 60° C., (3) 0.2×SSC, 0.1% SDS and 62° C., (4) 0.2×SSC, 0.1% SDS and 65° C., or (5) 0.1×SSC, 0.1% SDS and 65° C., but are not limited thereto. Under these conditions, it can be expected that an antisense oligomer having a higher sequence identity is more efficiently obtained at a higher temperature. However, the stringency of hybridization would be affected by a plurality of factors, including temperature, probe concentration, probe length, ionic strength, reaction time, salt concentration and so on. Those skilled in the art would be able to achieve the same stringency by selecting these factors as appropriate.

It should be noted that if a commercially available kit is used for hybridization, an Alkphos Direct Labelling and Detection System (GE Healthcare) may be used for this purpose, by way of example. In this case, hybridization may be accomplished in accordance with the protocol attached to the kit, i.e., a membrane may be incubated overnight with a labeled probe and then washed with a primary washing buffer containing 0.1% (w/v) SDS under conditions of 55° C. to detect the hybridized antisense oligomer. Alternatively, if a commercially available reagent (e.g., PCR labeling mix (Roche Diagnostics)) is used for digoxigenin (DIG) labeling of a probe during probe preparation based on the whole or a part of a nucleotide sequence complementary to any nucleotide sequence selected from the group consisting of SEQ ID NO: 323 (exon 2 in the human myostatin gene), SEQ ID NO: 325 (a nucleotide sequence located at position −10 from the 5'-terminal end up to the 3'-terminal end of exon 2 in the human myostatin gene), SEQ ID NO: 327 (a nucleotide sequence located at positions −10 to 45 from the 5'-terminal end of exon 2 in the human myostatin gene), SEQ ID NO: 328 (a nucleotide sequence located at positions 91 to 145 from the 5'-terminal end of exon 2 in the human myostatin gene), SEQ ID NO: 329 (a nucleotide sequence located at positions 146 to 180 from the 5'-terminal end of exon 2 in the human myostatin gene), SEQ ID NO: 330 (a nucleotide sequence located at positions 331 to 374 from the 5'-terminal end of exon 2 in the human myostatin gene), SEQ ID NO: 335 (a nucleotide sequence located at positions −10 to 31 from the 5'-terminal end of exon 2 in the human myostatin gene), SEQ ID NO: 336 (a nucleotide sequence located at positions 111 to 140 from the 5'-terminal end of exon 2 in the human myostatin gene), SEQ ID NO: 362 (a nucleotide sequence located at positions 146 to 180 from the 5'-terminal end of exon 2 in the human myostatin gene), SEQ ID NO: 363 (a nucleotide sequence located at positions 331 to 374 from the 5'-terminal end of exon 2 in the human myostatin gene), SEQ ID NO: 324 (exon 2 in the mouse myostatin gene), SEQ ID NO: 326 (a nucleotide sequence located at position −10 from the 5'-terminal end up to the 3'-terminal end of exon 2 in the mouse myostatin gene), SEQ ID NO: 331 (a nucleotide sequence located at positions −10 to 31 from the 5'-terminal end of exon 2 in the mouse myostatin gene), SEQ ID NO: 332 (a nucleotide sequence located at positions 111 to 162 from the 5'-terminal end of exon 2 in the mouse myostatin gene), SEQ ID NO: 333 (a nucleotide sequence located at positions 166 to 195 from the 5'-terminal end of exon 2 in the mouse myostatin gene) and SEQ ID NO: 334 (a nucleotide sequence located at positions 331 to 374 from the 5'-terminal end of exon 2 in the mouse myostatin gene), a DIG nucleic acid detection kit (Roche Diagnostics) may be used for detection of hybridization.

In addition to those listed above, other hybridizable antisense oligomers include polynucleotides sharing an identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with SEQ ID NO: 323 (exon 2 in the human myostatin gene), SEQ ID NO: 325 (a nucleotide sequence located at position −10 from the 5'-terminal end up to the 3'-terminal end of exon 2 in the human myostatin gene), SEQ ID NO: 327 (a nucleotide sequence located at positions −10 to 45 from the 5'-terminal end of exon 2 in the human myostatin gene), SEQ ID NO: 328 (a nucleotide sequence located at positions 91 to 145 from the 5'-terminal end of exon 2 in the human myostatin gene), SEQ ID NO: 329 (a nucleotide sequence located at positions 146 to 180 from the 5'-terminal end of exon 2 in the human myostatin gene), SEQ ID NO: 330 (a nucleotide sequence located at positions 331 to 374 from the 5'-terminal end of exon 2 in the human myostatin gene), SEQ ID NO: 335 (a nucleotide sequence located at positions −10 to 31 from the 5'-terminal end of exon 2 in the human myostatin gene), SEQ ID NO: 336 (a nucleotide sequence located at positions 111 to 140 from the 5'-terminal end of exon 2 in the human myostatin gene), SEQ ID NO: 362 (a nucleotide sequence located at positions 146 to 180 from the 5'-terminal end of exon 2 in the human myostatin gene), SEQ ID NO: 363 (a nucleotide sequence located at positions 331 to 374 from the 5'-terminal end of exon 2 in the human myostatin gene), SEQ ID NO: 324 (exon 2 in the mouse myostatin gene), SEQ ID NO: 326 (a nucleotide sequence located at position −10 from the 5'-terminal end up to the 3'-terminal end of exon 2 in the mouse myostatin gene), SEQ ID NO: 331 (a nucleotide sequence located at positions −10 to 31 from the 5'-terminal end of exon 2 in the mouse myostatin gene), SEQ ID NO: 332 (a nucleotide sequence located at positions 111 to 162 from the 5'-terminal end of exon 2 in the mouse myostatin gene), SEQ ID NO: 333 (a nucleotide sequence located at positions 166 to 195 from the 5' end of exon 2 in the mouse myostatin gene) and SEQ ID NO: 334 (a nucleotide sequence located at positions 331 to 374 from the 5'-terminal end of exon 2 in the mouse myostatin gene), as calculated by the homology search software BLAST using default parameters.

It should be noted that the identity of nucleotide sequences can be determined by BLAST (Basic Local Alignment Search Tool) (Proc. Natl. Acad. Sci. USA 872264-2268, 1990; Proc. Natl. Acad. Sci. USA 90: 5873, 1993). If BLAST is used, default parameters in each program may be used.

The expression "allowing exon 2 skipping in the myostatin gene" is intended to mean that upon binding the antisense oligomer B of the present invention to a transcript (e.g., pre-mRNA) of the human myostatin gene, the transcript is spliced to delete the whole or a part of exon 2 to thereby form mature mRNA which encodes mutant myostatin lacking the function of myostatin.

The antisense oligomer B of the present invention does not necessarily have a nucleotide sequence which is 100% complementary to a target sequence, as long as it allows exon 2 skipping in the myostatin gene. For example, the antisense oligomer B of the present invention may contain non-complementary bases (e.g., 1 to 3 bases, 1 or 2 bases, or a single base) to the target sequence.

The term "binding" is used here to mean that once the antisense oligomer B of the present invention has been mixed with a transcript of the myostatin gene, both will be hybridized with each other under physiological conditions to form a duplex. The expression "under physiological conditions" is used here to mean conditions adjusted to mimic in vivo pH, salt composition and temperature, as exemplified by conditions of 25° C. to 40° C., preferably 37° C., pH 5 to 8, preferably pH 7.4, and a sodium chloride concentration of 150 mM.

In another preferred embodiment of the antisense oligomer B of the present invention, the above antisense oligomer (A) consists of any one nucleotide sequence selected from the group consisting of SEQ ID NO: 13 (NMS-17), SEQ ID NO: 76 (NMS-138), SEQ ID NO: 68 (NMS-120), SEQ ID NO: 75 (NMS-137), SEQ ID NO: 51 (NMS-76), SEQ ID NO: 52 (NMS-79), SEQ ID NO: 54 (NMS-81), SEQ ID NO: 55 (NMS-82), SEQ ID NO: 56 (NMS-83), SEQ ID NO: 53 (NMS-80), SEQ ID NO: 33 (NMS-49), SEQ ID NO: 63 (NMS-114), SEQ ID NO: 69 (NMS-124), SEQ ID NO: 70 (NMS-125), SEQ ID NO: 61 (NMS-110), SEQ ID NO: 31 (NMS-46), SEQ ID NO: 34 (NMS-50), SEQ ID NO: 50 (NMS-75), SEQ ID NO: 45 (NMS-67) and SEQ ID NO: 64 (NMS-115).

In a preferred embodiment of the antisense oligomer B of the present invention, the above antisense oligomer (B) consists of any one nucleotide sequence selected from the group consisting of SEQ ID NO: 3 (NMS-6), SEQ ID NO: 66 (NMS-118), SEQ ID NO: 67 (NMS-119), SEQ ID NO: 28 (NMS-33), SEQ ID NO: 72 (NMS-127), SEQ ID NO: 16 (NMS-20), SEQ ID NO: 82 (NMS-187) and SEQ ID NO: 25 (NMS-30).

In another preferred embodiment of the antisense oligomer B of the present invention, the above antisense oligomer (C) consists of a nucleotide sequence shown in SEQ ID NO: 12 (NMS-16).

In another preferred embodiment of the antisense oligomer B of the present invention, the above antisense oligomer (D) consists of a nucleotide sequence shown in SEQ ID NO: 4 (NMS-7).

In yet another preferred embodiment of the antisense oligomer B of the present invention, the above antisense oligomer (E) consists of a nucleotide sequence shown in SEQ ID NO: 90 (NMS-51).

In yet another preferred embodiment of the antisense oligomer B of the present invention, the above antisense oligomer (F) consists of any one nucleotide sequence selected from the group consisting of SEQ ID NO: 91 (NMS-52), SEQ ID NO: 28 (NMS-33) and SEQ ID NO: 25 (NMS-30), SEQ ID NO: 41 (NMS-61), SEQ ID NO: 24

(NMS-29), SEQ ID NO: 42 (NMS-62), SEQ ID NO: 43 (NMS-63), SEQ ID NO: 11 (NMS-15), SEQ ID NO: 67 (NMS-119), SEQ ID NO: 80 (NMS-161) and SEQ ID NO: 82 (NMS-187).

In yet another preferred embodiment of the antisense oligomer B of the present invention, the above antisense oligomer (G) consists of a nucleotide sequence shown in SEQ ID NO: 7 (NMS-10).

In yet another preferred embodiment of the antisense oligomer B of the present invention, the above antisense oligomer (H) consists of any one nucleotide sequence selected from the group consisting of SEQ ID NO: 4 (NMS-7), SEQ ID NO: 9 (NMS-12), SEQ ID NO: 10 (NMS-14) and SEQ ID NO: 14 (NMS-18).

The efficiency of skipping is as described later.

The antisense oligomer B of the present invention may be an oligonucleotide, a morpholino oligomer or a peptide nucleic acid oligomer. Such an oligonucleotide, a morpholino oligomer or a peptide nucleic acid oligomer is as described later.

1.3. Skipping Efficiency

To confirm whether or not exon skipping was caused in the myostatin gene, the antisense oligomer of the present invention may be transfected into myostatin-expressing cells (e.g., human rhabdomyosarcoma cells) and a region around the exon in mRNA of the myostatin gene may be amplified by RT-PCR from the total RNA of the above myostatin-expressing cells, followed by nested PCR or sequencing analysis on the PCR amplification product.

The efficiency of skipping may be determined as follows: mRNA of the myostatin gene is collected from test cells and the mRNA is measured for the polynucleotide level "A" in the band with exon skipping and the polynucleotide level "B" in the band without exon skipping, followed by calculation based on these measured values of "A" and "B" according to the following equation.

Skipping efficiency (%)={$A/(A+B)$}×100

In a preferred embodiment, the antisense oligomer of the present invention causes exon skipping with an efficiency of 10% or more, 20% or more, 30% or more, 40% or more, 50% or more, 60% or more, 70% or more, 80% or more, or 90% or more.

As to the calculation of skipping efficiency, reference may be made to WO2012/029986.

1.4. Oligonucleotide, Morpholino Oligomer or Peptide Nucleic Acid Oligomer

The antisense oligomer of the present invention may be exemplified by an oligonucleotide, a morpholino oligomer or a peptide nucleic acid (PNA) oligomer, each being 14 to 30 bases in length. The antisense oligomer of the present invention is preferably 15 to 29 bases, 16 to 28 bases, 17 to 27 bases or 18 to 26 bases in length, and is preferably a morpholino oligomer.

The above oligonucleotide (hereinafter referred to as "the oligonucleotide of the present invention") is an antisense oligomer according to the present invention, whose constituent unit is a nucleotide, and such a nucleotide may be any of a ribonucleotide, a deoxyribonucleotide or a modified nucleotide.

A modified nucleotide refers to a ribonucleotide or deoxyribonucleotide whose nucleobase, sugar moiety and phosphate bond moiety are all or partly modified.

In the present invention, examples of a nucleobase include adenine, guanine, hypoxanthine, cytosine, thymine, uracil, or modified bases thereof. Such modified bases may be exemplified by pseudouracil, 3-methyluracil, dihydrouracil, 5-alkylcytosines (e.g., 5-methylcytosine), 5-alkyluracils (e.g., 5-ethyluracil), 5-halouracils (e.g., 5-bromouracil), 6-azapyrimidine, 6-alkylpyrimidines (e.g., 6-methyluracil), 2-thiouracil, 4-thiouracil, 4-acetylcytosine, 5-(carboxyhydroxymethyl)uracil, 5-carboxymethylaminomethyl-2-thiouracil, 5-carboxymethylaminomethyluracil, 1-methyladenine, 1-methylhypoxanthine, 2,2-dimethylguanine, 3-methylcytosine, 2-methyladenine, 2-methylguanine, N6-methyladenine, 7-methylguanine, 5-methoxyaminomethyl-2-thiouracil, 5-methylaminomethyluracil, 5-methylcarbonylmethyluracil, 5-methyloxyuracil, 5-methyl-2-thiouracil, 2-methylthio-N6-isopentenyladenine, uracil-5-oxyacetic acid, 2-thiocytosine, purine, 2,6-diaminopurine, 2-aminopurine, isoguanine, indole, imidazole, xanthine and so on, but are not limited thereto.

Modifications to the sugar moiety may be exemplified by modifications at the 2'-position of ribose and modifications at the other positions of sugar. Examples of modifications at the 2'-position of ribose include modifications intended to replace the —OH group at the 2'-position of ribose with OR, R, R'OR, SH, SR, $NH_2$, NHR, $NR_2$, $N_3$, CN, F, Cl, Br or I, wherein R represents alkyl or aryl, and R' represents alkylene.

Examples of modifications at the other positions of sugar include replacement of O with S at the 4'-position of ribose or deoxyribose, and bridging between 2'- and 4'-positions of sugar, as exemplified by LNAs (locked nucleic acids) or ENAs (2'-O,4'-C-ethylene-bridged nucleic acids), but are not limited thereto.

Modifications to the phosphate bond moiety may be exemplified by modifications intended to replace the phosphodiester bond with a phosphorothioate bond, a phosphorodithioate bond, an alkylphosphonate bond, a phosphoroamidate bond or a boranophosphate bond (Enya et al: Bioorganic & Medicinal Chemistry, 2008, 18, 9154-9160) (see, e.g., JP WO2006/129594 and JP WO2006/038608).

In the present invention, alkyl is preferably a linear or branched alkyl containing 1 to 6 carbon atoms. More specifically, examples include methyl, ethyl, n-propyl, isopropyl, n-butyl, isobutyl, sec-butyl, tert-butyl, n-pentyl, isopentyl, neopentyl, tert-pentyl, n-hexyl and isohexyl. Such an alkyl may be substituted with 1 to 3 substituents including halogen, alkoxy, cyano, nitro, etc.

In the present invention, cycloalkyl is preferably a cycloalkyl containing 5 to 12 carbon atoms. More specifically, examples include cyclopentyl, cyclohexyl, cycloheptyl, cyclooctyl, cyclodecyl and cyclododecyl.

In the present invention, halogens include fluorine, chlorine, bromine and iodine.

Alkoxy may be a linear or branched alkoxy containing 1 to 6 carbon atoms, as exemplified by methoxy, ethoxy, n-propoxy, isopropoxy, n-butoxy, isobutoxy, sec-butoxy, tert-butoxy, n-pentyloxy, isopentyloxy, n-hexyloxy, isohexyloxy and so on. Particularly preferred is an alkoxy containing 1 to 3 carbon atoms.

In the present invention, aryl is preferably an aryl containing 6 to 10 carbon atoms. More specifically, examples include phenyl, α-naphthyl and β-naphthyl. Particularly preferred is phenyl. Such an aryl may be substituted with 1 to 3 substituents including alkyl, halogen, alkoxy, cyano, nitro, etc.

In the present invention, alkylene is preferably a linear or branched alkylene containing 1 to 6 carbon atoms. More specifically, examples include methylene, ethylene, trimethylene, tetramethylene, pentamethylene, hexamethylene, 2-(ethyl)trimethylene and 1-(methyl)tetramethylene.

In the present invention, acyl may be a linear or branched alkanoyl or an aroyl. Examples of such an alkanoyl include formyl, acetyl, 2-methylacetyl, 2,2-dimethylacetyl, propionyl, butyryl, isobutyryl, pentanoyl, 2,2-dimethylpropionyl, hexanoyl and so on. Examples of an aroyl include benzoyl, toluoyl and naphthoyl. Such an aroyl may be substituted at any substitutable position and may be substituted with alkyl(s).

The oligonucleotide of the present invention is preferably an antisense oligomer according to the present invention, whose constituent unit is a group represented by the following general formula, in which the —OH group at the 2'-position of ribose is substituted with methoxy and the phosphate bond moiety is a phosphorothioate bond:

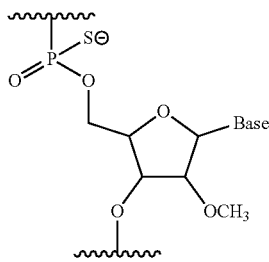

[Formula 4]

(wherein Base represents a nucleobase).

The oligonucleotide of the present invention may be readily synthesized with various automatic synthesizers (e.g., FOCUS (Aapptec), AKTA oligopilot plus 10/100 (GE Healthcare)), or alternatively, its synthesis may be entrusted to a third party (e.g., Promega, Takara, or Japan Bio Services), etc.

The morpholino oligomer of the present invention is an antisense oligomer according to the present invention, whose constituent unit is a group represented by the following general formula:

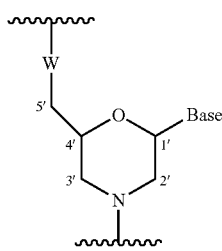

[Formula 5]

(wherein Base is the same as defined above; and
W represents a group represented by any of the following formulae:

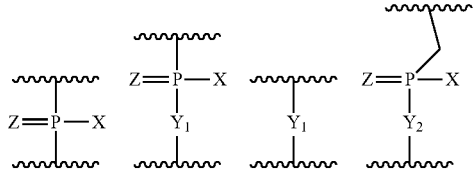

[Formula 6]

(wherein X represents —$CH_2R^1$, —O—$CH_2R^1$, —S—$CH_2R^1$, —$NR^2R^3$ or F;

$R^1$ represents H or alkyl;
$R^2$ and $R^3$, which may be the same or different, each represent H, alkyl, cycloalkyl or aryl;
$Y_1$ represents O, S, $CH_2$ or $NR^1$;
$Y_2$ represents O, S or $NR^1$; and
Z represents O or S)).

The morpholino oligomer is preferably an oligomer whose constituent unit is a group represented by the following formula (i.e., a phosphorodiamidate morpholino oligomer (hereinafter referred to as "PMO")):

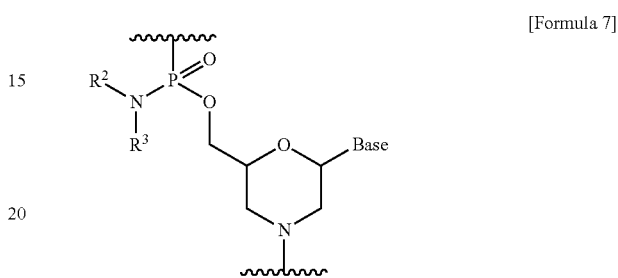

[Formula 7]

(wherein Base, $R^2$ and $R^3$ are the same as defined above).

For example, the morpholino oligomer may be prepared in accordance with WO1991/009033 or WO2009/064471. In particular, PMO may be prepared in accordance with the procedures described in WO2009/064471 or may be prepared in accordance with the procedures shown below.

[Process for PMO Preparation]

As one embodiment of PMO, a compound represented by the following general formula (I) (hereinafter referred to as PMO (I)) may be given by way of example:

[Formula 8]

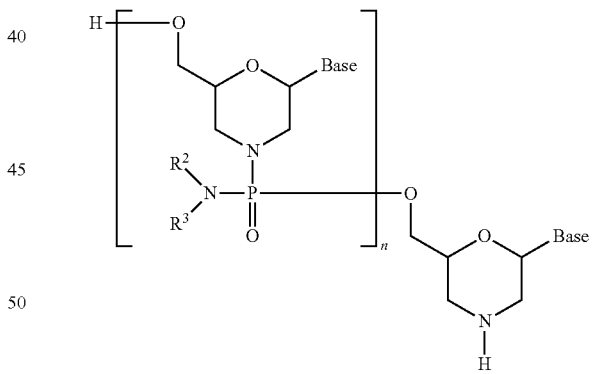

(I)

[wherein each Base, $R^2$ and $R^3$ are the same as defined above; and
n is any integer in the range of 1 to 99, preferably any integer in the range of 13 to 29, 14 to 28 or 15 to 27, 16 to 26, 17 to 25].

PMO (I) may be prepared in accordance with known procedures, for example, by conducting the operations shown in the following steps.

Compounds and reagents used in the following steps are not limited in any way as long as they are commonly used for PMO preparation.

Moreover, all the following steps may be accomplished by the liquid phase method or the solid phase method (in accordance with instruction manuals or using a commercially available solid phase automatic synthesizer). When PMO is prepared by the solid phase method, it is desirable to use an automatic synthesizer in terms of simple operation and accurate synthesis.

(1) Step A:

This is a step where a compound represented by the following general formula (II) (hereinafter referred to as compound (II)) is treated with an acid to prepare a compound represented by the following general formula (III) (hereinafter referred to as compound (III)):

[Formula 9]

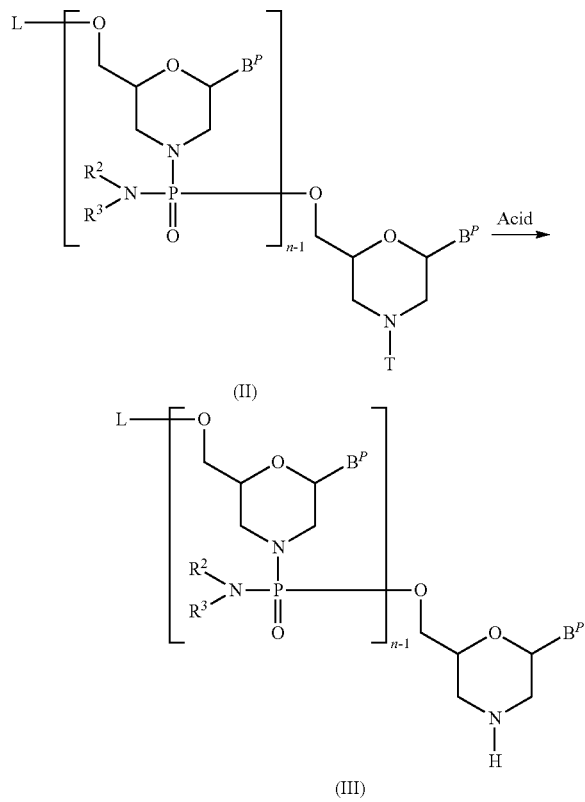

(II)

(III)

[wherein n, $R^2$ and $R^3$ are the same as defined above;
each $B^P$ independently represents a nucleobase which may be protected;
T represents a trityl group, a monomethoxytrityl group or a dimethoxytrityl group; and
L represents hydrogen, acyl or a group represented by the following general formula (IV) (hereinafter referred to as group (IV))]:

[Formula 10]

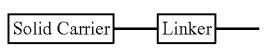

(IV)

"Nucleobases" possible for $B^P$ may be exemplified by the same "nucleobases" as listed for Base, provided that amino groups or hydroxyl groups in these nucleobases for $B^P$ may be protected.

Protecting groups for these amino groups are not limited in any way as long as they are used as protecting groups for nucleic acids. More specifically, examples include benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl, and (dimethylamino)methylene. Protecting groups for hydroxyl groups include, for example, 2-cyanoethyl, 4-nitrophenethyl, phenylsulfonylethyl, methylsulfonylethyl, trimethylsilylethyl, phenyl which may be substituted with 1 to 5 electron withdrawing groups at any substitutable position(s), diphenylcarbamoyl, dimethylcarbamoyl, diethylcarbamoyl, methylphenylcarbamoyl, 1-pyrrolidinylcarbamoyl, morpholinocarbamoyl, 4-(tert-butylcarboxy)benzyl, 4-[(dimethylamino)carboxy]benzyl, and 4-(phenylcarboxy)benzyl (see, e.g., WO2009/064471).

The "solid carrier" is not limited in any way as long as it is a carrier available for use in the solid phase reaction of nucleic acids, but it is desirable to use, for example, a carrier which (i) is sparingly soluble in reagents available for use in the synthesis of morpholino nucleic acid derivatives (e.g., dichloromethane, acetonitrile, tetrazole, N-methylimidazole, pyridine, acetic anhydride, lutidine, trifluoroacetic acid), (ii) is chemically stable against the reagents available for use in the synthesis of morpholino nucleic acid derivatives, (iii) can be chemically modified, (iv) can be loaded with desired morpholino nucleic acid derivatives, (v) has strength sufficient to withstand high pressure during processing, and (vi) has a certain range of particle size and distribution. More specifically, examples include swelling polystyrenes (e.g., aminomethyl polystyrene resin cross-linked with 1% divinylbenzene (200 to 400 mesh) (2.4 to 3.0 mmol/g) (Tokyo Chemical Industry Co., Ltd., Japan), Aminomethylated Polystyrene Resin HCl [divinylbenzene 1%, 100 to 200 mesh] (Peptide Institute, Inc., Japan)), non-swelling polystyrenes (e.g., Primer Support (GE Healthcare)), PEG chain-liked polystyrenes (e.g., $NH_2$-PEG resin (Watanabe Chemical Industries, Ltd., Japan), TentaGel resin), controlled pore glass (CPG) (e.g., a product of CPG Inc.), oxalylated controlled pore glass (see, e.g., Alul et al., Nucleic Acids Research, Vol. 19, 1527 (1991)), TentaGel support-aminopolyethylene glycol-derivatized support (see, e.g., Wright et al., Tetrahedron Letters, Vol. 34, 3373 (1993)), and a Poros-polystyrene/divinylbenzene copolymer.

As a "linker," it is possible to use a known linker which is commonly used to link a nucleic acid or a morpholino nucleic acid derivative, and examples include 3-aminopropyl, succinyl, 2,2'-diethanol sulfonyl, and a long-chain alkylamino (LCAA).

This step may be accomplished by treating compound (II) with an acid.

Examples of an "acid" available for use in this step include trifluoroacetic acid, dichloroacetic acid or trichloroacetic acid. The amount of an acid to be used is, for example, reasonably in the range of 0.1 molar equivalents to 1000 molar equivalents, preferably in the range of 1 molar equivalent to 100 molar equivalents, relative to 1 mole of compound (II).

Moreover, it is possible to use an organic amine together with the above acid. Any organic amine may be used for this purpose, and examples include triethylamine. The amount of an organic amine to be used is, for example, reasonably in the range of 0.01 molar equivalents to 10 molar equivalents, preferably in the range of 0.1 molar equivalents to 2 molar equivalents, relative to 1 mole of the acid.

In a case where an acid and an organic amine are used as a salt or mixture in this step, examples include a salt or mixture of trifluoroacetic acid and triethylamine, more specifically a mixture containing 2 equivalents of trifluoroacetic acid and 1 equivalent of triethylamine.

An acid available for use in this step may be used by being diluted with an appropriate solvent to give a concentration in the range of 0.1% to 30%. Any solvent may be used for this purpose as long as it is inert to the reaction, and examples include dichloromethane, acetonitrile, alcohols (e.g., ethanol, isopropanol, trifluoroethanol), water, or mixtures thereof.

The reaction temperature in the above reaction is, for example, preferably in the range of 10° C. to 50° C., more preferably in the range of 20° C. to 40° C., and even more preferably in the range of 25° C. to 35° C.

The reaction time will vary depending on the type of acid to be used and/or the reaction temperature, but it is generally reasonably in the range of 0.1 minutes to 24 hours, and preferably in the range of 1 minute to 5 hours.

Moreover, after completion of this step, a base may optionally be added to neutralize the acid remaining in the system. Any "base" may be used for this purpose and examples include diisopropylethylamine. Such a base may be used by being diluted with an appropriate solvent to give a concentration in the range of 0.1% (v/v) to 30% (v/v).

Any solvent may be used in this step as long as it is inert to the reaction, and examples include dichloromethane, acetonitrile, alcohols (e.g., ethanol, isopropanol, trifluoroethanol), water, or mixtures thereof. The reaction temperature is, for example, preferably in the range of 10° C. to 50° C., more preferably in the range of 20° C. to 40° C., and even more preferably in the range of 25° C. to 35° C.

The reaction time will vary depending on the type of base to be used and/or the reaction temperature, but it is generally reasonably in the range of 0.1 minutes to 24 hours, and preferably in the range of 1 minute to 5 hours.

It should be noted that compound (II) in which n=1 and L is group (IV), i.e., a compound represented by the following general formula (IIa) (hereinafter referred to as compound (IIa)) may be prepared in accordance with the following procedures:

[Formula 11]

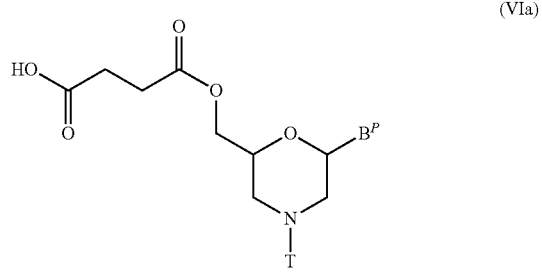

(IIa)

[wherein $B^P$, T, Linker and Solid carrier are the same as defined above].

Step 1:

This is a step where a compound represented by the following general formula (V) is treated with an acylating agent to prepare a compound represented by the following general formula (VI) (hereinafter referred to as compound (VI)):

[Formula 12]

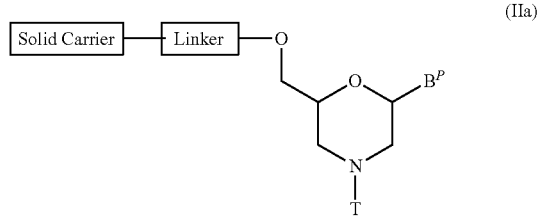

[wherein $B^P$, T and Linker are the same as defined above; and $R^4$ represents a hydroxyl group, halogen, a carboxyl group or amino].

This step may be accomplished starting from compound (V) by any known reaction for linker introduction.

In particular, a compound represented by the following general formula (VIa) may be prepared by any process known as esterification reaction with the use of compound (V) and succinic anhydride:

[Formula 13]

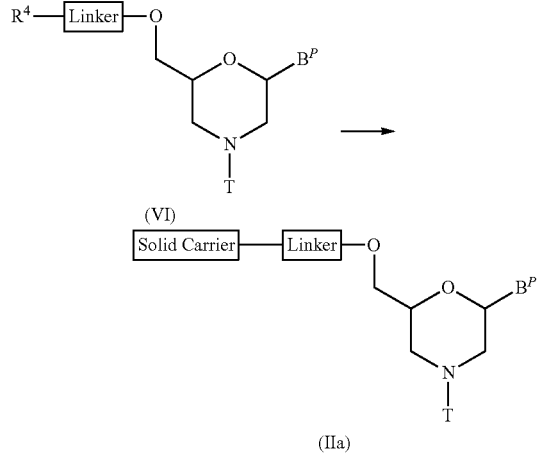

(VIa)

[wherein $B^P$ and T are the same as defined above].

Step 2:

This is a step where compound (VI) is reacted with a solid carrier by being treated with a condensing agent or the like to prepare compound (IIa):

[Formula 14]

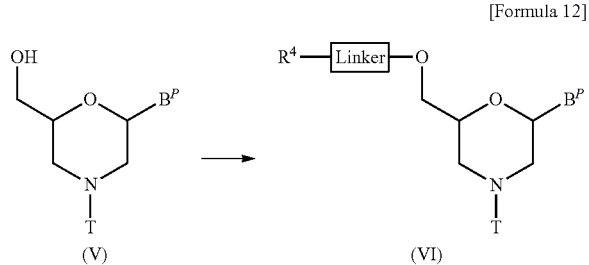

[wherein $B^P$, $R^4$, T, Linker and Solid carrier are the same as defined above].

This step may be accomplished by any process known as condensation reaction with the use of compound (VI) and a solid carrier.

Compound (II) in which n=2 to 99 (preferably any an integer in the range of 13 to 29, 14 to 28, 15 to 27, 16 to 26, or 17 to 25) and L is group (IV), i.e., a compound represented by the following general formula (IIa2) may be prepared starting from compound (IIa) by repeating desired times Steps A and B of the process for PMO preparation disclosed herein:

[Formula 15]

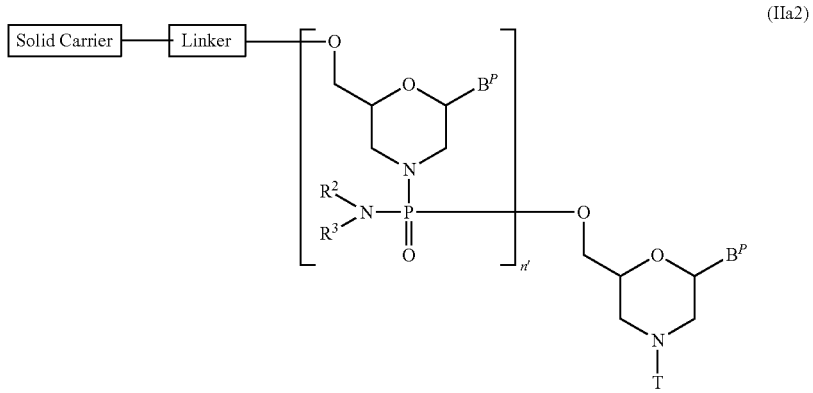

(IIa2)

[wherein $B^P$, $R^2$, $R^3$, T, Linker and Solid carrier are the same as defined above; and n' represents 1 to 98 (in particular embodiments, n' represents 1 to 28, 1 to 27, 1 to 26, 1 to 25, or 1 to 24)].

(2) Step B:

This is a step where compound (III) is treated with a morpholino monomer compound in the presence of a base to prepare a compound represented by the following general formula (VII) (hereinafter referred to as compound (VII)):

[Formula 16]

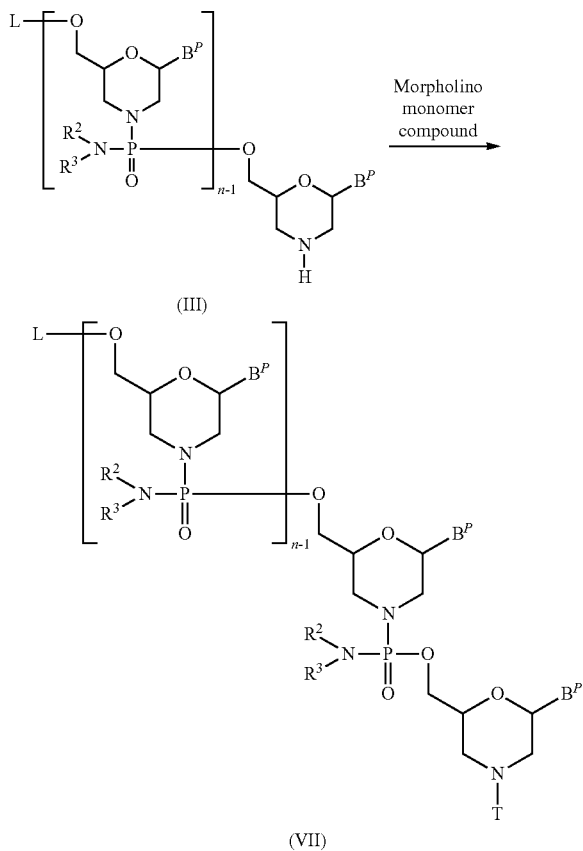

[wherein each $B^P$, L, n, $R^2$, $R^3$ and T are the same as defined above].

This step may be accomplished by treating compound (III) with a morpholino monomer compound in the presence of a base.

Such a morpholino monomer compound may be exemplified by a compound represented by the following general formula (VIII):

[Formula 17]

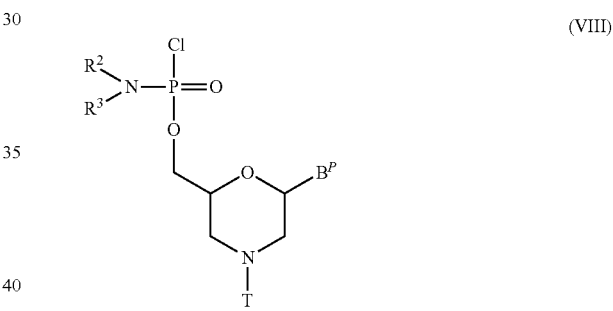

[wherein $B^P$, $R^2$, $R^3$ and T are the same as defined above].

Examples of a "base" available for use in this step include diisopropylethylamine, triethylamine or N-ethylmorpholine. The amount of a base to be used is, for example, reasonably in the range of 1 molar equivalent to 1000 molar equivalents, preferably in the range of 10 molar equivalents to 100 molar equivalents, relative to 1 mole of compound (III).

Such a morpholino monomer compound and a base available for use in this step may be used by being diluted with an appropriate solvent to give a concentration of 0.1% to 30%. Any solvent may be used for this purpose as long as it is inert to the reaction, and examples include N,N-dimethylimidazolidone, N-methylpiperidone, DMF, dichloromethane, acetonitrile, tetrahydrofuran, or mixtures thereof.

The reaction temperature is, for example, preferably in the range of 0° C. to 100° C., and more preferably in the range of 10° C. to 50° C.

The reaction time will vary depending on the type of base to be used and/or the reaction temperature, but it is generally reasonably in the range of 1 minute to 48 hours, and preferably in the range of 30 minutes to 24 hours.

Moreover, after completion of this step, an acylating agent may optionally be added. Examples of an "acylating agent" include acetic anhydride, acetic acid chloride and phenoxyacetic anhydride. Such an acylating agent may be used by being diluted with an appropriate solvent to give a concentration in the range of 0.1% to 30%, by way of example. Any solvent may be used for this purpose as long as it is inert to the reaction, and examples include dichloromethane, acetonitrile, tetrahydrofuran, alcohols (e.g., ethanol, isopropanol, trifluoroethanol), water, or mixtures thereof.

If necessary, it is possible to use a base (e.g., pyridine, lutidine, collidine, triethylamine, diisopropylethylamine, N-ethylmorpholine) together with an acylating agent. The amount of an acylating agent to be used is preferably in the range of 0.1 molar equivalents to 10000 molar equivalents, and more preferably in the range of 1 molar equivalent to 1000 molar equivalents. The amount of a base to be used is, for example, reasonably in the range of 0.1 molar equivalents to 100 molar equivalents, preferably in the range of 1 molar equivalent to 10 molar equivalents, relative to 1 mole of an acylating agent.

The reaction temperature in this reaction is preferably in the range of 10° C. to 50° C., more preferably in the range of 10° C. to 50° C., even more preferably in the range of 20° C. to 40° C., and still even more preferably in the range of 25° C. to 35° C. The reaction time will vary, e.g., depending on the type of acylating agent to be used and/or the reaction temperature, but it is generally reasonably in the range of 0.1 minutes to 24 hours, and preferably in the range of 1 minute to 5 hours.

(3) Step C:

This is a step where a deprotecting agent is used to remove the protecting groups from compound (VII) prepared in Step B, thereby preparing a compound represented by general formula (IX):

[Formula 18]

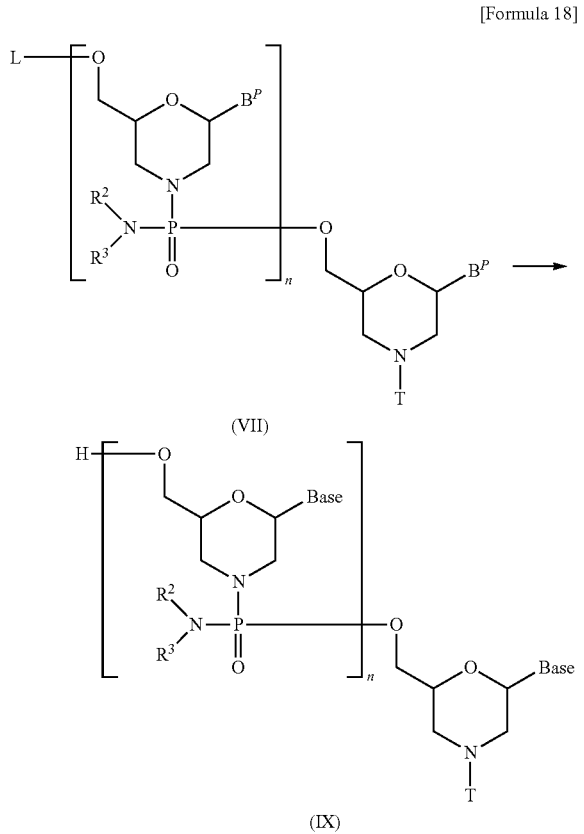

(VII)

(IX)

[wherein Base, $B^P$, L, n, $R^2$, $R^3$ and T are the same as defined above].

This step may be accomplished by treating compound (VII) with a deprotecting agent.

Examples of a "deprotecting agent" include concentrated aqueous ammonia and methylamine. Such a "deprotecting agent" available for use in this step may be used by being diluted with water, methanol, ethanol, isopropyl alcohol, acetonitrile, tetrahydrofuran, DMF, N,N-dimethylimidazolidinone, N-methylpiperidone, or a mixed solvent thereof. Among them, preferred is ethanol. The amount of a deprotecting agent to be used is, for example, reasonably in the range of 1 molar equivalent to 100000 molar equivalents, preferably in the range of 10 molar equivalents to 1000 molar equivalents, relative to 1 mole of compound (VII), by way of example.

The reaction temperature is, for example, reasonably in the range of 15° C. to 75° C., preferably in the range of 40° C. to 70° C., and more preferably in the range of 50° C. to 60° C. The reaction time for deprotection will vary depending on the type of compound (VII) and/or the reaction temperature, etc., but it is reasonably in the range of 10 minutes to 30 hours, preferably in the range of 30 minutes to 24 hours, and more preferably in the range of 5 hours to 20 hours.

(4) Step D:

This is a step where compound (IX) prepared in Step C is treated with an acid to prepare PMO

[Formula 19]

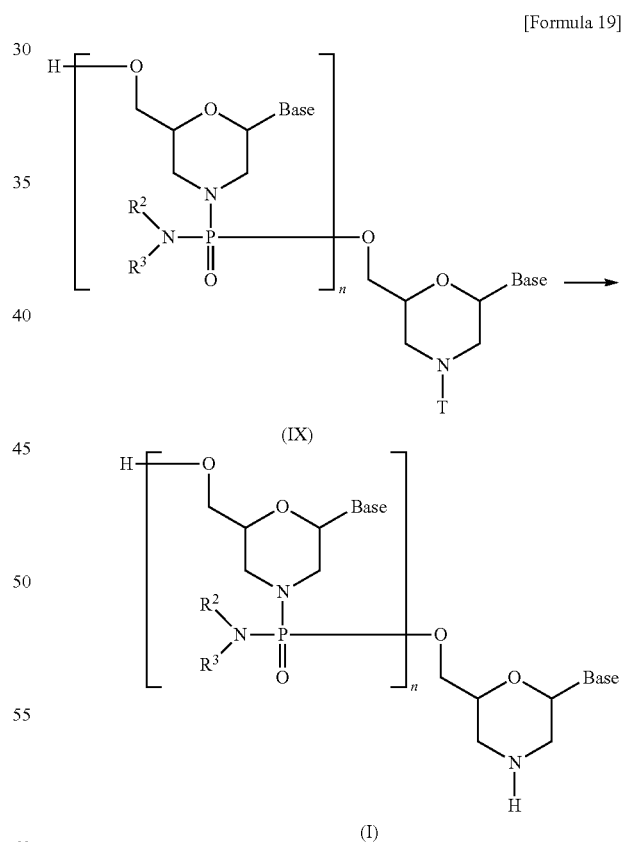

(IX)

(I)

[wherein Base, n, $R^2$, $R^3$ and T are the same as defined above].

This step may be accomplished by adding an acid to compound (IX).

Examples of an "acid" available for use in this step include trichloroacetic acid, dichloroacetic acid, acetic acid, phosphoric acid and hydrochloric acid, etc. As to the amount of an acid to be used, it is reasonable to use the acid in an amount to give a solution pH, for example, in the range of 0.1 to 4.0, more preferably in the range of 1.0 to 3.0. Any solvent may be used in this step as long as it is inert to the reaction, and examples include acetonitrile, water, or mixed solvents thereof.

The reaction temperature is preferably in the range of 10° C. to 50° C., more preferably in the range of 20° C. to 40° C., and even more preferably in the range of 25° C. to 35° C. The reaction time for deprotection will vary depending on the type of compound (IX) and/or the reaction temperature, etc., but it is reasonably in the range of 0.1 minutes to 5 hours, preferably in the range of 1 minute to 1 hour, and more preferably in the range of 1 minute to 30 minutes.

PMO (I) may be obtained from the reaction mixture obtained in this step by commonly used separation and purification means including extraction, concentration, neutralization, filtration, centrifugation, recrystallization, $C_8$ to $C_{18}$ reversed-phase column chromatography, cation exchange column chromatography, anion exchange column chromatography, gel filtration column chromatography, high performance liquid chromatography, dialysis, ultrafiltration and other means, which may be used either alone or in combination, whereby desired PMO (I) can be isolated and purified (see, e.g., WO1991/09033).

In the case of using reversed-phase chromatography for purification of PMO (I), a mixed solution of 20 mM triethylamine/acetate buffer and acetonitrile may be used as an elution solvent, by way of example.

Likewise, in the case of using ion exchange chromatography for purification of PMO (I), a mixed solution of 1 M aqueous sodium chloride and 10 mM aqueous sodium hydroxide may be used, by way of example.

The peptide nucleic acid oligomer is an antisense oligomer according to the present invention, whose constituent unit is a group represented by the following general formula:

[Formula 20]

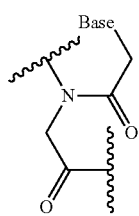

(wherein Base is the same as defined above).

Peptide nucleic acids may be prepared, for example, in accordance with the documents listed below.
1) P. E. Nielsen, M. Egholm, R. H. Berg, O. Buchardt, Science, 254, 1497 (1991)
2) M. Egholm, O. Buchardt, P. E. Nielsen, R. H. Berg, Jacs., 114, 1895 (1992)
3) K. L. Dueholm, M. Egholm, C. Behrens, L. Christensen, H. F. Hansen, T. Vulpius, K. H. Petersen, R. H. Berg, P. E. Nielsen, O. Buchardt, J. Org. Chem., 59, 5767 (1994)
4) L. Christensen, R. Fitzpatrick, B. Gildea, K. H. Petersen, H. F. Hansen, T. Koch, M. Egholm, O. Buchardt, P. E. Nielsen, J. Coull, R. H. Berg, J. Pept. Sci., 1, 175 (1995)
5) T. Koch, H. F. Hansen, P. Andersen, T. Larsen, H. G. Batz, K. Otteson, H. Orum, J. Pept. Res., 49, 80 (1997)

Moreover, the antisense oligomer of the present invention may be configured such that its 5'-terminal end is any one of the groups represented by chemical formulae (1) to (3) shown below, with (3) —OH being preferred.

[Formula 21]

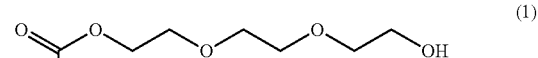

(1)

(2)

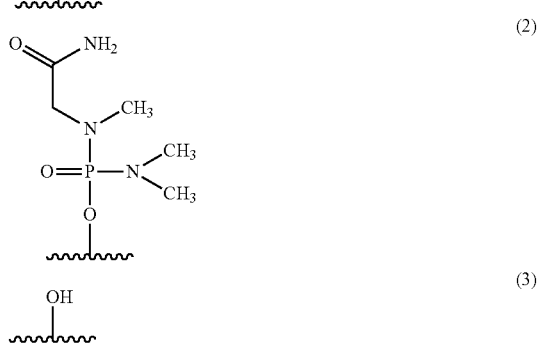

(3)

2. Pharmaceutical Composition

In a preferred embodiment, the antisense oligomer of the present invention allows inhibition of myostatin at the mRNA level through induction of exon skipping or mRNA degradation. Thus, an amyotrophic disease or a muscle wasting disease can be prevented or treated when the antisense oligomer of the present invention according to this preferred embodiment, a pharmaceutically acceptable salt or hydrate thereof is administered to a subject in need of prevention or treatment of an amyotrophic disease or a muscle wasting disease.

In some embodiments of the present invention, there is provided a pharmaceutical composition comprising the antisense oligomer of the present invention or a pharmaceutically acceptable salt or hydrate thereof as an active ingredient (hereinafter referred to as "the pharmaceutical composition of the present invention"). The pharmaceutical composition of the present invention is preferably provided for use in the treatment of a metabolic disorder (e.g., obesity, metabolic syndrome, diabetes), an amyotrophic disease or a muscle wasting disease. Examples of an amyotrophic disease or a muscle wasting disease include myogenic amyotrophy (e.g., muscular dystrophy (e.g., Duchenne muscular dystrophy, Fukuyama muscular dystrophy, myotonic dystrophy), congenital myopathy, inclusion body myositis), neurogenic amyotrophy (e.g., amyotrophic lateral sclerosis, spinal muscular atrophy, spinal and bulbar muscular atrophy), disuse amyotrophy (e.g., apoplexy-induced disuse syndrome), muscle wasting diseases (e.g., cancer cachexia, sepsis-related amyotrophy), various types of sarcopenia including age-related skeletal muscle loss (age-related sarcopenia), etc., with muscular dystrophy being preferred.

In some other embodiments of the present invention, there is provided a method for prevention or treatment of an amyotrophic disease or a muscle wasting disease, which comprises administering a subject in need of prevention or treatment of an amyotrophic disease or a muscle wasting disease with a therapeutically effective amount of the antisense oligomer of the present invention or a pharmaceutically acceptable salt or hydrate thereof. In this method, the antisense oligomer of the present invention or a pharmaceutically acceptable salt or hydrate thereof may be administered to the subject in the form of the pharmaceutical composition of the present invention.

In the context of the present invention, the term "subject" is intended to mean a human subject or a non-human warm-blooded animal, as exemplified by birds and non-human mammals (e.g., cow, monkey, cat, mouse, rat, guinea pig, hamster, pig, dog, rabbit, sheep, horse). The "subject" is preferably a human subject.

In some yet other embodiments of the present invention, there is provided use of the antisense oligomer of the present invention or a pharmaceutically acceptable salt or hydrate thereof in the manufacture of a pharmaceutical composition for treatment of an amyotrophic disease or a muscle wasting disease.

In some yet other embodiments of the present invention, there is provided the antisense oligomer of the present invention or a pharmaceutically acceptable salt or hydrate thereof for use in the treatment of an amyotrophic disease or a muscle wasting disease.

Examples of a pharmaceutically acceptable salt of the antisense oligomer of the present invention contained in the pharmaceutical composition of the present invention include alkali metal salts (e.g., sodium salt, potassium salt, lithium salt); alkaline earth metal salts (e.g., calcium salt, magnesium salt); metal salts (e.g., aluminum salt, iron salt, zinc salt, copper salt, nickel salt, cobalt salt); ammonium salt; organic amine salts (e.g., t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tetramethylammonium salt, tris(hydroxymethyl)aminomethane salt); hydrohalic acid salts (e.g., hydrofluoride salt, hydrochloride salt, hydrobromide salt, hydroiodide salt); inorganic acid salts (i.e., nitrate salt, perchlorate salt, sulfate salt, phosphate salt); lower alkanesulfonic acid salts (e.g., methanesulfonate salt, trifluoromethanesulfonate, ethanesulfonate salt); arylsulfonic acid salts (e.g., benzenesulfonate salt, p-toluenesulfonate salt); organic acid salts (e.g., acetate salt, malate salt, fumarate salt, succinate salt, citrate salt, tartrate salt, oxalate salt, maleate salt); amino acid salts (e.g., glycine salt, lysine salt, arginine salt, ornithine salt, glutamate salt, aspartate salt), etc. These salts may be prepared in any known manner.

The antisense oligomer of the present invention contained in the pharmaceutical composition of the present invention may be in the form of a hydrate thereof. Such a hydrate may be prepared in any known manner.

The pharmaceutical composition of the present invention may be administered in any pharmaceutically acceptable mode, which may be selected as appropriate for the intended therapeutic method. However, in terms of easy delivery to muscle tissue, preferred are intravenous administration, intraarterial administration, intramuscular administration, subcutaneous administration, oral administration, interstitial administration, percutaneous administration and so on. Moreover, the composition of the present invention may be in any dosage form, and examples include various types of injections, oral formulations, drops, inhalants, ointments, lotions, etc.

The pharmaceutical composition of the present invention comprises a carrier which promotes the delivery of the oligomer to muscle tissue. Such a carrier is not limited in any way as long as it is pharmaceutically acceptable, and examples include cationic carriers (e.g., cationic liposomes, cationic polymers) or viral envelope-based carriers. Examples of cationic liposomes include liposomes formed from 2-O-(2-diethylaminoethyl)carbamoyl-1,3-O-dioleoyl glycerol and a phospholipid as essential constituent members (hereinafter referred to as "liposome A"), Oligofectamine® (Invitrogen), Lipofectin® (Invitrogen), Lipofectamine® (Invitrogen), Lipofectamine 2000® (Invitrogen), DMRTE-C® (Invitrogen), GeneSilencer® (Gene Therapy Systems), TransMessenger® (QIAGEN), TransIT TKO® (Mirus) and Nucleofector II (Lonza). Among them, preferred is liposome A. Examples of cationic polymers include JetSI® (Qbiogene) and Jet-PET® (polyethyleneimine, Qbiogene). Examples of viral envelope-based carriers include GenomeOne® (HVJ-E liposomes, Ishihara Sangyo Kaisha, Ltd., Japan). Alternatively, it is also possible to use the pharmaceutical device shown in Japanese Patent No; 2924179 or the cationic carriers shown in JP WO2006/129594 and JP WO2008/096690.

For more details, reference may be made to U.S. Pat. Nos. 4,235,871 and 4,737,323, WO96/14057, "New RRC, Liposomes: A practical approach, IRL Press, Oxford (1990) pages 33-104," etc.

The concentration of the antisense oligomer of the present invention or a pharmaceutically acceptable salt or hydrate thereof contained in the pharmaceutical composition of the present invention will vary, e.g., depending on the type of carrier, but it is reasonably in the range of 0.1 nM to 100 μM, and preferably in the range of 100 nM to 10 μM. Likewise, the weight ratio of the carrier to the antisense oligomer of the present invention or a pharmaceutically acceptable salt or hydrate thereof contained in the pharmaceutical composition of the present invention (i.e., the carrier/antisense oligomer or pharmaceutically acceptable salt or hydrate thereof ratio) will vary, e.g., depending on the properties of the oligomer and the type of the carrier, but it is reasonably in the range of 0.1 to 100, and preferably in the range of 0.1 to 10.

The pharmaceutical composition of the present invention may optionally comprise a pharmaceutically acceptable additive, in addition to the antisense oligomer of the present invention or a pharmaceutically acceptable salt or hydrate thereof and a carrier as described above. Examples of such an additive include an emulsifier aid (e.g., a fatty acid containing 6 to 22 carbon atoms or a pharmaceutically acceptable salt thereof, albumin, dextran), a stabilizing agent (e.g., cholesterol, phosphatidic acid), an isotonizing agent (e.g., sodium chloride, glucose, maltose, lactose, sucrose, trehalose), and a pH adjuster (e.g., hydrochloric acid, sulfuric acid, phosphoric acid, acetic acid, sodium hydroxide, potassium hydroxide, triethanolamine). These additives may be used either alone or in combination. The content of the additive(s) in the pharmaceutical composition of the present invention is reasonably 90% by weight or less, preferably 70% by weight or less, and more preferably 50% by weight or less.

The pharmaceutical composition of the present invention may be prepared by adding the antisense oligomer of the present invention or a pharmaceutically acceptable salt or hydrate thereof to a dispersion of a carrier, followed by adequate stirring. An additive(s) may be added at any appropriate stage, either before or after adding the antisense oligomer of the present invention or a pharmaceutically acceptable salt or hydrate thereof. Any aqueous solvent may be used for adding the antisense oligomer of the present invention or a pharmaceutically acceptable salt or hydrate thereof as long as it is pharmaceutically acceptable, and examples include injectable water, injectable distilled water, electrolytic solutions (e.g., physiological saline), and sugar solutions (e.g., glucose solution, maltose solution). Moreover, in this case, conditions including pH and temperature may be selected as appropriate by those skilled in the art.

The pharmaceutical composition of the present invention may be formulated into a solution or a lyophilized formulation thereof, by way of example. Such a lyophilized formulation may be prepared in a standard manner by freeze-drying the pharmaceutical composition of the present invention in a solution form. For example, the pharmaceutical composition of the present invention in a solution form may be sterilized as appropriate and then dispensed in given amounts into vial bottles, followed by preliminary freezing under conditions of about −40° C. to −20° C. for about 2 hours, primary drying at about 0° C. to 10° C. under reduced pressure and then secondary drying at about 15° C. to 25° C. under reduced pressure. Moreover, in most cases, the vials may be purged with a nitrogen gas and then capped, thereby giving a lyophilized formulation of the pharmaceutical composition of the present invention.

Such a lyophilized formulation of the pharmaceutical composition of the present invention may generally be used after being reconstituted by addition of any appropriate solution (i.e., a reconstituting solution). Examples of such a reconstituting solution include injectable water, physiological saline, and other commonly used infusion solutions. The volume of such a reconstituting solution will vary, e.g., depending on the intended use and is not limited in any way, but it is reasonably 0.5- to 2-fold greater than the solution volume before freeze-drying, or 500 mL or less.

The dose for administration of the pharmaceutical composition of the present invention is desirably adjusted in consideration of the type of the antisense oligomer of the present invention or a pharmaceutically acceptable salt or hydrate thereof contained therein, the intended dosage form, the condition of a subject such as age and body weight, the route of administration, and the nature and severity of a disease. If the subject is a human subject, the daily dose for adults is generally in the range of 0.1 mg to 10 g/human, preferably in the range of 1 mg to 1 g/human, calculated as the amount of the antisense oligomer of the present invention or a pharmaceutically acceptable salt or hydrate thereof. This numerical range may vary depending on the type of disease to be targeted, the mode of administration, and/or the type of target molecule. Thus, a dose lower than this range may be sufficient in some cases, or conversely, a dose higher than this range should be required in some cases. Moreover, the pharmaceutical composition of the present invention may be administered once to several times a day or at intervals of one to several days.

In another embodiment, the pharmaceutical composition of the present invention may be a pharmaceutical composition comprising a vector capable of expressing the antisense oligonucleotide of the present invention and a carrier as described above. Such an expression vector may be capable of expressing a plurality of antisense oligonucleotides according to the present invention. Such a pharmaceutical composition may optionally comprise a pharmaceutically acceptable additive, as described above. The concentration of the expression vector contained in this pharmaceutical composition will vary, e.g., depending on the type of carrier, but it is reasonably in the range of 0.1 nM to 100 μM and preferably in the range of 100 nM to 10 μM. The weight ratio of the carrier to the expression vector contained in this pharmaceutical composition (i.e., the carrier/expression vector ratio) will vary, e.g., depending on the properties of the expression vector and the type of the carrier, but it is reasonably in the range of 0.1 to 100, and preferably in the range of 0.1 to 10. Moreover, the content of the carrier contained in this pharmaceutical composition is the same as described above, and procedures for preparation are also the same as described above.

It should be noted that all publications cited herein, including prior art documents, patent gazettes and other patent documents, are incorporated herein by reference.

The present invention will be further described in more detail below by way of the following illustrative examples, although the present invention is not limited thereto.

EXAMPLES

The present invention will be further described in more detail below by way of the following illustrative examples and test examples, although the present invention is not limited thereto.

Reference Example 1

4-{[(2 S,6R)-6-(5-Methyl-2,4-dioxopyrimidin-1-yl)-4-tritylmorpholin-2-yl]methoxy}-4-oxobutanoic Acid Loaded on Aminopolystyrene Resin Step 1: Preparation of 4-{[(2S,6R)-6-(5-methyl-2,4-dioxopyrimidin-1-yl)-4-tritylmorpholin-2-yl] methoxy}-4-oxobutanoic Acid Under an argon atmosphere, 1-[(2R,6S)-6-(hydroxymethyl)-4-tritylmorpholin-2-yl]-5-methylpyrimidine-2,4-dione (41.11 g) and 4-dimethylaminopyridine (4-DMAP) (15.58 g) were suspended in dichloromethane (850 mL), and succinic anhydride (12.76 g) was then added thereto, followed by stirring at room temperature for 3.5 hours. The reaction solution was extracted with dichloromethane and 1 M aqueous sodium dihydrogen phosphate. The resulting organic layer was washed sequentially with 1 M aqueous sodium dihydrogen phosphate and saturated aqueous sodium chloride. The resulting organic layer was dried over sodium sulfate and concentrated under reduced pressure. To the resulting solid, dichloromethane (600 mL) was added to effect crystallization, followed by filtration. After additional dichloromethane (300 mL) was added, the crystals were stirred for 5 minutes, and then filtered and dried overnight under reduced pressure to obtain the desired product (50.2 g).

Step 2: Preparation of 4-{[(2S,6R)-6-(5-methyl-2,4-dioxopyrimidin-1-yl)-4-tritylmorpholin-2-yl] methoxy}-4-oxobutanoic Acid Loaded on Aminopolystyrene Resin 4-{[(2S,6R)-6-(5-Methyl-2,4-dioxopyrimidin-1-yl)-4-tritylmorpholin-2-yl]methoxy}-4-oxobutanoic acid (50.2 g) was dissolved in pyridine (dehydrated) (600 mL), followed by addition of 4-DMAP (12.4 g) and 1-(3-dimethylaminopropyl)-3-ethylcarbodiimide hydrochloride (77.6 g). The aminopolystyrene resin Aminomethyl resin (a product of Watanabe Chemical Industries, Ltd., Japan, A00673, 200 to 400 mesh, 1 mmol/g, 1% DVB) (40.5 g) and triethylamine (69.6 mL) were then added to this mixture, followed by shaking at room temperature for 4 days. After the reaction, the resin was collected by filtration. The resulting resin was washed sequentially with pyridine, methanol and dichloromethane, and then dried under reduced pressure. To the resulting resin, tetrahydrofuran (dehydrated) (500 mL), acetic anhydride (104 mL) and 2,6-lutidine (128 mL) were added, followed by shaking at room temperature for 4 hours. The resin was collected by filtration, washed sequentially with pyridine, methanol and dichloromethane, and then dried under reduced pressure to obtain 59.0 g of the desired product.

To determine the loading amount of the desired product, the molar amount of trityl per gram of the resin was measured in a known manner as UV absorbance at 409 nm. The loading amount on the resin was found to be 467.83 μmol/g.

Conditions for UV measurement
Instrument: U-2910 (Hitachi, Ltd., Japan)
Solvent: methanesulfonic acid
Wavelength: 409 nm
ε value: 45000

Reference Example 2

4-{[(2S,6R)-6-(4-Benzamido-2-oxopyrimidin-1-yl)-4-tritylmorpholin-2-yl]methoxy}-4-oxobutanoic Acid Loaded on Aminopolystyrene Resin The same procedures as shown in Reference Example 1 were repeated to prepare the titled compound, except that 1-[(2R,6S)-6-(hydroxymethyl)-4-tritylmorpholin-2-yl]-5-methylpyrimidine-2,4-dione used in Step 1 of Reference Example 1 was replaced in this step with N-{1-[(2R,6S)-6-(hydroxymethyl)-4-tritylmorpholin-2-yl]-2-oxo-1,2-dihydropyrimidin-4-yl}benzamide.

To determine the loading amount of the desired product, the molar amount of trityl per gram of the resin was measured in a known manner as UV absorbance at 409 nm. The loading amount on the resin was found to be 460.28 μmol/g.

Reference Example 3

4-{[(2S,6R)-6-(6-Benzamidopurin-9-yl)-4-tritylmorpholin-2-yl]methoxy}-4-oxobutanoic Acid Loaded on Aminopolystyrene Resin The same procedures as shown in Reference Example 1 were repeated to prepare the titled compound, except that 1-[(2R,6S)-6-(hydroxymethyl)-4-tritylmorpholin-2-yl]-5-methylpyrimidine-2,4-dione used in Step 1 of Reference Example 1 was replaced in this step with N-{9-[(2R,6S)-6-(hydroxymethyl)-4-tritylmorpholin-2-yl]purin-6-yl}benzamide.

To determine the loading amount of the desired product, the molar amount of trityl per gram of the resin was measured in a known manner as UV absorbance at 409 nm. The loading amount on the resin was found to be 425.13 μmol/g.

Reference Example 4

4-{{(2S,6R)-6-{6-(2-Cyanoethoxy)-2-[(2-phenoxyacetyl)amino]purin-9-yl}-4-tritylmorpholin-2-yl}methoxy}-4-oxobutanoic Acid Loaded on Aminopolystyrene Resin The same procedures as shown in Reference Example 1 were repeated to prepare the titled compound, except that 1-[(2R,6S)-6-(hydroxymethyl)-4-tritylmorpholin-2-yl]-5-methylpyrimidine-2,4-dione used in Step 1 of Reference Example 1 was replaced in this step with N-{6-(2-cyanoethoxy)-9-[(2R,6S)-6-(hydroxymethyl)-4-tritylmorpholin-2-yl]purin-2-yl}-2-phenoxyacetamide.

To determine the loading amount of the desired product, the molar amount of trityl per gram of the resin was measured in a known manner as UV absorbance at 409 nm. The loading amount on the resin was found to be 341.09 μmol/g.

In accordance with the descriptions in Example 1 shown below or in accordance with the procedures described in PCT/JP2015/57180 using a nucleic acid synthesizer (AKTA Oligopilot 10 plus), PMO Nos. 1 to 191, 198, 199, 201 to 316, 321 to 323, 325 to 327 and 333 indicated in Tables 1 to 3 were synthesized (the 5'-terminal end is group (3)).

TABLE 1

| PMO No. | Sequence name | Nucleotide sequence (5'→3') | Molecular weight (calculated) | Molecular weight (measured) | SEQ ID NO: |
|---|---|---|---|---|---|
| 1 | MSTN_H2_128-140_157-169 | TTCATAGGTTTGACACAAACACTGTT | 8590.98 | 8591.04 | 93 |
| 2 | MSTN_H2_169-181_213-225 | TGCCTGGGTTCATCTTGTACCGTCTT | 8556.93 | 8556.73 | 94 |
| 3 | MSTN_HM2_169-181_341-353 | TGGGAAGGTTACACTTGTACCGTCTT | 8638.98 | 8638.93 | 95 |
| 4 | MSTN_HM2_169-181_353-365 | TTCTCCTGGTCCTCTTGTACCGTCTT | 8467.90 | 8467.22 | 96 |
| 5 | MSTN_H2_12-24_128-140 | CACAAACACTGTTCATCCACTTGCAT | 8480.95 | 8480.44 | 97 |
| 6 | MSTN_H2_42-54_128-140 | CACAAACACTGTTTAAATTTAAAGAA | 8601.01 | 8600.99 | 98 |
| 7 | MSTN_HM2_52-64_128-140 | CACAAACACTGTTATTTTAGAGCTAA | 8583.99 | 8583.56 | 99 |
| 8 | MSTN_HM2_169-181_201-213 | TGTCAAGTTTCAGCTTGTACCGTCTT | 8564.94 | 8564.73 | 100 |
| 9 | MSTN_H2_22-34_128-140 | CACAAACACTGTTTTGGGTTTTCCAT | 8557.95 | 8557.82 | 101 |
| 10 | MSTN_HM2_128-140_347-359 | TGGTCCTGGGAAGCACAAACACTGTT | 8641.99 | 8641.67 | 102 |
| 11 | MSTN_H2_2-14_116-128 | TGTAGGAGTCTCGCATTAGAAAATCA | 8665.01 | 8665.04 | 103 |
| 12 | MSTN_H2_32-44_128-140 | CACAAACACTGTTGAAGCAACATTTG | 8593.99 | 8593.64 | 104 |

TABLE 1-continued

| PMO No. | Sequence name | Nucleotide sequence (5'→3') | Molecular weight (calculated) | Molecular weight (measured) | SEQ ID NO: |
|---|---|---|---|---|---|
| 13 | MSTN_H2_12-24_116-128 | TGTAGGAGTCTCGCATCCACTTGCAT | 8583.96 | 8583.74 | 105 |
| 14 | MSTN_HM2_177-189_331-343 | ACAGCAAGATCATCAGTATACCTTGT | 8584.98 | 8584.99 | 106 |
| 15 | MSTN_HM2_177-189_351-363 | CTCCTGGTCCTGGCAGTATACCTTGT | 8550.94 | 8550.82 | 107 |
| 16 | MSTN_H2_2-14_128-140 | CACAAACACTGTTCATTAGAAAATCA | 8561.99 | 8561.39 | 108 |
| 17 | MSTN_H2_72-84_128-140 | CACAAACACTGTTTTACTACTTTATT | 8500.94 | 8500.36 | 109 |
| 18 | MSTN_HM2_177-189_341-353 | TGGGAAGGTTACACAGTATACCTTGT | 8672.00 | 8672.41 | 110 |
| 19 | MSTN_H2_62-74_128-140 | CACAAACACTGTTATTGTATTGTATT | 8580.97 | 8580.58 | 111 |
| 20 | MSTN_H2_82-94_128-140 | CACAAACACTGTTAGTTGGGCCTTTA | 8591.97 | 8591.99 | 112 |
| 21 | MSTN_H2_2-14_119-131 | TGTTGTAGGAGTCCATTAGAAAATCA | 8680.01 | 8681.03 | 113 |
| 22 | MSTN_H2_2-14_122-134 | CACTGTTGTAGGACATTAGAAAATCA | 8649.01 | 8649.13 | 114 |
| 23 | MSTN_H2_92-104_128-140 | CACAAACACTGTTATATATCCATAGT | 8543.97 | 8544.20 | 115 |
| 24 | MSTN_H2_102-114_128-140 | CACAAACACTGTTCGGGTCTCAAATA | 8569.98 | 8570.28 | 116 |
| 25 | MSTN_H2_7-19_116-128 | TGTAGGAGTCTCGACTTGCATTAGAA | 8672.00 | 8671.90 | 117 |
| 26 | MSTN_H2_2-14_113-125 | AGGAGTCTCGACGCATTAGAAAATCA | 8659.02 | 8659.54 | 118 |
| 27 | MSTN_H2_2-14_125-137 | AAACACTGTTGTACATTAGAAAATCA | 8617.01 | 8617.59 | 119 |
| 28 | MSTN_H2_112-124_128-140 | CACAAACACTGTTGGAGTCTCGACGG | 8626.99 | 8627.55 | 120 |
| 29 | MSTN_H2_32-44_178-190 | CCAGTATACCTTGGAAGCAACATTTG | 8600.98 | 8599.85 | 121 |
| 30 | MSTN_H2_32-44_193-205 | TTCAGAGATCGGAGAAGCAACATTTG | 8690.02 | 8689.34 | 122 |
| 31 | MSTN_H2_32-44_347-359 | TGGTCCTGGGAAGGAAGCAACATTTG | 8722.02 | 8722.45 | 123 |
| 32 | MSTN_HM2_193-205_347-359 | TGGTCCTGGGAAGTTCAGAGATCGGA | 8738.02 | 8737.65 | 124 |
| 33 | MSTN_H2_2-14_347-359 | TGGTCCTGGGAAGCATTAGAAAATCA | 8690.02 | 8689.78 | 125 |
| 34 | MSTN_H2_32-44_116-128 | TGTAGGAGTCTCGGAAGCAACATTTG | 8697.01 | 8696.54 | 126 |
| 35 | MSTN_H2_116-128_178-190 | CCAGTATACCTTGTGTAGGAGTCTCG | 8623.97 | 8623.93 | 127 |
| 36 | MSTN_H2_4-16_116-128 | TGTAGGAGTCTCGTGCATTAGAAAAT | 8696.01 | 8695.71 | 128 |
| 37 | MSTN_H2_9-21_116-128 | TGTAGGAGTCTCGCCACTTGCATTAG | 8623.97 | 8623.22 | 129 |
| 38 | MSTN_H2_-4-9_116-128 | TGTAGGAGTCTCGGAAAATCAGCTAT | 8681.01 | 8681.53 | 130 |
| 39 | MSTN_H2_-2-11_116-128 | TGTAGGAGTCTCGTAGAAAATCAGCT | 8681.01 | 8681.66 | 131 |
| 40 | MSTN_H2_2-14_32-44 | GAAGCAACATTTGCATTAGAAAATCA | 8642.02 | 8642.96 | 132 |
| 41 | MSTN_H2_2-14_178-190 | CCAGTATACCTTGCATTAGAAAATCA | 8568.98 | 8569.60 | 133 |
| 42 | MSTN_H2_3-14_117-128 | TGTAGGAGTCTCCATTAGAAAATC | 7970.77 | 7971.87 | 134 |
| 43 | MSTN_H2_2-14_193-205 | TTCAGAGATCGGACATTAGAAAATCA | 8658.02 | 8657.79 | 135 |
| 44 | MSTN_H2_116-128_347-359 | TGGTCCTGGGAAGTGTAGGAGTCTCG | 8745.01 | 8744.89 | 136 |
| 45 | MSTN_H2_116-128_193-205 | TTCAGAGATCGGATGTAGGAGTCTCG | 8713.01 | 8713.65 | 137 |
| 46 | MSTN_H2_2-13_116-127 | GTAGGAGTCTCGATTAGAAAATCA | 8019.79 | 8019.95 | 138 |
| 47 | MSTN_H2_2-13_117-128 | TGTAGGAGTCTCATTAGAAAATCA | 7994.78 | 7994.91 | 139 |
| 48 | MSTN_H2_3-14_116-127 | GTAGGAGTCTCGCATTAGAAAATC | 7995.78 | 7995.99 | 140 |
| 49 | MSTN_H2_2-14_102-114 | CGGGTCTCAAATACATTAGAAAATCA | 8618.01 | 8618.54 | 141 |
| 50 | MSTN_H2_2-14_106-118 | TCGACGGGTCTCACATTAGAAAATCA | 8609.99 | 8610.74 | 142 |
| 51 | MSTN_H2_2-14_110-122 | AGTCTCGACGGGTCATTAGAAAATCA | 8650.01 | 8650.84 | 143 |

TABLE 1-continued

| PMO No. | Sequence name | Nucleotide sequence (5'→3') | Molecular weight (calculated) | Molecular weight (measured) | SEQ ID NO: |
|---|---|---|---|---|---|
| 52 | MSTN_H2_106-118_128-140 | CACAAACACTGTTTCGACGGGTCTCA | 8561.97 | 8562.71 | 144 |
| 53 | MSTN_H2_109-121_128-140 | CACAAACACTGTTGTCTCGACGGGTC | 8577.97 | 8578.09 | 145 |
| 54 | MSTN_H2_-1-12_116-128 | TGTAGGAGTCTCGTTAGAAAATCAGC | 8681.01 | 8681.08 | 146 |
| 55 | MSTN_H2_1-13_116-128 | TGTAGGAGTCTCGATTAGAAAATCAG | 8705.02 | 8704.93 | 147 |
| 56 | MSTN_H2_1-14_116-127 | GTAGGAGTCTCGCATTAGAAAATCAG | 8690.02 | 8690.13 | 148 |
| 57 | MSTN_H2_-1-14_116-126 | TAGGAGTCTCGCATTAGAAAATCAGC | 8650.01 | 8649.42 | 149 |
| 58 | MSTN_H2_2-14_117-129 | TTGTAGGAGTCTCCATTAGAAAATCA | 8640.00 | 8639.61 | 150 |
| 59 | MSTN_H2_2-14_118-130 | GTTGTAGGAGTCTCATTAGAAAATCA | 8680.01 | 8679.96 | 151 |
| 60 | MSTN_H2_3-15_116-128 | TGTAGGAGTCTCGGCATTAGAAAATC | 8681.01 | 8680.78 | 152 |
| 61 | MSTN_H2_2-14_114-126 | TAGGAGTCTCGACCATTAGAAAATCA | 8634.01 | 8633.96 | 153 |
| 62 | MSTN_H2_2-14_115-127 | GTAGGAGTCTCGACATTAGAAAATCA | 8674.02 | 8673.75 | 154 |
| 63 | MSTN_H2_3-15_115-127 | GTAGGAGTCTCGAGCATTAGAAAATC | 8690.02 | 8689.33 | 155 |
| 64 | MSTN_H2_3-15_117-129 | TTGTAGGAGTCTCGCATTAGAAAATC | 8656.00 | 8655.37 | 156 |
| 65 | MSTN_H2_116-128_213-225 | TGCCTGGGTTCATTGTAGGAGTCTCG | 8670.98 | 8670.44 | 157 |
| 66 | MSTN_H2_116-128_268-280 | TGTTTGAGCCAATTGTAGGAGTCTCG | 8678.99 | 8679.10 | 158 |
| 67 | MSTN_H2_1-13_115-127 | GTAGGAGTCTCGAATTAGAAAATCAG | 8714.03 | 8714.18 | 159 |
| 68 | MSTN_H2_1-13_117-129 | TTGTAGGAGTCTCATTAGAAAATCAG | 8680.01 | 8679.50 | 160 |
| 69 | MSTN_H2_2-13_116-128 | TGTAGGAGTCTCGATTAGAAAATCA | 8349.90 | 8349.01 | 161 |
| 70 | MSTN_H2_3-14_116-128 | TGTAGGAGTCTCGCATTAGAAAATC | 8325.89 | 8324.88 | 162 |
| 71 | MSTN_H2_2-14_116-127 | GTAGGAGTCTCGCATTAGAAAATCA | 8334.90 | 8333.29 | 163 |
| 72 | MSTN_H2_2-14_117-128 | TGTAGGAGTCTCCATTAGAAAATCA | 8309.89 | 8310.03 | 164 |
| 73 | MSTN_H2_117-128_192-203 | CAGAGATCGGATTGTAGGAGTCTC | 8027.78 | 8027.24 | 165 |
| 74 | MSTN_H2_117-128_193-204 | TCAGAGATCGGATGTAGGAGTCTC | 8027.78 | 8027.42 | 166 |
| 75 | MSTN_H2_117-128_194-205 | TTCAGAGATCGGTGTAGGAGTCTC | 8018.77 | 8018.26 | 167 |
| 76 | MSTN_H2_114-126_194-205 | TTCAGAGATCGGTAGGAGTCTCGAC | 8342.89 | 8342.62 | 168 |
| 77 | MSTN_H2_115-128_192-203 | CAGAGATCGGATTGTAGGAGTCTCGA | 8722.02 | 8722.80 | 169 |
| 78 | MSTN_H2_114-126_193-204 | TCAGAGATCGGATAGGAGTCTCGAC | 8351.90 | 8352.40 | 170 |
| 79 | MSTN_H2_117-128_192-205 | TTCAGAGATCGGATTGTAGGAGTCTC | 8688.00 | 8687.62 | 171 |
| 80 | MSTN_H2_3-14_116-125 | AGGAGTCTCGCATTAGAAAATC | 7310.55 | 7310.13 | 172 |
| 81 | MSTN_H2_3-15_115-125 | AGGAGTCTCGAGCATTAGAAAATC | 8004.79 | 8004.56 | 173 |
| 82 | MSTN_H2_-1-11_116-127 | GTAGGAGTCTCGTAGAAAATCAGC | 8020.79 | 8020.35 | 174 |
| 83 | MSTN_H2_-1-12_115-125 | AGGAGTCTCGATTAGAAAATCAGC | 8004.79 | 8005.06 | 175 |
| 84 | MSTN_H2_3-15_116-127 | GTAGGAGTCTCGGCATTAGAAAATC | 8350.90 | 8351.16 | 176 |
| 85 | MSTN_H2_-1-12_116-127 | GTAGGAGTCTCGTTAGAAAATCAGC | 8350.90 | 8350.46 | 177 |
| 86 | MSTN_H2_117-125_211-225 | TGCCTGGGTTCATGTAGGAGTCTC | 7985.75 | 7986.39 | 178 |
| 87 | MSTN_H2_117-127_216-228 | CAGTGCCTGGGTTGTAGGAGTCTC | 8010.76 | 8011.08 | 179 |
| 88 | MSTN_H2_2-14_116-126 | TAGGAGTCTCGCATTAGAAAATCA | 7979.78 | 7979.75 | 180 |
| 89 | MSTN_H2_-1-12_116-126 | TAGGAGTCTCGTTAGAAAATCAGC | 7995.78 | 7996.47 | 181 |
| 90 | MSTN_H2_-1-14_116-126(-5A) | TAGGAGTCTCGCATTAGAAAATCAGC | 8310.89 | 8311.25 | 182 |

TABLE 1-continued

| PMO No. | Sequence name | Nucleotide sequence (5'→3') | Molecular weight (calculated) | Molecular weight (measured) | SEQ ID NO: |
|---|---|---|---|---|---|
| 91 | MSTN_H2_117-127_344-358 | GGTCCTGGGAAGGTTGTAGGAGTCTC | 8745.01 | 8745.96 | 183 |
| 92 | MSTN_H2_4-14_116-126 | TAGGAGTCTCGCATTAGAAAAT | 7325.55 | 7325.56 | 184 |
| 93 | MSTN_H2_3-14_116-126 | TAGGAGTCTCGCATTAGAAAATC | 7640.66 | 7640.90 | 185 |
| 94 | MSTN_H2_3-15_116-126 | TAGGAGTCTCGGCATTAGAAAATC | 7995.78 | 7996.39 | 186 |
| 95 | MSTN_H2_117-127_344-356 | TCCTGGGAAGGTTGTAGGAGTCTC | 8034.77 | 8035.29 | 187 |
| 96 | MSTN_H2_114-125_194-205 | TTCAGAGATCGGAGGAGTCTCGAC | 8012.78 | 8012.48 | 188 |
| 97 | MSTN_H2_114-125_129-140 | CACAAACACTGTAGGAGTCTCGAC | 7925.76 | 7925.65 | 189 |
| 98 | MSTN_H2_115-126_129-140 | CACAAACACTGTTAGGAGTCTCGA | 7940.76 | 7940.82 | 190 |
| 99 | MSTN_H2_117-126_129-140 | CACAAACACTGTTAGGAGTCTC | 7246.52 | 7246.96 | 191 |
| 100 | MSTN_H2_117-127_130-140 | CACAAACACTGGTAGGAGTCTC | 7271.53 | 7272.21 | 192 |
| 101 | MSTN_H2_117-127_129-140 | CACAAACACTGTGTAGGAGTCTC | 7601.64 | 7602.24 | 193 |
| 102 | MSTN_H2_117-127_192-202 | AGAGATCGGATGTAGGAGTCTC | 7382.56 | 7382.52 | 194 |
| 103 | MSTN_H2_117-127_195-205 | TTCAGAGATCGGTAGGAGTCTC | 7333.54 | 7333.88 | 195 |
| 104 | MSTN_H2_117-128_213-225 | TGCCTGGGTTCATTGTAGGAGTCTC | 8315.86 | 8316.77 | 196 |
| 105 | MSTN_H2_114-125_213-225 | TGCCTGGGTTCATAGGAGTCTCGAC | 8309.86 | 8310.88 | 197 |
| 106 | MSTN_H2_114-125_345-356 | TCCTGGGAAGGTAGGAGTCTCGAC | 8028.78 | 8028.48 | 198 |
| 107 | MSTN_H2_117-128_348-359 | TGGTCCTGGGAATGTAGGAGTCTC | 8034.77 | 8034.02 | 199 |
| 108 | MSTN_H2_114-125_211-222 | CTGGGTTCATGTAGGAGTCTCGAC | 7994.76 | 7995.78 | 200 |
| 109 | MSTN_H2_117-128_211-222 | CTGGGTTCATGTTGTAGGAGTCTC | 8000.75 | 7999.95 | 201 |
| 110 | MSTN_H2_115-125_129-140 | CACAAACACTGTAGGAGTCTCGA | 7610.65 | 7609.85 | 202 |
| 111 | MSTN_H2_117-125_129-140 | CACAAACACTGTAGGAGTCTC | 6916.41 | 6916.94 | 203 |
| 112 | MSTN_H2_117-128_193-205 | TTCAGAGATCGGATGTAGGAGTCTC | 8357.89 | 8357.86 | 204 |
| 113 | MSTN_H2_-1-10_15-26 | TCCATCCACTTGAGAAAATCAGC | 7545.63 | 7545.89 | 205 |
| 114 | MSTN_H2_117-128_213-223 | CCTGGGTTCATTGTAGGAGTCTC | 7630.63 | 7631.02 | 206 |
| 115 | MSTN_H2_119-125_211-225 | TGCCTGGGTTCATGTAGGAGTC | 7340.53 | 7341.36 | 207 |
| 116 | MSTN_H2_117-125_211-223 | CCTGGGTTCATGTAGGAGTCTC | 7300.52 | 7301.46 | 208 |
| 117 | MSTN_H2_-1-10_115-125 | AGGAGTCTCGAAGAAAATCAGC | 7344.57 | 7346.16 | 209 |
| 118 | MSTN_H2_-1-10_116-126 | TAGGAGTCTCGAGAAAATCAGC | 7335.56 | 7336.62 | 210 |
| 119 | MSTN_H2_3-13_116-126 | TAGGAGTCTCGATTAGAAAATC | 7325.55 | 7326.53 | 211 |
| 120 | MSTN_H2_117-128_210-221 | TGGGTTCATGTCTGTAGGAGTCTC | 8000.75 | 8000.51 | 212 |
| 121 | MSTN_H2_117-128_212-223 | CCTGGGTTCATGTGTAGGAGTCTC | 7985.75 | 7985.16 | 213 |
| 122 | MSTN_H2_117-128_211-221 | TGGGTTCATGTTGTAGGAGTCTC | 7685.64 | 7685.86 | 214 |
| 123 | MSTN_H2_118-128_211-222 | CTGGGTTCATGTTGTAGGAGTCT | 7685.64 | 7686.62 | 215 |
| 124 | MSTN_H2_117-128_212-222 | CTGGGTTCATGTGTAGGAGTCTC | 7670.64 | 7670.94 | 216 |
| 125 | MSTN_H2_117-128_192-204 | TCAGAGATCGGATTGTAGGAGTCTC | 8357.89 | 8358.93 | 217 |
| 126 | MSTN_H2_117-128_213-222 | CTGGGTTCATTGTAGGAGTCTC | 7315.52 | 7316.24 | 218 |
| 127 | MSTN_H2_117-129_213-222 | CTGGGTTCATTTGTAGGAGTCTC | 7645.63 | 7646.63 | 219 |
| 128 | MSTN_H2_117-126_211-222 | CTGGGTTCATGTTAGGAGTCTC | 7315.52 | 7316.36 | 220 |
| 129 | MSTN_H2_114-125_210-221 | TGGGTTCATGTCAGGAGTCTCGAC | 7994.76 | 7994.90 | 221 |

TABLE 1-continued

| PMO No. | Sequence name | Nucleotide sequence (5'→3') | Molecular weight (calculated) | Molecular weight (measured) | SEQ ID NO: |
|---|---|---|---|---|---|
| 130 | MSTN_H2_117-128_191-202 | AGAGATCGGATTTGTAGGAGTCTC | 8042.78 | 8043.31 | 222 |
| 131 | MSTN_HM2_118-127_130-140 | CACAAACACTGGTAGGAGTCT | 6956.43 | 6956.19 | 223 |
| 132 | MSTN_H2_117-127_130-139 | ACAAACACTGGTAGGAGTCTC | 6956.43 | 6956.76 | 224 |
| 133 | MSTN_H2_114-125_212-223 | CCTGGGTTCATGAGGAGTCTCGAC | 7979.75 | 7979.45 | 225 |
| 134 | MSTN_H2_118-128_213-223 | CCTGGGTTCATTGTAGGAGTCT | 7315.52 | 7315.38 | 226 |
| 135 | MSTN_H2_118-128_213-222 | CTGGGTTCATTGTAGGAGTCT | 7000.41 | 7000.35 | 227 |
| 136 | MSTN_H2_119-128_213-223 | CCTGGGTTCATTGTAGGAGTC | 6985.41 | 6984.76 | 228 |
| 137 | MSTN_H2_117-126_213-223 | CCTGGGTTCATTAGGAGTCTC | 6945.40 | 6945.37 | 229 |
| 138 | MSTN_H2_117-125_211-222 | CTGGGTTCATGTAGGAGTCTC | 6985.41 | 6985.57 | 230 |
| 139 | MSTN_H2_117-127_214-223 | CCTGGGTTCAGTAGGAGTCTC | 6970.41 | 6969.84 | 231 |
| 140 | MSTN_H2_117-128_131-140 | CACAAACACTTGTAGGAGTCTC | 7246.52 | 7246.02 | 232 |
| 141 | MSTN_H2_115-125_130-140 | CACAAACACTGAGGAGTCTCGA | 7280.54 | 7280.06 | 233 |
| 142 | MSTN_HM2_119-129_194-206 | TTTCAGAGATCGGTTGTAGGAGTC | 8033.77 | 8033.86 | 234 |
| 143 | MSTN_HM2_118-129_193-204 | TCAGAGATCGGATTGTAGGAGTCT | 8042.78 | 8043.06 | 235 |
| 144 | MSTN_H2_114-124_130-140 | CACAAACACTGGGAGTCTCGAC | 7256.53 | 7256.65 | 236 |
| 145 | MSTN_H2_114-125_211-221 | TGGGTTCATGTAGGAGTCTCGAC | 7679.65 | 7679.17 | 237 |
| 146 | MSTN_H2_114-126_213-222 | CTGGGTTCATTAGGAGTCTCGAC | 7639.64 | 7640.01 | 238 |
| 147 | MSTN_H2_117-128_195-206 | TTTCAGAGATCGTGTAGGAGTCTC | 7993.76 | 7994.63 | 239 |
| 148 | MSTN_H2_117-128_211-223 | CCTGGGTTCATGTTGTAGGAGTCTC | 8315.86 | 8316.07 | 240 |
| 149 | MSTN_H2_117-126_213-222 | CTGGGTTCATTAGGAGTCTC | 6630.29 | 6631.27 | 241 |
| 150 | MSTN_HM2_119-129_193-205 | TTCAGAGATCGGATTGTAGGAGTC | 8042.78 | 8043.75 | 242 |
| 151 | MSTN_H2_118-127_214-223 | CCTGGGTTCAGTAGGAGTCT | 6655.30 | 6654.87 | 243 |
| 152 | MSTN_H2_117-126_214-223 | CCTGGGTTCATAGGAGTCTC | 6615.29 | 6615.00 | 244 |
| 153 | MSTN_H2_117-127_215-223 | CCTGGGTTCGTAGGAGTCTC | 6631.29 | 6631.07 | 245 |
| 154 | MSTN_H2_114-124_214-223 | CCTGGGTTCAGGAGTCTCGAC | 6955.40 | 6955.05 | 246 |
| 155 | MSTN_H2_115-125_214-223 | CCTGGGTTCAAGGAGTCTCGA | 6979.42 | 6979.46 | 247 |
| 156 | MSTN_H2_118-128_214-223 | CCTGGGTTCATGTAGGAGTCT | 6985.41 | 6985.70 | 248 |
| 157 | MSTN_HM2_118-129_192-203 | CAGAGATCGGATTTGTAGGAGTCT | 8042.78 | 8042.98 | 249 |
| 158 | MSTN_HM2_118-129_194-205 | TTCAGAGATCGGTTGTAGGAGTCT | 8033.77 | 8033.36 | 250 |
| 159 | MSTN_HM2_119-129_192-204 | TCAGAGATCGGATTTGTAGGAGTC | 8042.78 | 8043.12 | 251 |
| 160 | MSTN_H2_117-129_213-223 | CCTGGGTTCATTTGTAGGAGTCTC | 7960.74 | 7960.09 | 252 |
| 161 | MSTN_H2_117-127_188-198 | ATCGGATTCCAGTAGGAGTCTC | 7293.53 | 7294.09 | 253 |
| 162 | MSTN_H2_117-127_198-208 | AGTTTCAGAGAGTAGGAGTCTC | 7357.55 | 7357.72 | 254 |
| 163 | MSTN_H2_114-123_213-223 | CCTGGGTTCATGAGTCTCGAC | 6930.39 | 6930.41 | 255 |
| 164 | MSTN_H2_119-129_213-222 | CTGGGTTCATTTGTAGGAGTC | 7000.41 | 7000.29 | 256 |
| 165 | MSTN_HM2_119-129_191-203 | CAGAGATCGGATTTTGTAGGAGTC | 8042.78 | 8042.56 | 257 |
| 166 | MSTN_H2_117-127_131-141 | GCACAAACACTGTAGGAGTCTC | 7271.53 | 7271.82 | 258 |
| 167 | MSTN_H2_117-127_132-142 | TGCACAAACACGTAGGAGTCTC | 7271.53 | 7271.85 | 259 |
| 168 | MSTN_H2_129-140_214-223 | CCTGGGTTCACACAAACACTGT | 7222.51 | 7222.91 | 260 |

TABLE 1-continued

| PMO No. | Sequence name | Nucleotide sequence (5'→3') | Molecular weight (calculated) | Molecular weight (measured) | SEQ ID NO: |
|---|---|---|---|---|---|
| 169 | MSTN_H2_129-140_212-223 | CCTGGGTTCATGCACAAACACTGT | 7907.74 | 7907.65 | 261 |
| 170 | MSTN_HM2_129-140_192-203 | CAGAGATCGGATCACAAACACTGT | 7949.77 | 7949.90 | 262 |
| 171 | MSTN_HM2_129-140_193-204 | TCAGAGATCGGACACAAACACTGT | 7949.77 | 7950.17 | 263 |
| 172 | MSTN_H2_114-124_195-205 | TTCAGAGATCGGGAGTCTCGAC | 7318.54 | 7317.96 | 264 |
| 173 | MSTN_H2_114-123_214-223 | CCTGGGTTCAGAGTCTCGAC | 6600.28 | 6600.76 | 265 |
| 174 | MSTN_H2_117-127_180-190 | CCAGTATACCTGTAGGAGTCTC | 7253.51 | 7253.54 | 266 |
| 175 | MSTN_H2_117-127_182-192 | TTCCAGTATACGTAGGAGTCTC | 7268.52 | 7268.89 | 267 |
| 176 | MSTN_H2_193-204_212-223 | CCTGGGTTCATGTCAGAGATCGGA | 8003.77 | 8003.32 | 268 |
| 177 | MSTN_H2_191-202_212-223 | CCTGGGTTCATGAGAGATCGGATT | 8018.77 | 8018.85 | 269 |
| 178 | MSTN_H2_117-127_196-206 | TTTCAGAGATCGTAGGAGTCTC | 7308.53 | 7308.94 | 270 |
| 179 | MSTN_H2_114-124_128-138 | CAAACACTGTTGGAGTCTCGAC | 7262.52 | 7262.78 | 271 |
| 180 | MSTN_H2_114-124_129-139 | ACAAACACTGTGGAGTCTCGAC | 7271.53 | 7271.50 | 272 |
| 181 | MSTN_H2_117-126_215-223 | CCTGGGTTCTAGGAGTCTC | 6276.17 | 6276.10 | 273 |
| 182 | MSTN_H2_118-127_215-223 | CCTGGGTTCGTAGGAGTCT | 6316.18 | 6316.00 | 274 |
| 183 | MSTN_H2_117-125_215-223 | CCTGGGTTCAGGAGTCTC | 5946.06 | 5946.39 | 275 |
| 184 | MSTN_H2_118-126_215-223 | CCTGGGTTCTAGGAGTCT | 5961.06 | 5960.99 | 276 |
| 185 | MSTN_H2_117-128_281-292 | TTGGATTCAGGTTGTAGGAGTCTC | 8024.76 | 8024.64 | 277 |
| 186 | MSTN_H2_117-128_284-295 | AAGTTGGATTCATGTAGGAGTCTC | 8017.77 | 8017.74 | 278 |
| 187 | MSTN_H2_117-128_139-150 | TCAGGATTTGCATGTAGGAGTCTC | 7993.76 | 7994.08 | 279 |
| 188 | MSTN_H2_117-128_141-152 | TCTCAGGATTTGTGTAGGAGTCTC | 7984.75 | 7984.49 | 280 |
| 189 | MSTN_H2_117-127_190-200 | AGATCGGATTCGTAGGAGTCTC | 7333.54 | 7333.23 | 281 |
| 190 | MSTN_H2_117-127_193-203 | CAGAGATCGGAGTAGGAGTCTC | 7367.56 | 7368.05 | 282 |
| 191 | MSTN_H2_117-127_194-204 | TCAGAGATCGGGTAGGAGTCTC | 7358.55 | 7358.58 | 283 |
| 192 | MSTN_H2_179-190_212-223 | CCTGGGTTCATGCCAGTATACCTT | 7889.72 | 7889.74 | 284 |
| 193 | MSTN_H2_181-192_212-223 | CCTGGGTTCATGTTCCAGTATACC | 7889.72 | 7890.21 | 285 |
| 194 | MSTN_H2_212-223_267-278 | TTTGAGCCAATTCCTGGGTTCATG | 7944.74 | 7945.28 | 286 |
| 195 | MSTN_H2_212-223_269-280 | TGTTTGAGCCAACCTGGGTTCATG | 7969.75 | 7969.96 | 287 |
| 196 | MSTN_H2_212-223_345-356 | TCCTGGGAAGGTCCTGGGTTCATG | 8010.76 | 8010.35 | 288 |
| 197 | MSTN_H2_212-223_348-359 | TGGTCCTGGGAACCTGGGTTCATG | 8010.76 |  | 289 |
| 198 | MSTN_H2_117-126_196-205 | TTCAGAGATCTAGGAGTCTC | 6623.30 | 6622.99 | 371 |
| 199 | MSTN_H2_117-126_195-204 | TCAGAGATCGTAGGAGTCTC | 6648.31 | 6648.32 | 372 |
| 200 | MSTN_H2_117-126_194-203 | CAGAGATCGGTAGGAGTCTC | 6673.32 | 6673.28 | 373 |
| 201 | MSTN_HM2_118-128_196-206 | TTTCAGAGATCTGTAGGAGTCT | 7323.53 | 7323.56 | 374 |
| 202 | MSTN_HM2_118-128_195-205 | TTCAGAGATCGTGTAGGAGTCT | 7348.54 | 7348.26 | 375 |
| 203 | MSTN_H2_114-124_196-206 | TTTCAGAGATCGGAGTCTCGAC | 7293.53 | 7293.71 | 376 |
| 204 | MSTN_H2_117-128_195-204 | TCAGAGATCGTGTAGGAGTCTC | 7333.54 | 7333.02 | 377 |

TABLE 2

| PMO No. | Sequence name | Nucleotide sequence (5'→3') | Molecular weight (calculated) | Molecular weight (measured) | SEQ ID NO: |
|---|---|---|---|---|---|
| 205 | MSTN_H2_21-45 | AGAAGCAACATTTGGGTTTTCCATC | 8276.87 | 8276.83 | 1 |
| 206 | MSTN_H2_96-120 | TCTCGACGGGTCTCAAATATATCCA | 8221.85 | 8221.83 | 2 |
| 207 | MSTN_H2_116-140 | CACAAACACTGTTGTAGGAGTCTCG | 8286.87 | 8286.48 | 3 |
| 208 | MSTN_HM2_331-355 | CCTGGGAAGGTTACAGCAAGATCAT | 8335.90 | 8336.04 | 4 |
| 209 | MSTN_H2_96-115 | ACGGGTCTCAAATATATCCA | 6576.30 | 6575.60 | 5 |
| 210 | MSTN_H2_101-120 | TCTCGACGGGTCTCAAATAT | 6583.29 | 6583.07 | 6 |
| 211 | MSTN_HM2_171-195 | GGATTCCAGTATACCTTGTACCGTC | 8228.84 | 8228.81 | 7 |
| 212 | MSTN_HM2_166-190 | CCAGTATACCTTGTACCGTCTTTCA | 8163.82 | 8164.84 | 8 |
| 213 | MSTN_HM2_336-360 | CTGGTCCTGGGAAGGTTACAGCAAG | 8367.90 | 8367.65 | 9 |
| 214 | MSTN_HM2_341-365 | TTCTCCTGGTCCTGGGAAGGTTACA | 8284.85 | 8284.11 | 10 |
| 215 | MSTN_HM2_136-160 | TTGATGAGTCTCAGGATTTGCACAA | 8316.88 | 8316.35 | 11 |
| 216 | MSTN_H2_151-175 | CCGTCTTTCATAGGTTTGATGAGTC | 8274.85 | 8274.80 | 12 |
| 217 | MSTN_H2_1-25 | CCATCCACTTGCATTAGAAAATCAG | 8214.86 | 8215.09 | 13 |
| 218 | MSTN_HM2_346-370 | CCATCTTCTCCTGGTCCTGGGAAGG | 8245.84 | 8245.09 | 14 |
| 219 | MSTN_H2_141-165 | TAGGTTTGATGAGTCTCAGGATTTG | 8378.88 | 8378.39 | 15 |
| 220 | MSTN_H2_106-130 | GTTGTAGGAGTCTCGACGGGTCTCA | 8349.88 | 8349.83 | 16 |
| 221 | MSTN_H2_106-125 | AGGAGTCTCGACGGGTCTCA | 6649.31 | 6649.01 | 17 |
| 222 | MSTN_H2_116-135 | ACACTGTTGTAGGAGTCTCG | 6639.30 | 6639.41 | 18 |
| 223 | MSTN_H2_98-117 | CGACGGGTCTCAAATATATC | 6592.30 | 6592.25 | 19 |
| 224 | MSTN_H2_103-122 | AGTCTCGACGGGTCTCAAAT | 6608.30 | 6607.83 | 20 |
| 225 | MSTN_H2_113-132 | CTGTTGTAGGAGTCTCGACG | 6655.30 | 6655.45 | 21 |
| 226 | MSTN_H2_23-42 | AGCAACATTTGGGTTTTCCA | 6598.29 | 6598.57 | 22 |
| 227 | MSTN_H2_116-137 | AAACACTGTTGTAGGAGTCTCG | 7317.54 | 7317.18 | 23 |
| 228 | MSTN_HM2_121-145 | ATTTGCACAAACACTGTTGTAGGAG | 8325.89 | 8324.98 | 24 |
| 229 | MSTN_HM2_121-140 | CACAAACACTGTTGTAGGAG | 6641.32 | 6641.73 | 25 |
| 230 | MSTN_H2_111-135 | ACACTGTTGTAGGAGTCTCGACGGG | 8358.89 | 8358.77 | 26 |
| 231 | MSTN_H2_111-130 | GTTGTAGGAGTCTCGACGGG | 6720.32 | 6720.08 | 27 |
| 232 | MSTN_HM2_119-140 | CACAAACACTGTTGTAGGAGTC | 7286.54 | 7286.24 | 28 |
| 233 | MSTN_H2_21-40 | CAACATTTGGGTTTTCCATC | 6549.27 | 6548.67 | 29 |
| 234 | MSTN_H2_26-45 | AGAAGCAACATTTGGGTTTT | 6662.31 | 6662.77 | 30 |
| 235 | MSTN_H2_-10-15 | GCATTAGAAAATCAGCTATAAATGA | 8326.91 | 8326.50 | 31 |
| 236 | MSTN_H2_11-35 | TTTGGGTTTTCCATCCACTTGCATT | 8200.81 | 8200.79 | 32 |
| 237 | MSTN_H2_6-30 | GTTTTCCATCCACTTGCATTAGAAA | 8211.84 | 8211.40 | 33 |
| 238 | MSTN_H2_-5-20 | CACTTGCATTAGAAAATCAGCTATA | 8253.88 | 8253.71 | 34 |
| 239 | MSTN_H2_101-125 | AGGAGTCTCGACGGGTCTCAAATAT | 8326.89 | 8326.20 | 35 |
| 240 | MSTN_H2_112-136 | AACACTGTTGTAGGAGTCTCGACGG | 8342.89 | 8343.14 | 36 |
| 241 | MSTN_H2_113-137 | AAACACTGTTGTAGGAGTCTCGACG | 8326.89 | 8327.41 | 37 |
| 242 | MSTN_H2_115-139 | ACAAACACTGTTGTAGGAGTCTCGA | 8310.89 | 8310.85 | 38 |
| 243 | MSTN_H2_114-138 | CAAACACTGTTGTAGGAGTCTCGAC | 8286.87 | 8286.68 | 39 |

TABLE 2-continued

| PMO No. | Sequence name | Nucleotide sequence (5'→3') | Molecular weight (calculated) | Molecular weight (measured) | SEQ ID NO: |
|---|---|---|---|---|---|
| 244 | MSTN_H2_117-141 | GCACAAACACTGTTGTAGGAGTCTC | 8286.87 | 8287.41 | 40 |
| 245 | MSTN_HM2_118-142 | TGCACAAACACTGTTGTAGGAGTCT | 8301.88 | 8301.26 | 41 |
| 246 | MSTN_HM2_119-143 | TTGCACAAACACTGTTGTAGGAGTC | 8301.88 | 8301.89 | 42 |
| 247 | MSTN_HM2_120-144 | TTTGCACAAACACTGTTGTAGGAGT | 8316.88 | 8316.69 | 43 |
| 248 | MSTN_H2_91-115 | ACGGGTCTCAAATATATCCATAGTT | 8260.87 | 8260.78 | 44 |
| 249 | MSTN_H2_-3-22 | TCCACTTGCATTAGAAAATCAGCTA | 8229.86 | 8229.36 | 45 |
| 250 | MSTN_HM2_191-215 | CATGTCAAGTTTCAGAGATCGGATT | 8316.88 | 8317.25 | 46 |
| 251 | MSTN_H2_201-225 | TGCCTGGGTTCATGTCAAGTTTCAG | 8299.86 | 8299.68 | 47 |
| 252 | MSTN_H2_211-235 | CAAATACCAGTGCCTGGGTTCATGT | 8277.86 | 8277.30 | 48 |
| 253 | MSTN_H2_54-78 | CTTTATTGTATTGTATTTTAGAGCT | 8278.84 | 8278.45 | 49 |
| 254 | MSTN_H2_-4-21 | CCACTTGCATTAGAAAATCAGCTAT | 8229.86 | 8229.68 | 50 |
| 255 | MSTN_H2_-2-23 | ATCCACTTGCATTAGAAAATCAGCT | 8229.86 | 8229.37 | 51 |
| 256 | MSTN_H2_-1-24 | CATCCACTTGCATTAGAAAATCAGC | 8214.86 | 8214.95 | 52 |
| 257 | MSTN_H2_5-29 | TTTTCCATCCACTTGCATTAGAAAA | 8195.84 | 8194.80 | 53 |
| 258 | MSTN_H2_2-26 | TCCATCCACTTGCATTAGAAAATCA | 8189.85 | 8189.90 | 54 |
| 259 | MSTN_H2_3-27 | TTCCATCCACTTGCATTAGAAAATC | 8180.84 | 8181.54 | 55 |
| 260 | MSTN_H2_4-28 | TTTCCATCCACTTGCATTAGAAAAT | 8195.84 | 8196.94 | 56 |
| 261 | MSTN_H2_-7-18 | CTTGCATTAGAAAATCAGCTATAAA | 8277.89 | 8278.60 | 57 |
| 262 | MSTN_H2_8-32 | GGGTTTTCCATCCACTTGCATTAGA | 8243.84 | 8244.65 | 58 |
| 263 | MSTN_H2_117-138 | CAAACACTGTTGTAGGAGTCTC | 7277.53 | 7277.87 | 59 |
| 264 | MSTN_HM2_118-139 | ACAAACACTGTTGTAGGAGTCT | 7301.54 | 7302.04 | 60 |
| 265 | MSTN_H2_1-21 | CCACTTGCATTAGAAAATCAG | 6915.42 | 6915.68 | 61 |
| 266 | MSTN_H2_9-29 | TTTTCCATCCACTTGCATTAG | 6839.36 | 6840.60 | 62 |
| 267 | MSTN_H2_7-31 | GGTTTTCCATCCACTTGCATTAGAA | 8227.84 | 8226.95 | 63 |
| 268 | MSTN_H2_5-25 | CCATCCACTTGCATTAGAAAA | 6875.40 | 6875.44 | 64 |
| 269 | MSTN_H2_7-29 | TTTTCCATCCACTTGCATTAGAA | 7517.60 | 7517.22 | 65 |
| 270 | MSTN_H2_117-140 | CACAAACACTGTTGTAGGAGTCTC | 7931.75 | 7931.52 | 66 |
| 271 | MSTN_HM2_118-140 | CACAAACACTGTTGTAGGAGTCT | 7616.65 | 7616.24 | 67 |
| 272 | MSTN_H2_1-23 | ATCCACTTGCATTAGAAAATCAG | 7584.65 | 7584.03 | 68 |
| 273 | MSTN_H2_3-25 | CCATCCACTTGCATTAGAAAATC | 7520.62 | 7520.93 | 69 |
| 274 | MSTN_H2_5-27 | TTCCATCCACTTGCATTAGAAAA | 7535.62 | 7536.03 | 70 |
| 275 | MSTN_H2_93-117 | CGACGGGTCTCAAATATATCCATAG | 8270.87 | 8270.98 | 71 |
| 276 | MSTN_H2_98-122 | AGTCTCGACGGGTCTCAAATATATC | 8261.86 | 8262.37 | 72 |
| 277 | MSTN_H2_103-127 | GTAGGAGTCTCGACGGGTCTCAAAT | 8342.89 | 8343.04 | 73 |
| 278 | MSTN_H2_108-132 | CTGTTGTAGGAGTCTCGACGGGTCT | 8340.87 | 8340.17 | 74 |
| 279 | MSTN_H2_-1-25 | CCATCCACTTGCATTAGAAAATCAGC | 8529.97 | 8530.68 | 75 |
| 280 | MSTN_H2_1-26 | TCCATCCACTTGCATTAGAAAATCAG | 8544.97 | 8545.57 | 76 |
| 281 | MSTN_H2_116-139 | ACAAACACTGTTGTAGGAGTCTCG | 7971.77 | 7971.34 | 77 |
| 282 | MSTN_HM2_120-141 | GCACAAACACTGTTGTAGGAGT | 7326.55 | 7326.14 | 78 |

TABLE 2-continued

| PMO No. | Sequence name | Nucleotide sequence (5'→3') | Molecular weight (calculated) | Molecular weight (measured) | SEQ ID NO: |
|---|---|---|---|---|---|
| 283 | MSTN_HM2_119-141 | GCACAAACACTGTTGTAGGAGTC | 7641.66 | 7641.12 | 79 |
| 284 | MSTN_HM2_118-141 | GCACAAACACTGTTGTAGGAGTCT | 7971.77 | 7971.23 | 80 |
| 285 | MSTN_H2_117-139 | ACAAACACTGTTGTAGGAGTCTC | 7616.65 | 7616.99 | 81 |
| 286 | MSTN_HM2_120-140 | CACAAACACTGTTGTAGGAGT | 6971.43 | 6971.71 | 82 |
| 287 | MSTN_H2_117-129 | TTGTAGGAGTCTC | 4290.49 | 4290.46 | 83 |
| 288 | MSTN_H2_214-223 | CCTGGGTTCA | 3251.14 | 3251.29 | 84 |
| 289 | MSTN_HM2_130-140 | CACAAACACTG | 3552.27 | 3552.07 | 85 |
| 290 | MSTN_H2_117-127 | GTAGGAGTCTC | 3630.27 | 3630.01 | 86 |
| 291 | MSTN_H2_117-128 | TGTAGGAGTCTC | 3960.38 | 3960.15 | 87 |
| 292 | MSTN_H2_213-223 | CCTGGGTTCAT | 3581.25 | 3581.03 | 88 |
| 293 | MSTN_HM2_193-205 | TTCAGAGATCGGA | 4308.51 | 4308.49 | 89 |

TABLE 3

| PMO No. | Sequence name | Nucleotide sequence (5'→3') | Molecular weight (calculated) | Molecular weight (measured) | SEQ ID NO: |
|---|---|---|---|---|---|
| 294 | MSTN_M2_1-25 | CCATCCGCTTGCATTAGAAAGTCAG | 8246.86 | 8246.02 | 90 |
| 295 | MSTN_M2_116-140 | CACAAACACTGTTGTAGGAGTCTTG | 8301.88 | 8302.03 | 91 |
| 296 | MSTN_M2_21-45 | AAAAGCAACATTTGGGCTTGCCATC | 8270.87 | 8270.72 | 92 |
| 297 | MSTN_M2_117-127_214-223 | CCTGGGCTCAGTAGGAGTCTT | 6970.41 | 6969.99 | 290 |
| 298 | MSTN_M2_117-128_211-223 | CCTGGGCTCATGTTGTAGGAGTCTT | 8315.86 | 8315.79 | 291 |
| 299 | MSTN_M2_1-14_116-127 | GTAGGAGTCTTGCATTAGAAAGTCAG | 8721.02 | 8721.53 | 292 |
| 300 | MSTN_M2_117-129_213-223 | CCTGGGCTCATTTGTAGGAGTCTT | 7960.74 | 7960.75 | 293 |
| 301 | MSTN_M2_114-125_212-223 | CCTGGGCTCATGAGGAGTCTTGAC | 7979.75 | 7979.86 | 294 |
| 302 | MSTN_M2_117-127_130-140 | CACAAACACTGGTAGGAGTCTT | 7286.54 | 7286.69 | 295 |
| 303 | MSTN_H M2_169-181_348-360 | CTGGTCCTGGGAACTTGTACCGTCTT | 8590.95 | 8591.36 | 296 |
| 304 | MSTN_M2_117-128_213-223 | CCTGGGCTCATTGTAGGAGTCTT | 7630.63 | 7630.35 | 297 |
| 305 | MSTN_M2_117-125_211-223 | CCTGGGCTCATGTAGGAGTCTT | 7300.52 | 7300.50 | 298 |
| 306 | MSTN_M2_117-127_215-223 | CCTGGGCTCGTAGGAGTCTT | 6631.29 | 6631.39 | 299 |
| 307 | MSTN_M2_118-128_213-223 | CCTGGGCTCATTGTAGGAGTCT | 7300.52 | 7300.55 | 300 |
| 308 | MSTN_M2_117-128_214-225 | TGCCTGGGCTCATGTAGGAGTCTT | 7985.75 | 7985.85 | 301 |
| 309 | MSTN_M2_117-128_271-282 | GCTGTTTGAGCCTGTAGGAGTCTT | 8000.75 | 8000.54 | 302 |
| 310 | MSTN_M2_117-128_212-223 | CCTGGGCTCATGTAGGAGTCTT | 7985.75 | 7986.02 | 303 |
| 311 | MSTN_M2_117-128_160-171 | CTTTCATGGGTTTGTAGGAGTCTT | 7990.74 | 7990.86 | 304 |
| 312 | MSTN_M2_118-129_211-223 | CCTGGGCTCATGTTTGTAGGAGTCT | 8315.86 | 8316.08 | 305 |
| 313 | MSTN_M2_117-128_212-224 | GCCTGGGCTCATGTAGGAGTCTT | 8340.87 | 8341.12 | 306 |
| 314 | MSTN_M2_117-128_210-222 | CTGGGCTCATGTCTGTAGGAGTCTT | 8315.86 | 8316.11 | 307 |
| 315 | MSTN_M2_116-127_211-223 | CCTGGGCTCATGTAGGAGTCTTG | 8340.87 | 8341.16 | 308 |
| 316 | MSTN_H M2_118-128_180-191 | TCCAGTATACCTTGTAGGAGTCT | 7598.63 | 7598.40 | 309 |
| 317 | MSTN_M2_117-128_156-167 | CATGGGTTTGATTGTAGGAGTCTT | 8039.76 | | 310 |

TABLE 3-continued

| PMO No. | Sequence name | Nucleotide sequence (5'→3') | Molecular weight (calculated) | Molecular weight (measured) | SEQ ID NO: |
|---|---|---|---|---|---|
| 318 | MSTN_M2_117-128_278-289 | GATTCAGGCTGTTGTAGGAGTCTT | 8024.76 | 8026.40 | 311 |
| 319 | MSTN_HM2_164-176_353-365 | TTCTCCTGGTCCTACCGTCTTTCATG | 8476.91 | 8477.91 | 312 |
| 320 | MSTN_HM2_173-185_353-365 | TTCTCCTGGTCCTATACCTTGTACCG | 8485.92 | | 313 |
| 321 | MSTN_M2_90-102_117-128 | TGTAGGAGTCTTATATCCACAGTTG | 8307.87 | 8308.09 | 314 |
| 322 | MSTN_HM2_119-130_192-203 | CAGAGATCGGATGTTGTAGGAGTC | 8067.79 | 8067.22 | 315 |
| 323 | MSTN_HM2_118-129_191-202 | AGAGATCGGATTTTGTAGGAGTCT | 8057.78 | 8058.06 | 316 |
| 324 | MSTN_M2_117-127_194-206 | TTTCAGAGATCGGGTAGGAGTCTT | 8033.77 | 8033.56 | 317 |
| 325 | MSTN_HM2_118-128_194-206 | TTTCAGAGATCGGTGTAGGAGTCT | 8033.77 | 8033.04 | 318 |
| 326 | MSTN_HM2_120-130_194-206 | TTTCAGAGATCGGGTTGTAGGAGT | 8073.78 | 8074.04 | 319 |
| 327 | MSTN_HM2_119-129_190-202 | AGAGATCGGATTCTTGTAGGAGTC | 8042.78 | 8042.38 | 320 |
| 328 | MSTN_M2_117-128_182-193 | ATTCCAGTATACTGTAGGAGTCTT | 7952.75 | 7952.88 | 321 |
| 329 | MSTN_M2_117-128_180-191 | TCCAGTATACCTTGTAGGAGTCTT | 7928.74 | 7929.27 | 322 |
| 330 | MSTN_M2_117-128_192-205 | TTCAGAGATCGGATTGTAGGAGTCTT | 8703.00 | 8703.29 | 367 |
| 331 | MSTN_HM2_169-181_358-370 | CCATCTTCTCCTGCTTGTACCGTCTT | 8436.90 | 8437.03 | 368 |
| 332 | MSTN_M2_93-105_117-128 | TGTAGGAGTCTTGATATATCCACAG | 8316.88 | 8316.77 | 369 |
| 333 | MSTN_M2_117-128_192-203 | CAGAGATCGGATTGTAGGAGTCTT | 8042.78 | 8043.05 | 370 |

Example 1

4-{[(2S,6R)-6-(5-Methyl-2,4-dioxopyrimidin-1-yl)-4-tritylmorpholin-2-yl]methoxy}-4-oxobutanoic acid loaded on aminopolystyrene resin (Reference Example 1) or 4-{[(2S,6R)-6-(4-benzamido-2-oxopyrimidin-1-yl)-4-tritylmorpholin-2-yl]methoxy}-4-oxobutanoic acid loaded on aminopolystyrene resin (Reference Example 2) or 4-{[(2S,6R)-6-(6-benzamidopurin-9-yl)-4-tritylmorpholin-2-yl]methoxy}-4-oxobutanoic acid loaded on aminopolystyrene resin (Reference Example 3) or 4-{{(2S,6R)-6-{6-(2-cyanoethoxy)-2-[(2-phenoxyacetyl)amino]purin-9-yl}-4-tritylmorpholin-2-yl}methoxy}-4-oxobutanoic acid loaded on aminopolystyrene resin (Reference Example 4), each corresponding to the 5'-terminal base, was filled in an amount of 0.1 g into a reaction vessel equipped with a filter to initiate the following synthesis cycles using a peptide synthesizer (FOCUS). To give the nucleotide sequence of each compound indicated in Tables 1 to 4, a desired morpholino monomer compound was added in each coupling cycle (see Table 4 below).

TABLE 4

| Step | Reagent | Volume (mL/run) | Time (min/run) | Number of runs |
|---|---|---|---|---|
| 1 | Deblocking solution | 1.8 to 3 | 0.1 to 2 | 3 to 8 |
| 2 | Neutralizing solution | 2 to 10 | 1 | 3 |
| 3 | Dichloromethane | 2 to 10 | — | 5 |
| 4 | Activator solution | 1.8 to 3 | — | 1 |
| 5 | Monomer solution | 1 to 1.5 | — | 1 |
| 6 | Activator solution | 0.9 to 1.4 | — | 1 |
| 7 | Coupling reaction with the reagents charged in Steps 5 and 6 | | 120 to 180 | |
| 8 | Dichloromethane | 2 to 10 | — | 5 |
| 9 | Capping solution | 2 to 3 | 2 | 2 |
| 10 | Dichloromethane | 2 to 10 | — | 5 |

It should be noted that the deblocking solution used was prepared by dissolving a mixture of trifluoroacetic acid (2 equivalents) and triethylamine (1 equivalent) at a concentration of 3% (w/v) in a dichloromethane solution containing 1% (v/v) ethanol and 10% (v/v) 2,2,2-trifluoroethanol. The neutralizing solution used was prepared by dissolving N,N-diisopropylethylamine at a concentration of 5% (v/v) in a dichloromethane solution containing 25% (v/v) 2-propanol. The activator solution used was a 1,3-dimethyl-2-imidazolidinone solution containing 20% (v/v) N,N-diisopropylethylamine. The monomer solution used was prepared by dissolving a morpholino monomer compound at a concentration of 0.20 M in tetrahydrofuran. The capping solution used was prepared by dissolving acetic anhydride at 10% (v/v) and 2,6-lutidine at 15% (v/v) in dichloromethane.

The aminopolystyrene resin loaded with PMO synthesized as above was collected from the reaction vessel and dried at 30° C. for 2 hours or longer under reduced pressure. The dried PMO loaded on the aminopolystyrene resin was charged into a reaction vessel and 5 mL of 28% aqueous ammonia-ethanol (1/3) was added thereto, followed by standing at 55° C. for 16 hours. The aminopolystyrene resin was separated by filtration and washed with 3 mL of water-acetonitrile (1/1). After the resulting filtrate was mixed with ethanol (3 mL) and diethyl ether (35 mL), the mixture was centrifuged and then decanted to remove the supernatant, and the residue was dried under reduced pressure. The resulting residue was dissolved in 10 mL of a mixed solvent containing 20 mM aqueous ammonium acetate and acetonitrile (4/1), and then purified by reversed-phase HPLC. The conditions used are as indicated in Table 5 below.

TABLE 5

| Column | XBridge 5 μm C18 (Waters, φ19 × 50 mm, 1 CV = 14 mL) |
|---|---|
| Flow rate | 10 mL/minute |
| Column temperature | room temperature |
| Solution A | 20 mM aqueous ammonium acetate |
| Solution B | CH$_3$CN |
| Gradient | (B) conc. 20% → 50%/10 CV |

CV: column volume

The fractions were each analyzed to collect the desired product. The resulting solution was mixed with 0.1 M aqueous hydrochloric acid (4 mL) and allowed to stand for 2 hours. After the reaction, 1 M aqueous sodium hydroxide (0.4 mL) was added to neutralize the mixture, which was then filtered through a membrane filter (0.22 μm).

The resulting aqueous solution containing the desired product was made alkaline with 1 M aqueous sodium hydroxide (0.4 mL) and purified through an anion exchange resin column. The conditions used are as indicated in Table 6 below.

TABLE 6

| Column | Source 15Q (GE Healthcare, φ16 × 97 mm, 1 CV = 19.5 mL) |
|---|---|
| Flow rate | 10 mL/minute |
| Column temperature | room temperature |
| Solution A | 10 mM aqueous sodium hydroxide |
| Solution B | 10 mM aqueous sodium hydroxide, 1M aqueous sodium chloride |
| Gradient | (B) conc. 5% → 50%/20 CV |

The fractions were each analyzed (by HPLC) to obtain the desired product as an aqueous solution. The resulting aqueous solution was neutralized with 0.1 M phosphate buffer (pH 6.0) and then desalted by reversed-phase HPLC under the conditions shown in Table 7 below.

TABLE 7

| Column | YMC GEL C4 HG 10 μm (YMC, φ10 × 35 mm, 1 CV = 2.7 mL) |
|---|---|
| Flow rate | 10 mL/minute |
| Column temperature | room temperature |
| Solution A | water |
| Solution B | CH$_3$CN |
| Gradient | (B) conc. 0% → 50%/10 CV |

The desired product was collected and concentrated under reduced pressure. The resulting residue was dissolved in water and freeze-dried to obtain the desired compound as a white flocculent solid. The calculated and measured values of ESI-TOF-MS are shown in Tables 1 to 3.

Test Example 1

In Vitro Assay

Into $3 \times 10^5$ RD cells (human rhabdomyosarcoma cell line), the antisense oligomers shown in Table 1 or 3 were each transfected at 1, 3 or 10 μM through Nucleofector II (Lonza) using an Amaxa Cell Line Nucleofector Kit L. The program used was T-030.

After transfection, the cells were cultured for three nights at 37° C. under 5% CO$_2$ conditions in 2 mL of Dulbecco's Modified Eagle's Medium (DMEM) (SIGMA; the same applies hereinafter) containing 10% fetal calf serum (FCS) (Invitrogen).

After the cells were washed once with PBS (Nissui Pharmaceutical Co., Ltd., Japan; the same applies hereinafter), 350 μL of Buffer RLT (QIAGEN) containing 1% 2-mercaptoethanol (Nacalai Tesque, Inc., Japan) was added to the cells, and the cells were lysed by being allowed to stand at room temperature for a few minutes. The cell lysate was collected into a QIAshredder homogenizer (QIAGEN) and centrifuged at 20,400×g for 2 minutes to prepare a homogenate. The total RNA was extracted in accordance with the protocol attached to an RNeasy Mini Kit (QIAGEN). The concentration of the extracted total RNA was measured with a NanoDrop ND-1000 spectrophotometer (LMS Co., Ltd., Japan).

The extracted total RNA (10 ng) was used as a template to perform One-Step RT-PCR with a QIAGEN OneStep RT-PCR Kit (QIAGEN). A reaction solution was prepared in accordance with the protocol attached to the kit. The thermal cycler used was TaKaRa PCR Thermal Cycler Dice Touch (Takara Bio Inc., Japan). The RT-PCR program used is as shown below.

50° C. for 30 minutes: reverse transcription reaction

95° C. for 15 minutes: polymerase activation, reverse transcriptase inactivation

[94° C. for 30 seconds; 61° C. for 30 seconds; 72° C. for 1 minute]×27 cycles: PCR 72° C. for 7 minutes: final elongation reaction The nucleotide sequences of the forward and reverse primers used for RT-PCR are as shown below.

```
                                          (SEQ ID NO: 360)
Forward primer: 5'-TTCGTCTGGAAACAGCTCCT-3'

(SEQ ID NO: 361)
Reverse primer: 5'-AGAGGGTAACGACAGCATCG-3'
```

The above PCR reaction product (1 μL) was analyzed using a Bioanalyzer (Agilent).

The polynucleotide level "A" in the PCR amplicon with exon 2 skipping and the polynucleotide level "B" in the wild-type PCR amplicon were measured. Based on these measured values of "A" and "B," the skipping efficiency was determined according to the following equation.

Skipping efficiency (%)=$A/(A+B) \times 100$

Experimental Results

The results obtained are shown in FIGS. 1 to 14.

FIGS. 1 to 14 indicated that the antisense oligomer of the present invention effectively caused exon 2 skipping.

Test Example 2

In Vitro Assay

The same procedures as shown in Test Example 1 were repeated to conduct this experiment, except that $3 \times 10^5$ RD cells (human rhabdomyosarcoma cell line) were transfected with the oligomer of the present invention alone (PMO No. 100 (NMS-191), PMO No. 139 (NMS-233), PMO No. 79 (NMS-169) or PMO No. 114 (NMS-206)) or with either of the two unit oligomers constituting each oligomer or with a cocktail of the two unit oligomers constituting each oligomer through Nucleofector II (Lonza) using an Amaxa Cell Line Nucleofector Kit L. The pulse program used was T-030. Combinations of the sequences transfected are as shown below.

TABLE 8

| | Sequence | Transfection concentration |
|---|---|---|
| 1 | PMO No. 100 (NMS-191) alone, | 3 µM |
| | PMO No. 290 (NMS-258) alone, which is a unit oligomer constituting PMO No. 100 (NMS-191) | 3 µM |
| | PMO No. 289 (NMS-257) alone, which is a unit oligomer constituting PMO No. 100 (NMS-191) | 3 µM |
| | Cocktail of two unit oligomers constituting PMO No. 100 (NMS-191) (i.e., PMO No. 290 (NMS-258) and PMO No. 289 (NMS-257)) | 3 µM each |
| 2 | PMO No. 139 (NMS-233) alone | 1 µM |
| | PMO No. 290 (NMS-258) alone, which is a unit oligomer constituting PMO No. 139 (NMS-233) | 1 µM |
| | PMO No. 288 (NMS-237) alone, which is a unit oligomer constituting PMO No. 139 (NMS-233) | 1 µM |
| | Cocktail of two unit oligomers constituting PMO No. 139 (NMS-233) (i.e., PMO No. 290 (NMS-258) and PMO No. 288 (NMS-237)) | 1 µM each |
| 3 | PMO No. 79 (NMS-169) alone | 1 µM |
| | PMO No. 287 (NMS-236) alone, which is a unit oligomer constituting PMO No. 79 (NMS-169) | 1 µM |
| | PMO No. 293 (NMS-265) alone, which is a unit oligomer constituting PMO No. 79 (NMS-169) | 1 µM |
| | Cocktail of two unit oligomers constituting PMO No. 79 (NMS-169) (i.e., PMO No. 287 (NMS-236) and PMO No. 293 (NMS-265)) | 1 µM each |
| 4 | PMO No. 114 (NMS-206) alone | 1 µM |
| | PMO No. 287 (NMS-236) alone, which is a unit oligomer constituting PMO No. 114 (NMS-206) | 1 µM |
| | PMO No. 288 (NMS-237) alone, which is a unit oligomer constituting PMO No. 114 (NMS-206) | 1 µM |
| | Cocktail of two unit oligomers constituting PMO No. 114 (NMS-206) (i.e., PMO No. 287 (NMS-236) and PMO No. 288 (NMS-237)) | 1 µM each |
| 5 | PMO No. 114 (NMS-206) alone | 1 µM |
| | PMO No. 291 (NMS-263) alone, which is a unit oligomer constituting PMO No. 114 (NMS-206) | 1 µM |
| | PMO No. 292 (NMS-264) alone, which is a unit oligomer constituting PMO No. 114 (NMS-206) | 1 µM |
| | Cocktail of two unit oligomers constituting PMO No. 114 (NMS-206) (i.e., PMO No. 291 (NMS-263) and PMO No. 292 (NMS-264)) | 1 µM each |

Experimental Results

Figure 15:
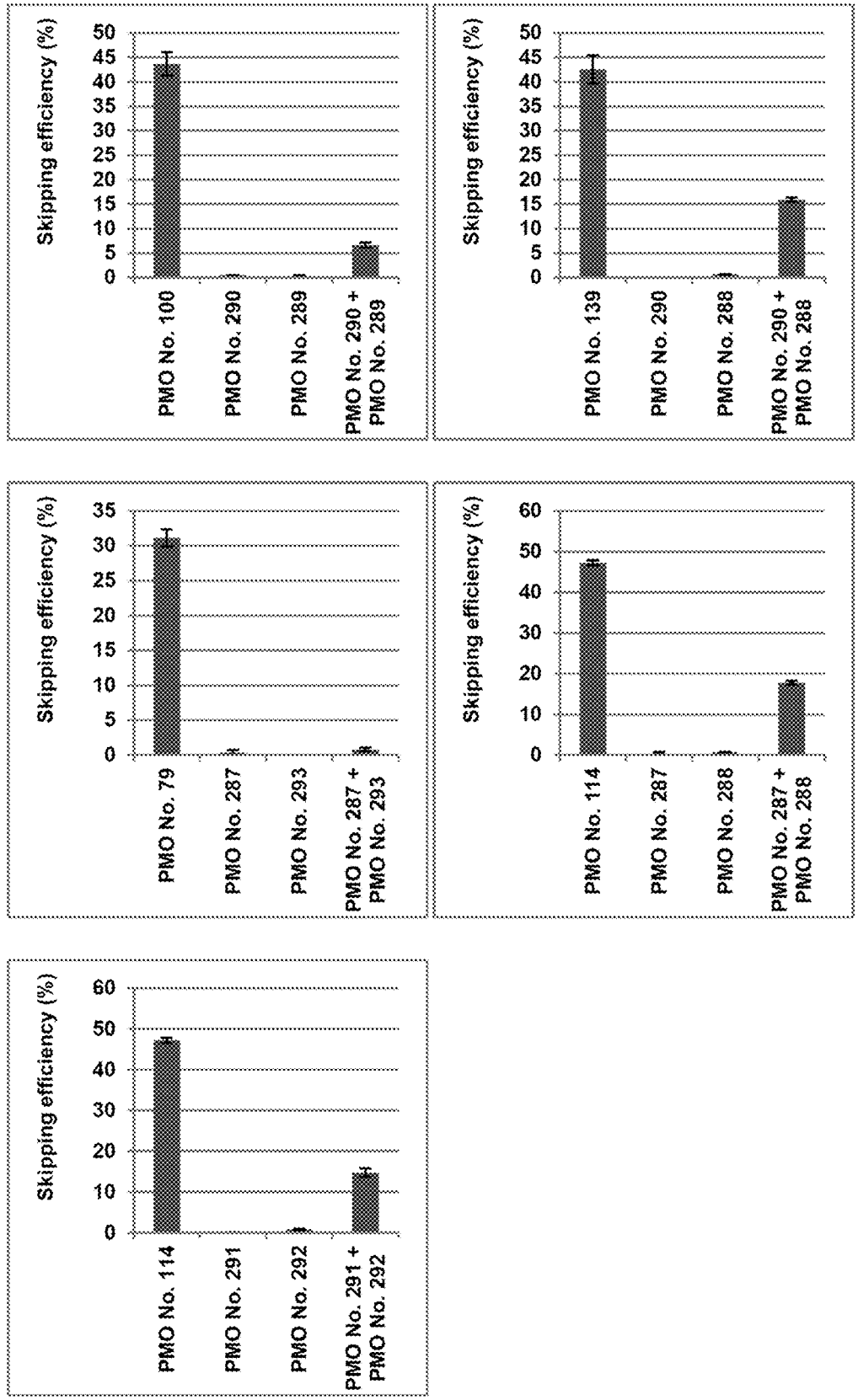
FIG. 15 shows the results of Test Example 2.

The results obtained are shown in FIG. 15. This experiment indicated that when compared to a cocktail of two antisense nucleic acids targeting different sites in exon 2 (i.e., PMO No. 290 (NMS-258) and PMO No. 289 (NMS-257), PMO No. 290 (NMS-258) and PMO No. 288 (NMS-237), PMO No. 287 (NMS-236) and PMO No. 293 (NMS-265), PMO No. 287 (NMS-236) and PMO No. 288 (NMS-237), or PMO No. 291 (NMS-263) and PMO No. 292 (NMS-264)), the oligomers of the present invention, i.e., PMO No. 100 (NMS-191), PMO No. 139 (NMS-233), PMO No. 79 (NMS-169) and PMO No. 114 (NMS-206), in which the respective two antisense nucleic acids are connected together, caused exon 2 skipping with higher efficiency.

The invention claimed is:

1. An antisense oligomer or pharmaceutically acceptable salt or hydrate thereof, wherein the antisense oligomer consists of any one nucleotide sequence selected from the group consisting of SEQ ID NO: 103 (NMS-48), SEQ ID NO: 116 (NMS-89), SEQ ID NO: 117 (NMS-90), SEQ ID NO: 120 (NMS-93), SEQ ID NO: 128 (NMS-101), SEQ ID NO: 131 (NMS-104), SEQ ID NO: 136 (NMS-113), SEQ ID NO: 137 (NMS-117), SEQ ID NO: 140 (NMS-123), SEQ ID NO: 145 (NMS-136), SEQ ID NO: 146 (NMS-139), SEQ ID NO: 147 (NMS-140), SEQ ID NO: 148 (NMS-141), SEQ ID NO: 149 (NMS-142), SEQ ID NO: 152 (NMS-145), SEQ ID NO: 155 (NMS-148), SEQ ID NO: 156 (NMS-149), SEQ ID NO: 157 (NMS-150), SEQ ID NO: 159 (NMS-152), SEQ ID NO: 162 (NMS-156), SEQ ID NO: 163 (NMS-157), SEQ ID NO: 165 (NMS-162), SEQ ID NO: 166 (NMS-163), SEQ ID NO: 167 (NMS-164), SEQ ID NO: 168 (NMS-166), SEQ ID NO: 169 (NMS-167), SEQ ID NO: 170 (NMS-168), SEQ ID NO: 171 (NMS-169), SEQ ID NO: 176 (NMS-174), SEQ ID NO: 177 (NMS-175), SEQ ID NO: 178 (NMS-176), SEQ ID NO: 179 (NMS-177), SEQ ID NO: 180 (NMS-178), SEQ ID NO: 183 (NMS-181), SEQ ID NO: 187 (NMS-185), SEQ ID NO: 189 (NMS-188), SEQ ID NO: 190 (NMS-189), SEQ ID NO: 191 (NMS-190), SEQ ID NO: 192 (NMS-191), SEQ ID NO: 193 (NMS-192), SEQ ID NO: 196 (NMS-195), SEQ ID NO: 199 (NMS-198), SEQ ID NO: 200 (NMS-199), SEQ ID NO: 201 (NMS-200), SEQ ID NO: 203 (NMS-202), SEQ ID NO: 204 (NMS-203), SEQ ID NO: 206 (NMS-206), SEQ ID NO: 208 (NMS-208), SEQ ID NO: 212 (NMS-212), SEQ ID NO: 213 (NMS-213), SEQ ID NO: 214 (NMS-214), SEQ ID NO: 215 (NMS-215), SEQ ID NO: 217 (NMS-217), SEQ ID NO: 225 (NMS-225), SEQ ID NO: 226 (NMS-228), SEQ ID NO: 228 (NMS-230), SEQ ID NO: 229 (NMS-231), SEQ ID NO: 231 (NMS-233), SEQ ID NO: 232 (NMS-234), SEQ ID NO: 233 (NMS-235), SEQ ID NO: 236 (NMS-240), SEQ ID NO: 237 (NMS-241), SEQ ID NO: 240 (NMS-244), SEQ ID NO: 243 (NMS-247), SEQ ID NO: 244 (NMS-248), SEQ ID NO: 245 (NMS-249), SEQ ID NO: 246 (NMS-250), SEQ ID NO: 247 (NMS-251), SEQ ID NO: 248 (NMS-252), SEQ ID NO: 252 (NMS-256), SEQ ID NO: 261 (NMS-272), SEQ ID NO: 273 (NMS-284), SEQ ID NO: 274 (NMS-285), SEQ ID NO: 275 (NMS-286), SEQ ID NO: 277 (NMS-297), SEQ ID NO: 95 (NMS-38), SEQ ID NO: 96 (NMS-39), SEQ ID NO: 107 (NMS-66), SEQ ID NO: 223 (NMS-223), SEQ ID NO: 234 (NMS-238), SEQ ID NO: 235 (NMS-239), SEQ ID NO: 242 (NMS-246), SEQ ID NO: 249 (NMS-253), SEQ ID NO: 250 (NMS-254), SEQ ID NO: 251 (NMS-255), SEQ ID NO: 257 (NMS-268), SEQ ID NO: 290 (NMS-280), SEQ ID NO: 291 (NMS-281), SEQ ID NO: 292 (NMS-282), SEQ ID NO: 293 (NMS-288), SEQ ID NO: 294 (NMS-289), SEQ ID NO: 295 (NMS-290), SEQ ID NO: 297 (NMS-292), SEQ ID NO: 298 (NMS-293), SEQ ID NO: 299 (NMS-294), SEQ ID NO: 300 (NMS-295), SEQ ID NO: 301 (NMS-298), SEQ ID NO: 302 (NMS-299), SEQ ID NO: 303 (NMS-300), SEQ ID NO: 304 (NMS-302), and SEQ ID NO: 305 (NMS-303).

2. The antisense oligomer or pharmaceutically acceptable salt or hydrate thereof according to claim 1, wherein the antisense oligomer is an oligonucleotide.

3. The antisense oligomer or pharmaceutically acceptable salt or hydrate thereof according to claim 2, wherein the oligonucleotide comprises at least one nucleotide having a modified sugar moiety and/or a modified phosphate bond moiety.

4. The antisense oligomer or pharmaceutically acceptable salt or hydrate thereof according to claim 3, wherein the modified sugar moiety is a ribose in which the —OH group at the 2'-position is substituted with any group selected from the group consisting of: OR, R, R'OR, SH, SR, $NH_2$, $NHR$, $NR_2$, $N_3$, CN, F, Cl, Br, and I (wherein R represents alkyl or aryl, and R' represents alkylene).

5. The antisense oligomer or pharmaceutically acceptable salt or hydrate thereof according to claim 3, wherein the modified phosphate bond moiety is any one selected from the group consisting of: a phosphorothioate bond, a phosphorodithioate bond, an alkylphosphonate bond, a phosphoroamidate bond, and a boranophosphate bond.

6. The antisense oligomer or pharmaceutically acceptable salt or hydrate thereof according to claim 1, wherein the antisense oligomer is a morpholino oligomer.

7. The antisense oligomer or pharmaceutically acceptable salt or hydrate thereof according to claim 6, wherein the morpholino oligomer is a phosphorodiamidate morpholino oligomer.

8. The antisense oligomer or pharmaceutically acceptable salt or hydrate thereof according to claim 6, wherein the 5'-terminal end of the morpholino oligomer is any one of the groups represented by chemical formulae (1) to (3) shown below:

[Formula 1]

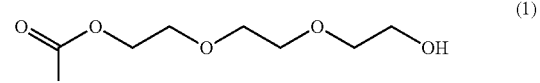

(1)

(2)

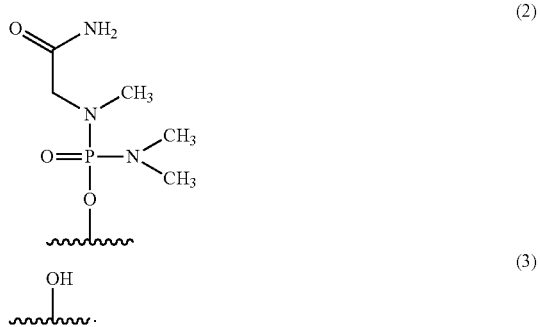

(3)

9. The antisense oligomer or pharmaceutically acceptable salt or hydrate thereof according to claim 1, wherein the antisense oligomer consists of any one nucleotide sequence selected from the group consisting of: SEQ ID NO: 171 (NMS-169), SEQ ID NO: 192 (NMS-191), SEQ ID NO: 245 (NMS-249), and SEQ ID NO: 231 (NMS-233).

10. A method for treating an amyotrophic disease or a muscle wasting disease, which comprises administering a subject in need of treating the amyotrophic disease or the muscle wasting disease with a therapeutically effective amount of the antisense oligomer or pharmaceutically acceptable salt or hydrate thereof according to claim 1.

11. The method according to claim 10, wherein the amyotrophic disease or the muscle wasting disease is muscular dystrophy.

12. The method according to claim 10, wherein the subject is a human subject.

* * * * *

```
                        SEQUENCE LISTING

<160> NUMBER OF SEQ ID NOS: 379

<210> SEQ ID NO 1
<211> LENGTH: 25
<212> TYPE: DNA
<213> ORGANISM: Artificial
<220> FEATURE:
<223> OTHER INFORMATION: Synthetic nucleic acid

<400> SEQUENCE: 1
agaagcaaca tttgggtttt ccatc                                           25

<210> SEQ ID NO 2
<211> LENGTH: 25
<212> TYPE: DNA
<213> ORGANISM: Artificial
<220> FEATURE:
<223> OTHER INFORMATION: Synthetic nucleic acid
```

<400> SEQUENCE: 2
tctcgacggg tctcaaatat atcca                                            25

<210> SEQ ID NO 3
<211> LENGTH: 25
<212> TYPE: DNA
<213> ORGANISM: Artificial
<220> FEATURE:
<223> OTHER INFORMATION: Synthetic nucleic acid

<400> SEQUENCE: 3
cacaaacact gttgtaggag tctcg                                            25

<210> SEQ ID NO 4
<211> LENGTH: 25
<212> TYPE: DNA
<213> ORGANISM: Artificial
<220> FEATURE:
<223> OTHER INFORMATION: Synthetic nucleic acid

<400> SEQUENCE: 4
cctgggaagg ttacagcaag atcat                                            25

<210> SEQ ID NO 5
<211> LENGTH: 20
<212> TYPE: DNA
<213> ORGANISM: Artificial
<220> FEATURE:
<223> OTHER INFORMATION: Synthetic nucleic acid

<400> SEQUENCE: 5
acgggtctca aatatatcca                                                  20

<210> SEQ ID NO 6
<211> LENGTH: 20
<212> TYPE: DNA
<213> ORGANISM: Artificial
<220> FEATURE:
<223> OTHER INFORMATION: Synthetic nucleic acid

<400> SEQUENCE: 6
tctcgacggg tctcaaatat                                                  20

<210> SEQ ID NO 7
<211> LENGTH: 25
<212> TYPE: DNA
<213> ORGANISM: Artificial
<220> FEATURE:
<223> OTHER INFORMATION: Synthetic nucleic acid

<400> SEQUENCE: 7
ggattccagt ataccttgta ccgtc                                            25

<210> SEQ ID NO 8
<211> LENGTH: 25
<212> TYPE: DNA
<213> ORGANISM: Artificial
<220> FEATURE:
<223> OTHER INFORMATION: Synthetic nucleic acid

<400> SEQUENCE: 8
ccagtatacc ttgtaccgtc tttca                                            25

<210> SEQ ID NO 9
<211> LENGTH: 25

```
<212> TYPE: DNA
<213> ORGANISM: Artificial
<220> FEATURE:
<223> OTHER INFORMATION: Synthetic nucleic acid

<400> SEQUENCE: 9
ctggtcctgg gaaggttaca gcaag                                            25

<210> SEQ ID NO 10
<211> LENGTH: 25
<212> TYPE: DNA
<213> ORGANISM: Artificial
<220> FEATURE:
<223> OTHER INFORMATION: Synthetic nucleic acid

<400> SEQUENCE: 10
ttctcctggt cctgggaagg ttaca                                            25

<210> SEQ ID NO 11
<211> LENGTH: 25
<212> TYPE: DNA
<213> ORGANISM: Artificial
<220> FEATURE:
<223> OTHER INFORMATION: Synthetic nucleic acid

<400> SEQUENCE: 11
ttgatgagtc tcaggatttg cacaa                                            25

<210> SEQ ID NO 12
<211> LENGTH: 25
<212> TYPE: DNA
<213> ORGANISM: Artificial
<220> FEATURE:
<223> OTHER INFORMATION: Synthetic nucleic acid

<400> SEQUENCE: 12
ccgtctttca taggtttgat gagtc                                            25

<210> SEQ ID NO 13
<211> LENGTH: 25
<212> TYPE: DNA
<213> ORGANISM: Artificial
<220> FEATURE:
<223> OTHER INFORMATION: Synthetic nucleic acid

<400> SEQUENCE: 13
ccatccactt gcattagaaa atcag                                            25

<210> SEQ ID NO 14
<211> LENGTH: 25
<212> TYPE: DNA
<213> ORGANISM: Artificial
<220> FEATURE:
<223> OTHER INFORMATION: Synthetic nucleic acid

<400> SEQUENCE: 14
ccatcttctc ctggtcctgg gaagg                                            25

<210> SEQ ID NO 15
<211> LENGTH: 25
<212> TYPE: DNA
<213> ORGANISM: Artificial
<220> FEATURE:
<223> OTHER INFORMATION: Synthetic nucleic acid

<400> SEQUENCE: 15
```
taggtttgat gagtctcagg atttg                          25

<210> SEQ ID NO 16
<211> LENGTH: 25
<212> TYPE: DNA
<213> ORGANISM: Artificial
<220> FEATURE:
<223> OTHER INFORMATION: Synthetic nucleic acid

<400> SEQUENCE: 16
gttgtaggag tctcgacggg tctca                          25

<210> SEQ ID NO 17
<211> LENGTH: 20
<212> TYPE: DNA
<213> ORGANISM: Artificial
<220> FEATURE:
<223> OTHER INFORMATION: Synthetic nucleic acid

<400> SEQUENCE: 17
aggagtctcg acgggtctca                                20

<210> SEQ ID NO 18
<211> LENGTH: 20
<212> TYPE: DNA
<213> ORGANISM: Artificial
<220> FEATURE:
<223> OTHER INFORMATION: Synthetic nucleic acid

<400> SEQUENCE: 18
acactgttgt aggagtctcg                                20

<210> SEQ ID NO 19
<211> LENGTH: 20
<212> TYPE: DNA
<213> ORGANISM: Artificial
<220> FEATURE:
<223> OTHER INFORMATION: Synthetic nucleic acid

<400> SEQUENCE: 19
cgacgggtct caaatatatc                                20

<210> SEQ ID NO 20
<211> LENGTH: 20
<212> TYPE: DNA
<213> ORGANISM: Artificial
<220> FEATURE:
<223> OTHER INFORMATION: Synthetic nucleic acid

<400> SEQUENCE: 20
agtctcgacg ggtctcaaat                                20

<210> SEQ ID NO 21
<211> LENGTH: 20
<212> TYPE: DNA
<213> ORGANISM: Artificial
<220> FEATURE:
<223> OTHER INFORMATION: Synthetic nucleic acid

<400> SEQUENCE: 21
ctgttgtagg agtctcgacg                                20

<210> SEQ ID NO 22
<211> LENGTH: 20
<212> TYPE: DNA
<213> ORGANISM: Artificial

```
<220> FEATURE:
<223> OTHER INFORMATION: Synthetic nucleic acid

<400> SEQUENCE: 22
agcaacattt gggttttcca                                                   20

<210> SEQ ID NO 23
<211> LENGTH: 22
<212> TYPE: DNA
<213> ORGANISM: Artificial
<220> FEATURE:
<223> OTHER INFORMATION: Synthetic nucleic acid

<400> SEQUENCE: 23
aaacactgtt gtaggagtct cg                                                22

<210> SEQ ID NO 24
<211> LENGTH: 25
<212> TYPE: DNA
<213> ORGANISM: Artificial
<220> FEATURE:
<223> OTHER INFORMATION: Synthetic nucleic acid

<400> SEQUENCE: 24
atttgcacaa acactgttgt aggag                                             25

<210> SEQ ID NO 25
<211> LENGTH: 20
<212> TYPE: DNA
<213> ORGANISM: Artificial
<220> FEATURE:
<223> OTHER INFORMATION: Synthetic nucleic acid

<400> SEQUENCE: 25
cacaaacact gttgtaggag                                                   20

<210> SEQ ID NO 26
<211> LENGTH: 25
<212> TYPE: DNA
<213> ORGANISM: Artificial
<220> FEATURE:
<223> OTHER INFORMATION: Synthetic nucleic acid

<400> SEQUENCE: 26
acactgttgt aggagtctcg acggg                                             25

<210> SEQ ID NO 27
<211> LENGTH: 20
<212> TYPE: DNA
<213> ORGANISM: Artificial
<220> FEATURE:
<223> OTHER INFORMATION: Synthetic nucleic acid

<400> SEQUENCE: 27
gttgtaggag tctcgacggg                                                   20

<210> SEQ ID NO 28
<211> LENGTH: 22
<212> TYPE: DNA
<213> ORGANISM: Artificial
<220> FEATURE:
<223> OTHER INFORMATION: Synthetic nucleic acid

<400> SEQUENCE: 28
cacaaacact gttgtaggag tc                                                22
```

```
<210> SEQ ID NO 29
<211> LENGTH: 20
<212> TYPE: DNA
<213> ORGANISM: Artificial
<220> FEATURE:
<223> OTHER INFORMATION: Synthetic nucleic acid

<400> SEQUENCE: 29
caacatttgg gttttccatc                                                   20

<210> SEQ ID NO 30
<211> LENGTH: 20
<212> TYPE: DNA
<213> ORGANISM: Artificial
<220> FEATURE:
<223> OTHER INFORMATION: Synthetic nucleic acid

<400> SEQUENCE: 30
agaagcaaca tttgggtttt                                                   20

<210> SEQ ID NO 31
<211> LENGTH: 25
<212> TYPE: DNA
<213> ORGANISM: Artificial
<220> FEATURE:
<223> OTHER INFORMATION: Synthetic nucleic acid

<400> SEQUENCE: 31
gcattagaaa atcagctata aatga                                             25

<210> SEQ ID NO 32
<211> LENGTH: 25
<212> TYPE: DNA
<213> ORGANISM: Artificial
<220> FEATURE:
<223> OTHER INFORMATION: Synthetic nucleic acid

<400> SEQUENCE: 32
tttgggtttt ccatccactt gcatt                                             25

<210> SEQ ID NO 33
<211> LENGTH: 25
<212> TYPE: DNA
<213> ORGANISM: Artificial
<220> FEATURE:
<223> OTHER INFORMATION: Synthetic nucleic acid

<400> SEQUENCE: 33
gttttccatc cacttgcatt agaaa                                             25

<210> SEQ ID NO 34
<211> LENGTH: 25
<212> TYPE: DNA
<213> ORGANISM: Artificial
<220> FEATURE:
<223> OTHER INFORMATION: Synthetic nucleic acid

<400> SEQUENCE: 34
cacttgcatt agaaaatcag ctata                                             25

<210> SEQ ID NO 35
<211> LENGTH: 25
<212> TYPE: DNA
<213> ORGANISM: Artificial
<220> FEATURE:
<223> OTHER INFORMATION: Synthetic nucleic acid
```

<400> SEQUENCE: 35
aggagtctcg acgggtctca aatat                               25

<210> SEQ ID NO 36
<211> LENGTH: 25
<212> TYPE: DNA
<213> ORGANISM: Artificial
<220> FEATURE:
<223> OTHER INFORMATION: Synthetic nucleic acid

<400> SEQUENCE: 36
aacactgttg taggagtctc gacgg                               25

<210> SEQ ID NO 37
<211> LENGTH: 25
<212> TYPE: DNA
<213> ORGANISM: Artificial
<220> FEATURE:
<223> OTHER INFORMATION: Synthetic nucleic acid

<400> SEQUENCE: 37
aaacactgtt gtaggagtct cgacg                               25

<210> SEQ ID NO 38
<211> LENGTH: 25
<212> TYPE: DNA
<213> ORGANISM: Artificial
<220> FEATURE:
<223> OTHER INFORMATION: Synthetic nucleic acid

<400> SEQUENCE: 38
acaaacactg ttgtaggagt ctcga                               25

<210> SEQ ID NO 39
<211> LENGTH: 25
<212> TYPE: DNA
<213> ORGANISM: Artificial
<220> FEATURE:
<223> OTHER INFORMATION: Synthetic nucleic acid

<400> SEQUENCE: 39
caaacactgt tgtaggagtc tcgac                               25

<210> SEQ ID NO 40
<211> LENGTH: 25
<212> TYPE: DNA
<213> ORGANISM: Artificial
<220> FEATURE:
<223> OTHER INFORMATION: Synthetic nucleic acid

<400> SEQUENCE: 40
gcacaaacac tgttgtagga gtctc                               25

<210> SEQ ID NO 41
<211> LENGTH: 25
<212> TYPE: DNA
<213> ORGANISM: Artificial
<220> FEATURE:
<223> OTHER INFORMATION: Synthetic nucleic acid

<400> SEQUENCE: 41
tgcacaaaca ctgttgtagg agtct                               25

<210> SEQ ID NO 42

```
<211> LENGTH: 25
<212> TYPE: DNA
<213> ORGANISM: Artificial
<220> FEATURE:
<223> OTHER INFORMATION: Synthetic nucleic acid

<400> SEQUENCE: 42
ttgcacaaac actgttgtag gagtc                                    25

<210> SEQ ID NO 43
<211> LENGTH: 25
<212> TYPE: DNA
<213> ORGANISM: Artificial
<220> FEATURE:
<223> OTHER INFORMATION: Synthetic nucleic acid

<400> SEQUENCE: 43
tttgcacaaa cactgttgta ggagt                                    25

<210> SEQ ID NO 44
<211> LENGTH: 25
<212> TYPE: DNA
<213> ORGANISM: Artificial
<220> FEATURE:
<223> OTHER INFORMATION: Synthetic nucleic acid

<400> SEQUENCE: 44
acgggtctca aatatatcca tagtt                                    25

<210> SEQ ID NO 45
<211> LENGTH: 25
<212> TYPE: DNA
<213> ORGANISM: Artificial
<220> FEATURE:
<223> OTHER INFORMATION: Synthetic nucleic acid

<400> SEQUENCE: 45
tccacttgca ttagaaaatc agcta                                    25

<210> SEQ ID NO 46
<211> LENGTH: 25
<212> TYPE: DNA
<213> ORGANISM: Artificial
<220> FEATURE:
<223> OTHER INFORMATION: Synthetic nucleic acid

<400> SEQUENCE: 46
catgtcaagt ttcagagatc ggatt                                    25

<210> SEQ ID NO 47
<211> LENGTH: 25
<212> TYPE: DNA
<213> ORGANISM: Artificial
<220> FEATURE:
<223> OTHER INFORMATION: Synthetic nucleic acid

<400> SEQUENCE: 47
tgcctgggtt catgtcaagt ttcag                                    25

<210> SEQ ID NO 48
<211> LENGTH: 25
<212> TYPE: DNA
<213> ORGANISM: Artificial
<220> FEATURE:
<223> OTHER INFORMATION: Synthetic nucleic acid

<400> SEQUENCE: 48
```
caaataccag tgcctgggtt catgt                                                 25

<210> SEQ ID NO 49
<211> LENGTH: 25
<212> TYPE: DNA
<213> ORGANISM: Artificial
<220> FEATURE:
<223> OTHER INFORMATION: Synthetic nucleic acid

<400> SEQUENCE: 49
ctttattgta ttgtatttta gagct                                                 25

<210> SEQ ID NO 50
<211> LENGTH: 25
<212> TYPE: DNA
<213> ORGANISM: Artificial
<220> FEATURE:
<223> OTHER INFORMATION: Synthetic nucleic acid

<400> SEQUENCE: 50
ccacttgcat tagaaaatca gctat                                                 25

<210> SEQ ID NO 51
<211> LENGTH: 25
<212> TYPE: DNA
<213> ORGANISM: Artificial
<220> FEATURE:
<223> OTHER INFORMATION: Synthetic nucleic acid

<400> SEQUENCE: 51
atccacttgc attagaaaat cagct                                                 25

<210> SEQ ID NO 52
<211> LENGTH: 25
<212> TYPE: DNA
<213> ORGANISM: Artificial
<220> FEATURE:
<223> OTHER INFORMATION: Synthetic nucleic acid

<400> SEQUENCE: 52
catccacttg cattagaaaa tcagc                                                 25

<210> SEQ ID NO 53
<211> LENGTH: 25
<212> TYPE: DNA
<213> ORGANISM: Artificial
<220> FEATURE:
<223> OTHER INFORMATION: Synthetic nucleic acid

<400> SEQUENCE: 53
ttttccatcc acttgcatta gaaaa                                                 25

<210> SEQ ID NO 54
<211> LENGTH: 25
<212> TYPE: DNA
<213> ORGANISM: Artificial
<220> FEATURE:
<223> OTHER INFORMATION: Synthetic nucleic acid

<400> SEQUENCE: 54
tccatccact tgcattagaa aatca                                                 25

<210> SEQ ID NO 55
<211> LENGTH: 25
<212> TYPE: DNA

```
<213> ORGANISM: Artificial
<220> FEATURE:
<223> OTHER INFORMATION: Synthetic nucleic acid

<400> SEQUENCE: 55
ttccatccac ttgcattaga aaatc                                            25

<210> SEQ ID NO 56
<211> LENGTH: 25
<212> TYPE: DNA
<213> ORGANISM: Artificial
<220> FEATURE:
<223> OTHER INFORMATION: Synthetic nucleic acid

<400> SEQUENCE: 56
tttccatcca cttgcattag aaaat                                            25

<210> SEQ ID NO 57
<211> LENGTH: 25
<212> TYPE: DNA
<213> ORGANISM: Artificial
<220> FEATURE:
<223> OTHER INFORMATION: Synthetic nucleic acid

<400> SEQUENCE: 57
cttgcattag aaaatcagct ataaa                                            25

<210> SEQ ID NO 58
<211> LENGTH: 25
<212> TYPE: DNA
<213> ORGANISM: Artificial
<220> FEATURE:
<223> OTHER INFORMATION: Synthetic nucleic acid

<400> SEQUENCE: 58
gggttttcca tccacttgca ttaga                                            25

<210> SEQ ID NO 59
<211> LENGTH: 22
<212> TYPE: DNA
<213> ORGANISM: Artificial
<220> FEATURE:
<223> OTHER INFORMATION: Synthetic nucleic acid

<400> SEQUENCE: 59
caaacactgt tgtaggagtc tc                                               22

<210> SEQ ID NO 60
<211> LENGTH: 22
<212> TYPE: DNA
<213> ORGANISM: Artificial
<220> FEATURE:
<223> OTHER INFORMATION: Synthetic nucleic acid

<400> SEQUENCE: 60
acaaacactg ttgtaggagt ct                                               22

<210> SEQ ID NO 61
<211> LENGTH: 21
<212> TYPE: DNA
<213> ORGANISM: Artificial
<220> FEATURE:
<223> OTHER INFORMATION: Synthetic nucleic acid

<400> SEQUENCE: 61
ccacttgcat tagaaaatca g                                                21
```

<210> SEQ ID NO 62
<211> LENGTH: 21
<212> TYPE: DNA
<213> ORGANISM: Artificial
<220> FEATURE:
<223> OTHER INFORMATION: Synthetic nucleic acid

<400> SEQUENCE: 62
ttttccatcc acttgcatta g                                                    21

<210> SEQ ID NO 63
<211> LENGTH: 25
<212> TYPE: DNA
<213> ORGANISM: Artificial
<220> FEATURE:
<223> OTHER INFORMATION: Synthetic nucleic acid

<400> SEQUENCE: 63
ggttttccat ccacttgcat tagaa                                                25

<210> SEQ ID NO 64
<211> LENGTH: 21
<212> TYPE: DNA
<213> ORGANISM: Artificial
<220> FEATURE:
<223> OTHER INFORMATION: Synthetic nucleic acid

<400> SEQUENCE: 64
ccatccactt gcattagaaa a                                                    21

<210> SEQ ID NO 65
<211> LENGTH: 23
<212> TYPE: DNA
<213> ORGANISM: Artificial
<220> FEATURE:
<223> OTHER INFORMATION: Synthetic nucleic acid

<400> SEQUENCE: 65
ttttccatcc acttgcatta gaa                                                  23

<210> SEQ ID NO 66
<211> LENGTH: 24
<212> TYPE: DNA
<213> ORGANISM: Artificial
<220> FEATURE:
<223> OTHER INFORMATION: Synthetic nucleic acid

<400> SEQUENCE: 66
cacaaacact gttgtaggag tctc                                                 24

<210> SEQ ID NO 67
<211> LENGTH: 23
<212> TYPE: DNA
<213> ORGANISM: Artificial
<220> FEATURE:
<223> OTHER INFORMATION: Synthetic nucleic acid

<400> SEQUENCE: 67
cacaaacact gttgtaggag tct                                                  23

<210> SEQ ID NO 68
<211> LENGTH: 23
<212> TYPE: DNA
<213> ORGANISM: Artificial
<220> FEATURE:

<223> OTHER INFORMATION: Synthetic nucleic acid

<400> SEQUENCE: 68
atccacttgc attagaaaat cag                                    23

<210> SEQ ID NO 69
<211> LENGTH: 23
<212> TYPE: DNA
<213> ORGANISM: Artificial
<220> FEATURE:
<223> OTHER INFORMATION: Synthetic nucleic acid

<400> SEQUENCE: 69
ccatccactt gcattagaaa atc                                    23

<210> SEQ ID NO 70
<211> LENGTH: 23
<212> TYPE: DNA
<213> ORGANISM: Artificial
<220> FEATURE:
<223> OTHER INFORMATION: Synthetic nucleic acid

<400> SEQUENCE: 70
ttccatccac ttgcattaga aaa                                    23

<210> SEQ ID NO 71
<211> LENGTH: 25
<212> TYPE: DNA
<213> ORGANISM: Artificial
<220> FEATURE:
<223> OTHER INFORMATION: Synthetic nucleic acid

<400> SEQUENCE: 71
cgacgggtct caaatatatc catag                                  25

<210> SEQ ID NO 72
<211> LENGTH: 25
<212> TYPE: DNA
<213> ORGANISM: Artificial
<220> FEATURE:
<223> OTHER INFORMATION: Synthetic nucleic acid

<400> SEQUENCE: 72
agtctcgacg ggtctcaaat atatc                                  25

<210> SEQ ID NO 73
<211> LENGTH: 25
<212> TYPE: DNA
<213> ORGANISM: Artificial
<220> FEATURE:
<223> OTHER INFORMATION: Synthetic nucleic acid

<400> SEQUENCE: 73
gtaggagtct cgacgggtct caaat                                  25

<210> SEQ ID NO 74
<211> LENGTH: 25
<212> TYPE: DNA
<213> ORGANISM: Artificial
<220> FEATURE:
<223> OTHER INFORMATION: Synthetic nucleic acid

<400> SEQUENCE: 74
ctgttgtagg agtctcgacg ggtct                                  25

<210> SEQ ID NO 75
<211> LENGTH: 26
<212> TYPE: DNA
<213> ORGANISM: Artificial
<220> FEATURE:
<223> OTHER INFORMATION: Synthetic nucleic acid

<400> SEQUENCE: 75
ccatccactt gcattagaaa atcagc                                        26

<210> SEQ ID NO 76
<211> LENGTH: 26
<212> TYPE: DNA
<213> ORGANISM: Artificial
<220> FEATURE:
<223> OTHER INFORMATION: Synthetic nucleic acid

<400> SEQUENCE: 76
tccatccact tgcattagaa aatcag                                        26

<210> SEQ ID NO 77
<211> LENGTH: 24
<212> TYPE: DNA
<213> ORGANISM: Artificial
<220> FEATURE:
<223> OTHER INFORMATION: Synthetic nucleic acid

<400> SEQUENCE: 77
acaaacactg ttgtaggagt ctcg                                          24

<210> SEQ ID NO 78
<211> LENGTH: 22
<212> TYPE: DNA
<213> ORGANISM: Artificial
<220> FEATURE:
<223> OTHER INFORMATION: Synthetic nucleic acid

<400> SEQUENCE: 78
gcacaaacac tgttgtagga gt                                            22

<210> SEQ ID NO 79
<211> LENGTH: 23
<212> TYPE: DNA
<213> ORGANISM: Artificial
<220> FEATURE:
<223> OTHER INFORMATION: Synthetic nucleic acid

<400> SEQUENCE: 79
gcacaaacac tgttgtagga gtc                                           23

<210> SEQ ID NO 80
<211> LENGTH: 24
<212> TYPE: DNA
<213> ORGANISM: Artificial
<220> FEATURE:
<223> OTHER INFORMATION: Synthetic nucleic acid

<400> SEQUENCE: 80
gcacaaacac tgttgtagga gtct                                          24

<210> SEQ ID NO 81
<211> LENGTH: 23
<212> TYPE: DNA
<213> ORGANISM: Artificial
<220> FEATURE:
<223> OTHER INFORMATION: Synthetic nucleic acid

<400> SEQUENCE: 81
acaaacactg ttgtaggagt ctc                                                23

<210> SEQ ID NO 82
<211> LENGTH: 21
<212> TYPE: DNA
<213> ORGANISM: Artificial
<220> FEATURE:
<223> OTHER INFORMATION: Synthetic nucleic acid

<400> SEQUENCE: 82
cacaaacact gttgtaggag t                                                  21

<210> SEQ ID NO 83
<211> LENGTH: 13
<212> TYPE: DNA
<213> ORGANISM: Artificial
<220> FEATURE:
<223> OTHER INFORMATION: Synthetic nucleic acid

<400> SEQUENCE: 83
ttgtaggagt ctc                                                           13

<210> SEQ ID NO 84
<211> LENGTH: 10
<212> TYPE: DNA
<213> ORGANISM: Artificial
<220> FEATURE:
<223> OTHER INFORMATION: Synthetic nucleic acid

<400> SEQUENCE: 84
cctgggttca                                                               10

<210> SEQ ID NO 85
<211> LENGTH: 11
<212> TYPE: DNA
<213> ORGANISM: Artificial
<220> FEATURE:
<223> OTHER INFORMATION: Synthetic nucleic acid

<400> SEQUENCE: 85
cacaaacact g                                                             11

<210> SEQ ID NO 86
<211> LENGTH: 11
<212> TYPE: DNA
<213> ORGANISM: Artificial
<220> FEATURE:
<223> OTHER INFORMATION: Synthetic nucleic acid

<400> SEQUENCE: 86
gtaggagtct c                                                             11

<210> SEQ ID NO 87
<211> LENGTH: 12
<212> TYPE: DNA
<213> ORGANISM: Artificial
<220> FEATURE:
<223> OTHER INFORMATION: Synthetic nucleic acid

<400> SEQUENCE: 87
tgtaggagtc tc                                                            12

<210> SEQ ID NO 88
<211> LENGTH: 11

```
<212> TYPE: DNA
<213> ORGANISM: Artificial
<220> FEATURE:
<223> OTHER INFORMATION: Synthetic nucleic acid

<400> SEQUENCE: 88
cctgggttca t                                                        11

<210> SEQ ID NO 89
<211> LENGTH: 13
<212> TYPE: DNA
<213> ORGANISM: Artificial
<220> FEATURE:
<223> OTHER INFORMATION: Synthetic nucleic acid

<400> SEQUENCE: 89
ttcagagatc gga                                                      13

<210> SEQ ID NO 90
<211> LENGTH: 25
<212> TYPE: DNA
<213> ORGANISM: Artificial
<220> FEATURE:
<223> OTHER INFORMATION: Synthetic nucleic acid

<400> SEQUENCE: 90
ccatccgctt gcattagaaa gtcag                                         25

<210> SEQ ID NO 91
<211> LENGTH: 25
<212> TYPE: DNA
<213> ORGANISM: Artificial
<220> FEATURE:
<223> OTHER INFORMATION: Synthetic nucleic acid

<400> SEQUENCE: 91
cacaaacact gttgtaggag tcttg                                         25

<210> SEQ ID NO 92
<211> LENGTH: 25
<212> TYPE: DNA
<213> ORGANISM: Artificial
<220> FEATURE:
<223> OTHER INFORMATION: Synthetic nucleic acid

<400> SEQUENCE: 92
aaaagcaaca tttgggcttg ccatc                                         25

<210> SEQ ID NO 93
<211> LENGTH: 26
<212> TYPE: DNA
<213> ORGANISM: Artificial
<220> FEATURE:
<223> OTHER INFORMATION: Synthetic nucleic acid

<400> SEQUENCE: 93
ttcataggtt tgacacaaac actgtt                                        26

<210> SEQ ID NO 94
<211> LENGTH: 26
<212> TYPE: DNA
<213> ORGANISM: Artificial
<220> FEATURE:
<223> OTHER INFORMATION: Synthetic nucleic acid

<400> SEQUENCE: 94
```
tgcctgggtt catcttgtac cgtctt 26

<210> SEQ ID NO 95
<211> LENGTH: 26
<212> TYPE: DNA
<213> ORGANISM: Artificial
<220> FEATURE:
<223> OTHER INFORMATION: Synthetic nucleic acid

<400> SEQUENCE: 95
tgggaaggtt acacttgtac cgtctt 26

<210> SEQ ID NO 96
<211> LENGTH: 26
<212> TYPE: DNA
<213> ORGANISM: Artificial
<220> FEATURE:
<223> OTHER INFORMATION: Synthetic nucleic acid

<400> SEQUENCE: 96
ttctcctggt cctcttgtac cgtctt 26

<210> SEQ ID NO 97
<211> LENGTH: 26
<212> TYPE: DNA
<213> ORGANISM: Artificial
<220> FEATURE:
<223> OTHER INFORMATION: Synthetic nucleic acid

<400> SEQUENCE: 97
cacaaacact gttcatccac ttgcat 26

<210> SEQ ID NO 98
<211> LENGTH: 26
<212> TYPE: DNA
<213> ORGANISM: Artificial
<220> FEATURE:
<223> OTHER INFORMATION: Synthetic nucleic acid

<400> SEQUENCE: 98
cacaaacact gtttaaattt aaagaa 26

<210> SEQ ID NO 99
<211> LENGTH: 26
<212> TYPE: DNA
<213> ORGANISM: Artificial
<220> FEATURE:
<223> OTHER INFORMATION: Synthetic nucleic acid

<400> SEQUENCE: 99
cacaaacact gttattttag agctaa 26

<210> SEQ ID NO 100
<211> LENGTH: 26
<212> TYPE: DNA
<213> ORGANISM: Artificial
<220> FEATURE:
<223> OTHER INFORMATION: Synthetic nucleic acid

<400> SEQUENCE: 100
tgtcaagttt cagcttgtac cgtctt 26

<210> SEQ ID NO 101
<211> LENGTH: 26
<212> TYPE: DNA
<213> ORGANISM: Artificial

```
<220> FEATURE:
<223> OTHER INFORMATION: Synthetic nucleic acid

<400> SEQUENCE: 101
cacaaacact gttttgggtt ttccat                                            26

<210> SEQ ID NO 102
<211> LENGTH: 26
<212> TYPE: DNA
<213> ORGANISM: Artificial
<220> FEATURE:
<223> OTHER INFORMATION: Synthetic nucleic acid

<400> SEQUENCE: 102
tggtcctggg aagcacaaac actgtt                                            26

<210> SEQ ID NO 103
<211> LENGTH: 26
<212> TYPE: DNA
<213> ORGANISM: Artificial
<220> FEATURE:
<223> OTHER INFORMATION: Synthetic nucleic acid

<400> SEQUENCE: 103
tgtaggagtc tcgcattaga aaatca                                            26

<210> SEQ ID NO 104
<211> LENGTH: 26
<212> TYPE: DNA
<213> ORGANISM: Artificial
<220> FEATURE:
<223> OTHER INFORMATION: Synthetic nucleic acid

<400> SEQUENCE: 104
cacaaacact gttgaagcaa catttg                                            26

<210> SEQ ID NO 105
<211> LENGTH: 26
<212> TYPE: DNA
<213> ORGANISM: Artificial
<220> FEATURE:
<223> OTHER INFORMATION: Synthetic nucleic acid

<400> SEQUENCE: 105
tgtaggagtc tcgcatccac ttgcat                                            26

<210> SEQ ID NO 106
<211> LENGTH: 26
<212> TYPE: DNA
<213> ORGANISM: Artificial
<220> FEATURE:
<223> OTHER INFORMATION: Synthetic nucleic acid

<400> SEQUENCE: 106
acagcaagat catcagtata ccttgt                                            26

<210> SEQ ID NO 107
<211> LENGTH: 26
<212> TYPE: DNA
<213> ORGANISM: Artificial
<220> FEATURE:
<223> OTHER INFORMATION: Synthetic nucleic acid

<400> SEQUENCE: 107
ctcctggtcc tggcagtata ccttgt                                            26
```

<210> SEQ ID NO 108
<211> LENGTH: 26
<212> TYPE: DNA
<213> ORGANISM: Artificial
<220> FEATURE:
<223> OTHER INFORMATION: Synthetic nucleic acid

<400> SEQUENCE: 108
cacaaacact gttcattaga aaatca                                          26

<210> SEQ ID NO 109
<211> LENGTH: 26
<212> TYPE: DNA
<213> ORGANISM: Artificial
<220> FEATURE:
<223> OTHER INFORMATION: Synthetic nucleic acid

<400> SEQUENCE: 109
cacaaacact gttttactac tttatt                                          26

<210> SEQ ID NO 110
<211> LENGTH: 26
<212> TYPE: DNA
<213> ORGANISM: Artificial
<220> FEATURE:
<223> OTHER INFORMATION: Synthetic nucleic acid

<400> SEQUENCE: 110
tgggaaggtt acacagtata ccttgt                                          26

<210> SEQ ID NO 111
<211> LENGTH: 26
<212> TYPE: DNA
<213> ORGANISM: Artificial
<220> FEATURE:
<223> OTHER INFORMATION: Synthetic nucleic acid

<400> SEQUENCE: 111
cacaaacact gttattgtat tgtatt                                          26

<210> SEQ ID NO 112
<211> LENGTH: 26
<212> TYPE: DNA
<213> ORGANISM: Artificial
<220> FEATURE:
<223> OTHER INFORMATION: Synthetic nucleic acid

<400> SEQUENCE: 112
cacaaacact gttagttggg ccttta                                          26

<210> SEQ ID NO 113
<211> LENGTH: 26
<212> TYPE: DNA
<213> ORGANISM: Artificial
<220> FEATURE:
<223> OTHER INFORMATION: Synthetic nucleic acid

<400> SEQUENCE: 113
tgttgtagga gtccattaga aaatca                                          26

<210> SEQ ID NO 114
<211> LENGTH: 26
<212> TYPE: DNA
<213> ORGANISM: Artificial
<220> FEATURE:
<223> OTHER INFORMATION: Synthetic nucleic acid

<400> SEQUENCE: 114
cactgttgta ggacattaga aaatca                                          26

<210> SEQ ID NO 115
<211> LENGTH: 26
<212> TYPE: DNA
<213> ORGANISM: Artificial
<220> FEATURE:
<223> OTHER INFORMATION: Synthetic nucleic acid

<400> SEQUENCE: 115
cacaaacact gttatatatc catagt                                          26

<210> SEQ ID NO 116
<211> LENGTH: 26
<212> TYPE: DNA
<213> ORGANISM: Artificial
<220> FEATURE:
<223> OTHER INFORMATION: Synthetic nucleic acid

<400> SEQUENCE: 116
cacaaacact gttcgggtct caaata                                          26

<210> SEQ ID NO 117
<211> LENGTH: 26
<212> TYPE: DNA
<213> ORGANISM: Artificial
<220> FEATURE:
<223> OTHER INFORMATION: Synthetic nucleic acid

<400> SEQUENCE: 117
tgtaggagtc tcgacttgca ttagaa                                          26

<210> SEQ ID NO 118
<211> LENGTH: 26
<212> TYPE: DNA
<213> ORGANISM: Artificial
<220> FEATURE:
<223> OTHER INFORMATION: Synthetic nucleic acid

<400> SEQUENCE: 118
aggagtctcg acgcattaga aaatca                                          26

<210> SEQ ID NO 119
<211> LENGTH: 26
<212> TYPE: DNA
<213> ORGANISM: Artificial
<220> FEATURE:
<223> OTHER INFORMATION: Synthetic nucleic acid

<400> SEQUENCE: 119
aaacactgtt gtacattaga aaatca                                          26

<210> SEQ ID NO 120
<211> LENGTH: 26
<212> TYPE: DNA
<213> ORGANISM: Artificial
<220> FEATURE:
<223> OTHER INFORMATION: Synthetic nucleic acid

<400> SEQUENCE: 120
cacaaacact gttggagtct cgacgg                                          26

<210> SEQ ID NO 121

```
<211> LENGTH: 26
<212> TYPE: DNA
<213> ORGANISM: Artificial
<220> FEATURE:
<223> OTHER INFORMATION: Synthetic nucleic acid

<400> SEQUENCE: 121
ccagtatacc ttggaagcaa catttg                                          26

<210> SEQ ID NO 122
<211> LENGTH: 26
<212> TYPE: DNA
<213> ORGANISM: Artificial
<220> FEATURE:
<223> OTHER INFORMATION: Synthetic nucleic acid

<400> SEQUENCE: 122
ttcagagatc ggagaagcaa catttg                                          26

<210> SEQ ID NO 123
<211> LENGTH: 26
<212> TYPE: DNA
<213> ORGANISM: Artificial
<220> FEATURE:
<223> OTHER INFORMATION: Synthetic nucleic acid

<400> SEQUENCE: 123
tggtcctggg aaggaagcaa catttg                                          26

<210> SEQ ID NO 124
<211> LENGTH: 26
<212> TYPE: DNA
<213> ORGANISM: Artificial
<220> FEATURE:
<223> OTHER INFORMATION: Synthetic nucleic acid

<400> SEQUENCE: 124
tggtcctggg aagttcagag atcgga                                          26

<210> SEQ ID NO 125
<211> LENGTH: 26
<212> TYPE: DNA
<213> ORGANISM: Artificial
<220> FEATURE:
<223> OTHER INFORMATION: Synthetic nucleic acid

<400> SEQUENCE: 125
tggtcctggg aagcattaga aaatca                                          26

<210> SEQ ID NO 126
<211> LENGTH: 26
<212> TYPE: DNA
<213> ORGANISM: Artificial
<220> FEATURE:
<223> OTHER INFORMATION: Synthetic nucleic acid

<400> SEQUENCE: 126
tgtaggagtc tcggaagcaa catttg                                          26

<210> SEQ ID NO 127
<211> LENGTH: 26
<212> TYPE: DNA
<213> ORGANISM: Artificial
<220> FEATURE:
<223> OTHER INFORMATION: Synthetic nucleic acid

<400> SEQUENCE: 127
```

-continued

```
ccagtatacc ttgtgtagga gtctcg                                        26

<210> SEQ ID NO 128
<211> LENGTH: 26
<212> TYPE: DNA
<213> ORGANISM: Artificial
<220> FEATURE:
<223> OTHER INFORMATION: Synthetic nucleic acid

<400> SEQUENCE: 128
tgtaggagtc tcgtgcatta gaaaat                                        26

<210> SEQ ID NO 129
<211> LENGTH: 26
<212> TYPE: DNA
<213> ORGANISM: Artificial
<220> FEATURE:
<223> OTHER INFORMATION: Synthetic nucleic acid

<400> SEQUENCE: 129
tgtaggagtc tcgccacttg cattag                                        26

<210> SEQ ID NO 130
<211> LENGTH: 26
<212> TYPE: DNA
<213> ORGANISM: Artificial
<220> FEATURE:
<223> OTHER INFORMATION: Synthetic nucleic acid

<400> SEQUENCE: 130
tgtaggagtc tcggaaaatc agctat                                        26

<210> SEQ ID NO 131
<211> LENGTH: 26
<212> TYPE: DNA
<213> ORGANISM: Artificial
<220> FEATURE:
<223> OTHER INFORMATION: Synthetic nucleic acid

<400> SEQUENCE: 131
tgtaggagtc tcgtagaaaa tcagct                                        26

<210> SEQ ID NO 132
<211> LENGTH: 26
<212> TYPE: DNA
<213> ORGANISM: Artificial
<220> FEATURE:
<223> OTHER INFORMATION: Synthetic nucleic acid

<400> SEQUENCE: 132
gaagcaacat ttgcattaga aaatca                                        26

<210> SEQ ID NO 133
<211> LENGTH: 26
<212> TYPE: DNA
<213> ORGANISM: Artificial
<220> FEATURE:
<223> OTHER INFORMATION: Synthetic nucleic acid

<400> SEQUENCE: 133
ccagtatacc ttgcattaga aaatca                                        26

<210> SEQ ID NO 134
<211> LENGTH: 24
<212> TYPE: DNA
```

-continued

<213> ORGANISM: Artificial
<220> FEATURE:
<223> OTHER INFORMATION: Synthetic nucleic acid

<400> SEQUENCE: 134
tgtaggagtc tccattagaa aatc                                              24

<210> SEQ ID NO 135
<211> LENGTH: 26
<212> TYPE: DNA
<213> ORGANISM: Artificial
<220> FEATURE:
<223> OTHER INFORMATION: Synthetic nucleic acid

<400> SEQUENCE: 135
ttcagagatc ggacattaga aaatca                                            26

<210> SEQ ID NO 136
<211> LENGTH: 26
<212> TYPE: DNA
<213> ORGANISM: Artificial
<220> FEATURE:
<223> OTHER INFORMATION: Synthetic nucleic acid

<400> SEQUENCE: 136
tggtcctggg aagtgtagga gtctcg                                            26

<210> SEQ ID NO 137
<211> LENGTH: 26
<212> TYPE: DNA
<213> ORGANISM: Artificial
<220> FEATURE:
<223> OTHER INFORMATION: Synthetic nucleic acid

<400> SEQUENCE: 137
ttcagagatc ggatgtagga gtctcg                                            26

<210> SEQ ID NO 138
<211> LENGTH: 24
<212> TYPE: DNA
<213> ORGANISM: Artificial
<220> FEATURE:
<223> OTHER INFORMATION: Synthetic nucleic acid

<400> SEQUENCE: 138
gtaggagtct cgattagaaa atca                                              24

<210> SEQ ID NO 139
<211> LENGTH: 24
<212> TYPE: DNA
<213> ORGANISM: Artificial
<220> FEATURE:
<223> OTHER INFORMATION: Synthetic nucleic acid

<400> SEQUENCE: 139
tgtaggagtc tcattagaaa atca                                              24

<210> SEQ ID NO 140
<211> LENGTH: 24
<212> TYPE: DNA
<213> ORGANISM: Artificial
<220> FEATURE:
<223> OTHER INFORMATION: Synthetic nucleic acid

<400> SEQUENCE: 140
gtaggagtct cgcattagaa aatc                                              24

<210> SEQ ID NO 141
<211> LENGTH: 26
<212> TYPE: DNA
<213> ORGANISM: Artificial
<220> FEATURE:
<223> OTHER INFORMATION: Synthetic nucleic acid

<400> SEQUENCE: 141
cgggtctcaa atacattaga aaatca                                          26

<210> SEQ ID NO 142
<211> LENGTH: 26
<212> TYPE: DNA
<213> ORGANISM: Artificial
<220> FEATURE:
<223> OTHER INFORMATION: Synthetic nucleic acid

<400> SEQUENCE: 142
tcgacgggtc tcacattaga aaatca                                          26

<210> SEQ ID NO 143
<211> LENGTH: 26
<212> TYPE: DNA
<213> ORGANISM: Artificial
<220> FEATURE:
<223> OTHER INFORMATION: Synthetic nucleic acid

<400> SEQUENCE: 143
agtctcgacg ggtcattaga aaatca                                          26

<210> SEQ ID NO 144
<211> LENGTH: 26
<212> TYPE: DNA
<213> ORGANISM: Artificial
<220> FEATURE:
<223> OTHER INFORMATION: Synthetic nucleic acid

<400> SEQUENCE: 144
cacaaacact gtttcgacgg gtctca                                          26

<210> SEQ ID NO 145
<211> LENGTH: 26
<212> TYPE: DNA
<213> ORGANISM: Artificial
<220> FEATURE:
<223> OTHER INFORMATION: Synthetic nucleic acid

<400> SEQUENCE: 145
cacaaacact gttgtctcga cgggtc                                          26

<210> SEQ ID NO 146
<211> LENGTH: 26
<212> TYPE: DNA
<213> ORGANISM: Artificial
<220> FEATURE:
<223> OTHER INFORMATION: Synthetic nucleic acid

<400> SEQUENCE: 146
tgtaggagtc tcgttagaaa atcagc                                          26

<210> SEQ ID NO 147
<211> LENGTH: 26
<212> TYPE: DNA
<213> ORGANISM: Artificial
<220> FEATURE:

<223> OTHER INFORMATION: Synthetic nucleic acid

<400> SEQUENCE: 147
tgtaggagtc tcgattagaa aatcag                                           26

<210> SEQ ID NO 148
<211> LENGTH: 26
<212> TYPE: DNA
<213> ORGANISM: Artificial
<220> FEATURE:
<223> OTHER INFORMATION: Synthetic nucleic acid

<400> SEQUENCE: 148
gtaggagtct cgcattagaa aatcag                                           26

<210> SEQ ID NO 149
<211> LENGTH: 26
<212> TYPE: DNA
<213> ORGANISM: Artificial
<220> FEATURE:
<223> OTHER INFORMATION: Synthetic nucleic acid

<400> SEQUENCE: 149
taggagtctc gcattagaaa atcagc                                           26

<210> SEQ ID NO 150
<211> LENGTH: 26
<212> TYPE: DNA
<213> ORGANISM: Artificial
<220> FEATURE:
<223> OTHER INFORMATION: Synthetic nucleic acid

<400> SEQUENCE: 150
ttgtaggagt ctccattaga aaatca                                           26

<210> SEQ ID NO 151
<211> LENGTH: 26
<212> TYPE: DNA
<213> ORGANISM: Artificial
<220> FEATURE:
<223> OTHER INFORMATION: Synthetic nucleic acid

<400> SEQUENCE: 151
gttgtaggag tctcattaga aaatca                                           26

<210> SEQ ID NO 152
<211> LENGTH: 26
<212> TYPE: DNA
<213> ORGANISM: Artificial
<220> FEATURE:
<223> OTHER INFORMATION: Synthetic nucleic acid

<400> SEQUENCE: 152
tgtaggagtc tcggcattag aaaatc                                           26

<210> SEQ ID NO 153
<211> LENGTH: 26
<212> TYPE: DNA
<213> ORGANISM: Artificial
<220> FEATURE:
<223> OTHER INFORMATION: Synthetic nucleic acid

<400> SEQUENCE: 153
taggagtctc gaccattaga aaatca                                           26

<210> SEQ ID NO 154
<211> LENGTH: 26
<212> TYPE: DNA
<213> ORGANISM: Artificial
<220> FEATURE:
<223> OTHER INFORMATION: Synthetic nucleic acid

<400> SEQUENCE: 154
gtaggagtct cgacattaga aaatca                                       26

<210> SEQ ID NO 155
<211> LENGTH: 26
<212> TYPE: DNA
<213> ORGANISM: Artificial
<220> FEATURE:
<223> OTHER INFORMATION: Synthetic nucleic acid

<400> SEQUENCE: 155
gtaggagtct cgagcattag aaaatc                                       26

<210> SEQ ID NO 156
<211> LENGTH: 26
<212> TYPE: DNA
<213> ORGANISM: Artificial
<220> FEATURE:
<223> OTHER INFORMATION: Synthetic nucleic acid

<400> SEQUENCE: 156
ttgtaggagt ctcgcattag aaaatc                                       26

<210> SEQ ID NO 157
<211> LENGTH: 26
<212> TYPE: DNA
<213> ORGANISM: Artificial
<220> FEATURE:
<223> OTHER INFORMATION: Synthetic nucleic acid

<400> SEQUENCE: 157
tgcctgggtt cattgtagga gtctcg                                       26

<210> SEQ ID NO 158
<211> LENGTH: 26
<212> TYPE: DNA
<213> ORGANISM: Artificial
<220> FEATURE:
<223> OTHER INFORMATION: Synthetic nucleic acid

<400> SEQUENCE: 158
tgtttgagcc aattgtagga gtctcg                                       26

<210> SEQ ID NO 159
<211> LENGTH: 26
<212> TYPE: DNA
<213> ORGANISM: Artificial
<220> FEATURE:
<223> OTHER INFORMATION: Synthetic nucleic acid

<400> SEQUENCE: 159
gtaggagtct cgaattagaa aatcag                                       26

<210> SEQ ID NO 160
<211> LENGTH: 26
<212> TYPE: DNA
<213> ORGANISM: Artificial
<220> FEATURE:
<223> OTHER INFORMATION: Synthetic nucleic acid

```
<400> SEQUENCE: 160
ttgtaggagt ctcattagaa aatcag                                        26

<210> SEQ ID NO 161
<211> LENGTH: 25
<212> TYPE: DNA
<213> ORGANISM: Artificial
<220> FEATURE:
<223> OTHER INFORMATION: Synthetic nucleic acid

<400> SEQUENCE: 161
tgtaggagtc tcgattagaa aatca                                         25

<210> SEQ ID NO 162
<211> LENGTH: 25
<212> TYPE: DNA
<213> ORGANISM: Artificial
<220> FEATURE:
<223> OTHER INFORMATION: Synthetic nucleic acid

<400> SEQUENCE: 162
tgtaggagtc tcgcattaga aaatc                                         25

<210> SEQ ID NO 163
<211> LENGTH: 25
<212> TYPE: DNA
<213> ORGANISM: Artificial
<220> FEATURE:
<223> OTHER INFORMATION: Synthetic nucleic acid

<400> SEQUENCE: 163
gtaggagtct cgcattagaa aatca                                         25

<210> SEQ ID NO 164
<211> LENGTH: 25
<212> TYPE: DNA
<213> ORGANISM: Artificial
<220> FEATURE:
<223> OTHER INFORMATION: Synthetic nucleic acid

<400> SEQUENCE: 164
tgtaggagtc tccattagaa aatca                                         25

<210> SEQ ID NO 165
<211> LENGTH: 24
<212> TYPE: DNA
<213> ORGANISM: Artificial
<220> FEATURE:
<223> OTHER INFORMATION: Synthetic nucleic acid

<400> SEQUENCE: 165
cagagatcgg attgtaggag tctc                                          24

<210> SEQ ID NO 166
<211> LENGTH: 24
<212> TYPE: DNA
<213> ORGANISM: Artificial
<220> FEATURE:
<223> OTHER INFORMATION: Synthetic nucleic acid

<400> SEQUENCE: 166
tcagagatcg gatgtaggag tctc                                          24

<210> SEQ ID NO 167
<211> LENGTH: 24
```

```
<212> TYPE: DNA
<213> ORGANISM: Artificial
<220> FEATURE:
<223> OTHER INFORMATION: Synthetic nucleic acid

<400> SEQUENCE: 167
ttcagagatc ggtgtaggag tctc                                    24

<210> SEQ ID NO 168
<211> LENGTH: 25
<212> TYPE: DNA
<213> ORGANISM: Artificial
<220> FEATURE:
<223> OTHER INFORMATION: Synthetic nucleic acid

<400> SEQUENCE: 168
ttcagagatc ggtaggagtc tcgac                                   25

<210> SEQ ID NO 169
<211> LENGTH: 26
<212> TYPE: DNA
<213> ORGANISM: Artificial
<220> FEATURE:
<223> OTHER INFORMATION: Synthetic nucleic acid

<400> SEQUENCE: 169
cagagatcgg attgtaggag tctcga                                  26

<210> SEQ ID NO 170
<211> LENGTH: 25
<212> TYPE: DNA
<213> ORGANISM: Artificial
<220> FEATURE:
<223> OTHER INFORMATION: Synthetic nucleic acid

<400> SEQUENCE: 170
tcagagatcg gataggagtc tcgac                                   25

<210> SEQ ID NO 171
<211> LENGTH: 26
<212> TYPE: DNA
<213> ORGANISM: Artificial
<220> FEATURE:
<223> OTHER INFORMATION: Synthetic nucleic acid

<400> SEQUENCE: 171
ttcagagatc ggattgtagg agtctc                                  26

<210> SEQ ID NO 172
<211> LENGTH: 22
<212> TYPE: DNA
<213> ORGANISM: Artificial
<220> FEATURE:
<223> OTHER INFORMATION: Synthetic nucleic acid

<400> SEQUENCE: 172
aggagtctcg cattagaaaa tc                                      22

<210> SEQ ID NO 173
<211> LENGTH: 24
<212> TYPE: DNA
<213> ORGANISM: Artificial
<220> FEATURE:
<223> OTHER INFORMATION: Synthetic nucleic acid

<400> SEQUENCE: 173
```
aggagtctcg agcattagaa aatc                                            24

<210> SEQ ID NO 174
<211> LENGTH: 24
<212> TYPE: DNA
<213> ORGANISM: Artificial
<220> FEATURE:
<223> OTHER INFORMATION: Synthetic nucleic acid

<400> SEQUENCE: 174
gtaggagtct cgtagaaaat cagc                                            24

<210> SEQ ID NO 175
<211> LENGTH: 24
<212> TYPE: DNA
<213> ORGANISM: Artificial
<220> FEATURE:
<223> OTHER INFORMATION: Synthetic nucleic acid

<400> SEQUENCE: 175
aggagtctcg attagaaaat cagc                                            24

<210> SEQ ID NO 176
<211> LENGTH: 25
<212> TYPE: DNA
<213> ORGANISM: Artificial
<220> FEATURE:
<223> OTHER INFORMATION: Synthetic nucleic acid

<400> SEQUENCE: 176
gtaggagtct cggcattaga aaatc                                           25

<210> SEQ ID NO 177
<211> LENGTH: 25
<212> TYPE: DNA
<213> ORGANISM: Artificial
<220> FEATURE:
<223> OTHER INFORMATION: Synthetic nucleic acid

<400> SEQUENCE: 177
gtaggagtct cgttagaaaa tcagc                                           25

<210> SEQ ID NO 178
<211> LENGTH: 24
<212> TYPE: DNA
<213> ORGANISM: Artificial
<220> FEATURE:
<223> OTHER INFORMATION: Synthetic nucleic acid

<400> SEQUENCE: 178
tgcctgggtt catgtaggag tctc                                            24

<210> SEQ ID NO 179
<211> LENGTH: 24
<212> TYPE: DNA
<213> ORGANISM: Artificial
<220> FEATURE:
<223> OTHER INFORMATION: Synthetic nucleic acid

<400> SEQUENCE: 179
cagtgcctgg gttgtaggag tctc                                            24

<210> SEQ ID NO 180
<211> LENGTH: 24
<212> TYPE: DNA
<213> ORGANISM: Artificial

```
<220> FEATURE:
<223> OTHER INFORMATION: Synthetic nucleic acid

<400> SEQUENCE: 180
taggagtctc gcattagaaa atca                                         24

<210> SEQ ID NO 181
<211> LENGTH: 24
<212> TYPE: DNA
<213> ORGANISM: Artificial
<220> FEATURE:
<223> OTHER INFORMATION: Synthetic nucleic acid

<400> SEQUENCE: 181
taggagtctc gttagaaaat cagc                                         24

<210> SEQ ID NO 182
<211> LENGTH: 25
<212> TYPE: DNA
<213> ORGANISM: Artificial
<220> FEATURE:
<223> OTHER INFORMATION: Synthetic nucleic acid

<400> SEQUENCE: 182
taggagtctc gcattagaaa tcagc                                        25

<210> SEQ ID NO 183
<211> LENGTH: 26
<212> TYPE: DNA
<213> ORGANISM: Artificial
<220> FEATURE:
<223> OTHER INFORMATION: Synthetic nucleic acid

<400> SEQUENCE: 183
ggtcctggga aggttgtagg agtctc                                       26

<210> SEQ ID NO 184
<211> LENGTH: 22
<212> TYPE: DNA
<213> ORGANISM: Artificial
<220> FEATURE:
<223> OTHER INFORMATION: Synthetic nucleic acid

<400> SEQUENCE: 184
taggagtctc gcattagaaa at                                           22

<210> SEQ ID NO 185
<211> LENGTH: 23
<212> TYPE: DNA
<213> ORGANISM: Artificial
<220> FEATURE:
<223> OTHER INFORMATION: Synthetic nucleic acid

<400> SEQUENCE: 185
taggagtctc gcattagaaa atc                                          23

<210> SEQ ID NO 186
<211> LENGTH: 24
<212> TYPE: DNA
<213> ORGANISM: Artificial
<220> FEATURE:
<223> OTHER INFORMATION: Synthetic nucleic acid

<400> SEQUENCE: 186
taggagtctc ggcattagaa aatc                                         24
```

<210> SEQ ID NO 187
<211> LENGTH: 24
<212> TYPE: DNA
<213> ORGANISM: Artificial
<220> FEATURE:
<223> OTHER INFORMATION: Synthetic nucleic acid

<400> SEQUENCE: 187
tcctgggaag gttgtaggag tctc                                          24

<210> SEQ ID NO 188
<211> LENGTH: 24
<212> TYPE: DNA
<213> ORGANISM: Artificial
<220> FEATURE:
<223> OTHER INFORMATION: Synthetic nucleic acid

<400> SEQUENCE: 188
ttcagagatc ggaggagtct cgac                                          24

<210> SEQ ID NO 189
<211> LENGTH: 24
<212> TYPE: DNA
<213> ORGANISM: Artificial
<220> FEATURE:
<223> OTHER INFORMATION: Synthetic nucleic acid

<400> SEQUENCE: 189
cacaaacact gtaggagtct cgac                                          24

<210> SEQ ID NO 190
<211> LENGTH: 24
<212> TYPE: DNA
<213> ORGANISM: Artificial
<220> FEATURE:
<223> OTHER INFORMATION: Synthetic nucleic acid

<400> SEQUENCE: 190
cacaaacact gttaggagtc tcga                                          24

<210> SEQ ID NO 191
<211> LENGTH: 22
<212> TYPE: DNA
<213> ORGANISM: Artificial
<220> FEATURE:
<223> OTHER INFORMATION: Synthetic nucleic acid

<400> SEQUENCE: 191
cacaaacact gttaggagtc tc                                            22

<210> SEQ ID NO 192
<211> LENGTH: 22
<212> TYPE: DNA
<213> ORGANISM: Artificial
<220> FEATURE:
<223> OTHER INFORMATION: Synthetic nucleic acid

<400> SEQUENCE: 192
cacaaacact ggtaggagtc tc                                            22

<210> SEQ ID NO 193
<211> LENGTH: 23
<212> TYPE: DNA
<213> ORGANISM: Artificial
<220> FEATURE:
<223> OTHER INFORMATION: Synthetic nucleic acid

<400> SEQUENCE: 193
cacaaacact gtgtaggagt ctc                                              23

<210> SEQ ID NO 194
<211> LENGTH: 22
<212> TYPE: DNA
<213> ORGANISM: Artificial
<220> FEATURE:
<223> OTHER INFORMATION: Synthetic nucleic acid

<400> SEQUENCE: 194
agagatcgga tgtaggagtc tc                                               22

<210> SEQ ID NO 195
<211> LENGTH: 22
<212> TYPE: DNA
<213> ORGANISM: Artificial
<220> FEATURE:
<223> OTHER INFORMATION: Synthetic nucleic acid

<400> SEQUENCE: 195
ttcagagatc ggtaggagtc tc                                               22

<210> SEQ ID NO 196
<211> LENGTH: 25
<212> TYPE: DNA
<213> ORGANISM: Artificial
<220> FEATURE:
<223> OTHER INFORMATION: Synthetic nucleic acid

<400> SEQUENCE: 196
tgcctgggtt cattgtagga gtctc                                            25

<210> SEQ ID NO 197
<211> LENGTH: 25
<212> TYPE: DNA
<213> ORGANISM: Artificial
<220> FEATURE:
<223> OTHER INFORMATION: Synthetic nucleic acid

<400> SEQUENCE: 197
tgcctgggtt cataggagtc tcgac                                            25

<210> SEQ ID NO 198
<211> LENGTH: 24
<212> TYPE: DNA
<213> ORGANISM: Artificial
<220> FEATURE:
<223> OTHER INFORMATION: Synthetic nucleic acid

<400> SEQUENCE: 198
tcctgggaag gtaggagtct cgac                                             24

<210> SEQ ID NO 199
<211> LENGTH: 24
<212> TYPE: DNA
<213> ORGANISM: Artificial
<220> FEATURE:
<223> OTHER INFORMATION: Synthetic nucleic acid

<400> SEQUENCE: 199
tggtcctggg aatgtaggag tctc                                             24

<210> SEQ ID NO 200

```
<211> LENGTH: 24
<212> TYPE: DNA
<213> ORGANISM: Artificial
<220> FEATURE:
<223> OTHER INFORMATION: Synthetic nucleic acid

<400> SEQUENCE: 200
ctgggttcat gtaggagtct cgac                                          24

<210> SEQ ID NO 201
<211> LENGTH: 24
<212> TYPE: DNA
<213> ORGANISM: Artificial
<220> FEATURE:
<223> OTHER INFORMATION: Synthetic nucleic acid

<400> SEQUENCE: 201
ctgggttcat gttgtaggag tctc                                          24

<210> SEQ ID NO 202
<211> LENGTH: 23
<212> TYPE: DNA
<213> ORGANISM: Artificial
<220> FEATURE:
<223> OTHER INFORMATION: Synthetic nucleic acid

<400> SEQUENCE: 202
cacaaacact gtaggagtct cga                                           23

<210> SEQ ID NO 203
<211> LENGTH: 21
<212> TYPE: DNA
<213> ORGANISM: Artificial
<220> FEATURE:
<223> OTHER INFORMATION: Synthetic nucleic acid

<400> SEQUENCE: 203
cacaaacact gtaggagtct c                                             21

<210> SEQ ID NO 204
<211> LENGTH: 25
<212> TYPE: DNA
<213> ORGANISM: Artificial
<220> FEATURE:
<223> OTHER INFORMATION: Synthetic nucleic acid

<400> SEQUENCE: 204
ttcagagatc ggatgtagga gtctc                                         25

<210> SEQ ID NO 205
<211> LENGTH: 23
<212> TYPE: DNA
<213> ORGANISM: Artificial
<220> FEATURE:
<223> OTHER INFORMATION: Synthetic nucleic acid

<400> SEQUENCE: 205
tccatccact tgagaaaatc agc                                           23

<210> SEQ ID NO 206
<211> LENGTH: 23
<212> TYPE: DNA
<213> ORGANISM: Artificial
<220> FEATURE:
<223> OTHER INFORMATION: Synthetic nucleic acid

<400> SEQUENCE: 206
```
cctgggttca ttgtaggagt ctc                                               23

<210> SEQ ID NO 207
<211> LENGTH: 22
<212> TYPE: DNA
<213> ORGANISM: Artificial
<220> FEATURE:
<223> OTHER INFORMATION: Synthetic nucleic acid

<400> SEQUENCE: 207
tgcctgggtt catgtaggag tc                                                22

<210> SEQ ID NO 208
<211> LENGTH: 22
<212> TYPE: DNA
<213> ORGANISM: Artificial
<220> FEATURE:
<223> OTHER INFORMATION: Synthetic nucleic acid

<400> SEQUENCE: 208
cctgggttca tgtaggagtc tc                                                22

<210> SEQ ID NO 209
<211> LENGTH: 22
<212> TYPE: DNA
<213> ORGANISM: Artificial
<220> FEATURE:
<223> OTHER INFORMATION: Synthetic nucleic acid

<400> SEQUENCE: 209
aggagtctcg aagaaaatca gc                                                22

<210> SEQ ID NO 210
<211> LENGTH: 22
<212> TYPE: DNA
<213> ORGANISM: Artificial
<220> FEATURE:
<223> OTHER INFORMATION: Synthetic nucleic acid

<400> SEQUENCE: 210
taggagtctc gagaaaatca gc                                                22

<210> SEQ ID NO 211
<211> LENGTH: 22
<212> TYPE: DNA
<213> ORGANISM: Artificial
<220> FEATURE:
<223> OTHER INFORMATION: Synthetic nucleic acid

<400> SEQUENCE: 211
taggagtctc gattagaaaa tc                                                22

<210> SEQ ID NO 212
<211> LENGTH: 24
<212> TYPE: DNA
<213> ORGANISM: Artificial
<220> FEATURE:
<223> OTHER INFORMATION: Synthetic nucleic acid

<400> SEQUENCE: 212
tgggttcatg tctgtaggag tctc                                              24

<210> SEQ ID NO 213
<211> LENGTH: 24
<212> TYPE: DNA

<213> ORGANISM: Artificial
<220> FEATURE:
<223> OTHER INFORMATION: Synthetic nucleic acid

<400> SEQUENCE: 213
cctgggttca tgtgtaggag tctc    24

<210> SEQ ID NO 214
<211> LENGTH: 23
<212> TYPE: DNA
<213> ORGANISM: Artificial
<220> FEATURE:
<223> OTHER INFORMATION: Synthetic nucleic acid

<400> SEQUENCE: 214
tgggttcatg ttgtaggagt ctc    23

<210> SEQ ID NO 215
<211> LENGTH: 23
<212> TYPE: DNA
<213> ORGANISM: Artificial
<220> FEATURE:
<223> OTHER INFORMATION: Synthetic nucleic acid

<400> SEQUENCE: 215
ctgggttcat gttgtaggag tct    23

<210> SEQ ID NO 216
<211> LENGTH: 23
<212> TYPE: DNA
<213> ORGANISM: Artificial
<220> FEATURE:
<223> OTHER INFORMATION: Synthetic nucleic acid

<400> SEQUENCE: 216
ctgggttcat gtgtaggagt ctc    23

<210> SEQ ID NO 217
<211> LENGTH: 25
<212> TYPE: DNA
<213> ORGANISM: Artificial
<220> FEATURE:
<223> OTHER INFORMATION: Synthetic nucleic acid

<400> SEQUENCE: 217
tcagagatcg gattgtagga gtctc    25

<210> SEQ ID NO 218
<211> LENGTH: 22
<212> TYPE: DNA
<213> ORGANISM: Artificial
<220> FEATURE:
<223> OTHER INFORMATION: Synthetic nucleic acid

<400> SEQUENCE: 218
ctgggttcat tgtaggagtc tc    22

<210> SEQ ID NO 219
<211> LENGTH: 23
<212> TYPE: DNA
<213> ORGANISM: Artificial
<220> FEATURE:
<223> OTHER INFORMATION: Synthetic nucleic acid

<400> SEQUENCE: 219
ctgggttcat ttgtaggagt ctc    23

<210> SEQ ID NO 220
<211> LENGTH: 22
<212> TYPE: DNA
<213> ORGANISM: Artificial
<220> FEATURE:
<223> OTHER INFORMATION: Synthetic nucleic acid

<400> SEQUENCE: 220
ctgggttcat gttaggagtc tc                                              22

<210> SEQ ID NO 221
<211> LENGTH: 24
<212> TYPE: DNA
<213> ORGANISM: Artificial
<220> FEATURE:
<223> OTHER INFORMATION: Synthetic nucleic acid

<400> SEQUENCE: 221
tgggttcatg tcaggagtct cgac                                            24

<210> SEQ ID NO 222
<211> LENGTH: 24
<212> TYPE: DNA
<213> ORGANISM: Artificial
<220> FEATURE:
<223> OTHER INFORMATION: Synthetic nucleic acid

<400> SEQUENCE: 222
agagatcgga tttgtaggag tctc                                            24

<210> SEQ ID NO 223
<211> LENGTH: 21
<212> TYPE: DNA
<213> ORGANISM: Artificial
<220> FEATURE:
<223> OTHER INFORMATION: Synthetic nucleic acid

<400> SEQUENCE: 223
cacaaacact ggtaggagtc t                                               21

<210> SEQ ID NO 224
<211> LENGTH: 21
<212> TYPE: DNA
<213> ORGANISM: Artificial
<220> FEATURE:
<223> OTHER INFORMATION: Synthetic nucleic acid

<400> SEQUENCE: 224
acaaacactg gtaggagtct c                                               21

<210> SEQ ID NO 225
<211> LENGTH: 24
<212> TYPE: DNA
<213> ORGANISM: Artificial
<220> FEATURE:
<223> OTHER INFORMATION: Synthetic nucleic acid

<400> SEQUENCE: 225
cctgggttca tgaggagtct cgac                                            24

<210> SEQ ID NO 226
<211> LENGTH: 22
<212> TYPE: DNA
<213> ORGANISM: Artificial
<220> FEATURE:

-continued

<223> OTHER INFORMATION: Synthetic nucleic acid

<400> SEQUENCE: 226
cctgggttca ttgtaggagt ct                                              22

<210> SEQ ID NO 227
<211> LENGTH: 21
<212> TYPE: DNA
<213> ORGANISM: Artificial
<220> FEATURE:
<223> OTHER INFORMATION: Synthetic nucleic acid

<400> SEQUENCE: 227
ctgggttcat tgtaggagtc t                                               21

<210> SEQ ID NO 228
<211> LENGTH: 21
<212> TYPE: DNA
<213> ORGANISM: Artificial
<220> FEATURE:
<223> OTHER INFORMATION: Synthetic nucleic acid

<400> SEQUENCE: 228
cctgggttca ttgtaggagt c                                               21

<210> SEQ ID NO 229
<211> LENGTH: 21
<212> TYPE: DNA
<213> ORGANISM: Artificial
<220> FEATURE:
<223> OTHER INFORMATION: Synthetic nucleic acid

<400> SEQUENCE: 229
cctgggttca ttaggagtct c                                               21

<210> SEQ ID NO 230
<211> LENGTH: 21
<212> TYPE: DNA
<213> ORGANISM: Artificial
<220> FEATURE:
<223> OTHER INFORMATION: Synthetic nucleic acid

<400> SEQUENCE: 230
ctgggttcat gtaggagtct c                                               21

<210> SEQ ID NO 231
<211> LENGTH: 21
<212> TYPE: DNA
<213> ORGANISM: Artificial
<220> FEATURE:
<223> OTHER INFORMATION: Synthetic nucleic acid

<400> SEQUENCE: 231
cctgggttca gtaggagtct c                                               21

<210> SEQ ID NO 232
<211> LENGTH: 22
<212> TYPE: DNA
<213> ORGANISM: Artificial
<220> FEATURE:
<223> OTHER INFORMATION: Synthetic nucleic acid

<400> SEQUENCE: 232
cacaaacact tgtaggagtc tc                                              22

```
<210> SEQ ID NO 233
<211> LENGTH: 22
<212> TYPE: DNA
<213> ORGANISM: Artificial
<220> FEATURE:
<223> OTHER INFORMATION: Synthetic nucleic acid

<400> SEQUENCE: 233
cacaaacact gaggagtctc ga                                              22

<210> SEQ ID NO 234
<211> LENGTH: 24
<212> TYPE: DNA
<213> ORGANISM: Artificial
<220> FEATURE:
<223> OTHER INFORMATION: Synthetic nucleic acid

<400> SEQUENCE: 234
tttcagagat cggttgtagg agtc                                            24

<210> SEQ ID NO 235
<211> LENGTH: 24
<212> TYPE: DNA
<213> ORGANISM: Artificial
<220> FEATURE:
<223> OTHER INFORMATION: Synthetic nucleic acid

<400> SEQUENCE: 235
tcagagatcg gattgtagga gtct                                            24

<210> SEQ ID NO 236
<211> LENGTH: 22
<212> TYPE: DNA
<213> ORGANISM: Artificial
<220> FEATURE:
<223> OTHER INFORMATION: Synthetic nucleic acid

<400> SEQUENCE: 236
cacaaacact gggagtctcg ac                                              22

<210> SEQ ID NO 237
<211> LENGTH: 23
<212> TYPE: DNA
<213> ORGANISM: Artificial
<220> FEATURE:
<223> OTHER INFORMATION: Synthetic nucleic acid

<400> SEQUENCE: 237
tgggttcatg taggagtctc gac                                             23

<210> SEQ ID NO 238
<211> LENGTH: 23
<212> TYPE: DNA
<213> ORGANISM: Artificial
<220> FEATURE:
<223> OTHER INFORMATION: Synthetic nucleic acid

<400> SEQUENCE: 238
ctgggttcat taggagtctc gac                                             23

<210> SEQ ID NO 239
<211> LENGTH: 24
<212> TYPE: DNA
<213> ORGANISM: Artificial
<220> FEATURE:
<223> OTHER INFORMATION: Synthetic nucleic acid
```

<400> SEQUENCE: 239
tttcagagat cgtgtaggag tctc                                          24

<210> SEQ ID NO 240
<211> LENGTH: 25
<212> TYPE: DNA
<213> ORGANISM: Artificial
<220> FEATURE:
<223> OTHER INFORMATION: Synthetic nucleic acid

<400> SEQUENCE: 240
cctgggttca tgttgtagga gtctc                                         25

<210> SEQ ID NO 241
<211> LENGTH: 20
<212> TYPE: DNA
<213> ORGANISM: Artificial
<220> FEATURE:
<223> OTHER INFORMATION: Synthetic nucleic acid

<400> SEQUENCE: 241
ctgggttcat taggagtctc                                               20

<210> SEQ ID NO 242
<211> LENGTH: 24
<212> TYPE: DNA
<213> ORGANISM: Artificial
<220> FEATURE:
<223> OTHER INFORMATION: Synthetic nucleic acid

<400> SEQUENCE: 242
ttcagagatc ggattgtagg agtc                                          24

<210> SEQ ID NO 243
<211> LENGTH: 20
<212> TYPE: DNA
<213> ORGANISM: Artificial
<220> FEATURE:
<223> OTHER INFORMATION: Synthetic nucleic acid

<400> SEQUENCE: 243
cctgggttca gtaggagtct                                               20

<210> SEQ ID NO 244
<211> LENGTH: 20
<212> TYPE: DNA
<213> ORGANISM: Artificial
<220> FEATURE:
<223> OTHER INFORMATION: Synthetic nucleic acid

<400> SEQUENCE: 244
cctgggttca taggagtctc                                               20

<210> SEQ ID NO 245
<211> LENGTH: 20
<212> TYPE: DNA
<213> ORGANISM: Artificial
<220> FEATURE:
<223> OTHER INFORMATION: Synthetic nucleic acid

<400> SEQUENCE: 245
cctgggttcg taggagtctc                                               20

<210> SEQ ID NO 246
<211> LENGTH: 21

```
<212> TYPE: DNA
<213> ORGANISM: Artificial
<220> FEATURE:
<223> OTHER INFORMATION: Synthetic nucleic acid

<400> SEQUENCE: 246
cctgggttca ggagtctcga c                                         21

<210> SEQ ID NO 247
<211> LENGTH: 21
<212> TYPE: DNA
<213> ORGANISM: Artificial
<220> FEATURE:
<223> OTHER INFORMATION: Synthetic nucleic acid

<400> SEQUENCE: 247
cctgggttca aggagtctcg a                                         21

<210> SEQ ID NO 248
<211> LENGTH: 21
<212> TYPE: DNA
<213> ORGANISM: Artificial
<220> FEATURE:
<223> OTHER INFORMATION: Synthetic nucleic acid

<400> SEQUENCE: 248
cctgggttca tgtaggagtc t                                         21

<210> SEQ ID NO 249
<211> LENGTH: 24
<212> TYPE: DNA
<213> ORGANISM: Artificial
<220> FEATURE:
<223> OTHER INFORMATION: Synthetic nucleic acid

<400> SEQUENCE: 249
cagagatcgg atttgtagga gtct                                      24

<210> SEQ ID NO 250
<211> LENGTH: 24
<212> TYPE: DNA
<213> ORGANISM: Artificial
<220> FEATURE:
<223> OTHER INFORMATION: Synthetic nucleic acid

<400> SEQUENCE: 250
ttcagagatc ggttgtagga gtct                                      24

<210> SEQ ID NO 251
<211> LENGTH: 24
<212> TYPE: DNA
<213> ORGANISM: Artificial
<220> FEATURE:
<223> OTHER INFORMATION: Synthetic nucleic acid

<400> SEQUENCE: 251
tcagagatcg gatttgtagg agtc                                      24

<210> SEQ ID NO 252
<211> LENGTH: 24
<212> TYPE: DNA
<213> ORGANISM: Artificial
<220> FEATURE:
<223> OTHER INFORMATION: Synthetic nucleic acid

<400> SEQUENCE: 252
```

```
cctgggttca tttgtaggag tctc                                            24
```

<210> SEQ ID NO 253
<211> LENGTH: 22
<212> TYPE: DNA
<213> ORGANISM: Artificial
<220> FEATURE:
<223> OTHER INFORMATION: Synthetic nucleic acid

<400> SEQUENCE: 253

```
atcggattcc agtaggagtc tc                                              22
```

<210> SEQ ID NO 254
<211> LENGTH: 22
<212> TYPE: DNA
<213> ORGANISM: Artificial
<220> FEATURE:
<223> OTHER INFORMATION: Synthetic nucleic acid

<400> SEQUENCE: 254

```
agtttcagag agtaggagtc tc                                              22
```

<210> SEQ ID NO 255
<211> LENGTH: 21
<212> TYPE: DNA
<213> ORGANISM: Artificial
<220> FEATURE:
<223> OTHER INFORMATION: Synthetic nucleic acid

<400> SEQUENCE: 255

```
cctgggttca tgagtctcga c                                               21
```

<210> SEQ ID NO 256
<211> LENGTH: 21
<212> TYPE: DNA
<213> ORGANISM: Artificial
<220> FEATURE:
<223> OTHER INFORMATION: Synthetic nucleic acid

<400> SEQUENCE: 256

```
ctgggttcat tgtaggagt c                                                21
```

<210> SEQ ID NO 257
<211> LENGTH: 24
<212> TYPE: DNA
<213> ORGANISM: Artificial
<220> FEATURE:
<223> OTHER INFORMATION: Synthetic nucleic acid

<400> SEQUENCE: 257

```
cagagatcgg attttgtagg agtc                                            24
```

<210> SEQ ID NO 258
<211> LENGTH: 22
<212> TYPE: DNA
<213> ORGANISM: Artificial
<220> FEATURE:
<223> OTHER INFORMATION: Synthetic nucleic acid

<400> SEQUENCE: 258

```
gcacaaacac tgtaggagtc tc                                              22
```

<210> SEQ ID NO 259
<211> LENGTH: 22
<212> TYPE: DNA
<213> ORGANISM: Artificial

```
<220> FEATURE:
<223> OTHER INFORMATION: Synthetic nucleic acid

<400> SEQUENCE: 259
tgcacaaaca cgtaggagtc tc                                              22

<210> SEQ ID NO 260
<211> LENGTH: 22
<212> TYPE: DNA
<213> ORGANISM: Artificial
<220> FEATURE:
<223> OTHER INFORMATION: Synthetic nucleic acid

<400> SEQUENCE: 260
cctgggttca cacaaacact gt                                              22

<210> SEQ ID NO 261
<211> LENGTH: 24
<212> TYPE: DNA
<213> ORGANISM: Artificial
<220> FEATURE:
<223> OTHER INFORMATION: Synthetic nucleic acid

<400> SEQUENCE: 261
cctgggttca tgcacaaaca ctgt                                            24

<210> SEQ ID NO 262
<211> LENGTH: 24
<212> TYPE: DNA
<213> ORGANISM: Artificial
<220> FEATURE:
<223> OTHER INFORMATION: Synthetic nucleic acid

<400> SEQUENCE: 262
cagagatcgg atcacaaaca ctgt                                            24

<210> SEQ ID NO 263
<211> LENGTH: 24
<212> TYPE: DNA
<213> ORGANISM: Artificial
<220> FEATURE:
<223> OTHER INFORMATION: Synthetic nucleic acid

<400> SEQUENCE: 263
tcagagatcg gacacaaaca ctgt                                            24

<210> SEQ ID NO 264
<211> LENGTH: 22
<212> TYPE: DNA
<213> ORGANISM: Artificial
<220> FEATURE:
<223> OTHER INFORMATION: Synthetic nucleic acid

<400> SEQUENCE: 264
ttcagagatc gggagtctcg ac                                              22

<210> SEQ ID NO 265
<211> LENGTH: 20
<212> TYPE: DNA
<213> ORGANISM: Artificial
<220> FEATURE:
<223> OTHER INFORMATION: Synthetic nucleic acid

<400> SEQUENCE: 265
cctgggttca gagtctcgac                                                 20
```

```
<210> SEQ ID NO 266
<211> LENGTH: 22
<212> TYPE: DNA
<213> ORGANISM: Artificial
<220> FEATURE:
<223> OTHER INFORMATION: Synthetic nucleic acid

<400> SEQUENCE: 266
ccagtatacc tgtaggagtc tc                                              22

<210> SEQ ID NO 267
<211> LENGTH: 22
<212> TYPE: DNA
<213> ORGANISM: Artificial
<220> FEATURE:
<223> OTHER INFORMATION: Synthetic nucleic acid

<400> SEQUENCE: 267
ttccagtata cgtaggagtc tc                                              22

<210> SEQ ID NO 268
<211> LENGTH: 24
<212> TYPE: DNA
<213> ORGANISM: Artificial
<220> FEATURE:
<223> OTHER INFORMATION: Synthetic nucleic acid

<400> SEQUENCE: 268
cctgggttca tgtcagagat cgga                                            24

<210> SEQ ID NO 269
<211> LENGTH: 24
<212> TYPE: DNA
<213> ORGANISM: Artificial
<220> FEATURE:
<223> OTHER INFORMATION: Synthetic nucleic acid

<400> SEQUENCE: 269
cctgggttca tgagagatcg gatt                                            24

<210> SEQ ID NO 270
<211> LENGTH: 22
<212> TYPE: DNA
<213> ORGANISM: Artificial
<220> FEATURE:
<223> OTHER INFORMATION: Synthetic nucleic acid

<400> SEQUENCE: 270
tttcagagat cgtaggagtc tc                                              22

<210> SEQ ID NO 271
<211> LENGTH: 22
<212> TYPE: DNA
<213> ORGANISM: Artificial
<220> FEATURE:
<223> OTHER INFORMATION: Synthetic nucleic acid

<400> SEQUENCE: 271
caaacactgt tggagtctcg ac                                              22

<210> SEQ ID NO 272
<211> LENGTH: 22
<212> TYPE: DNA
<213> ORGANISM: Artificial
<220> FEATURE:
<223> OTHER INFORMATION: Synthetic nucleic acid
```

```
<400> SEQUENCE: 272
acaaacactg tggagtctcg ac                                              22

<210> SEQ ID NO 273
<211> LENGTH: 19
<212> TYPE: DNA
<213> ORGANISM: Artificial
<220> FEATURE:
<223> OTHER INFORMATION: Synthetic nucleic acid

<400> SEQUENCE: 273
cctgggttct aggagtctc                                                  19

<210> SEQ ID NO 274
<211> LENGTH: 19
<212> TYPE: DNA
<213> ORGANISM: Artificial
<220> FEATURE:
<223> OTHER INFORMATION: Synthetic nucleic acid

<400> SEQUENCE: 274
cctgggttcg taggagtct                                                  19

<210> SEQ ID NO 275
<211> LENGTH: 18
<212> TYPE: DNA
<213> ORGANISM: Artificial
<220> FEATURE:
<223> OTHER INFORMATION: Synthetic nucleic acid

<400> SEQUENCE: 275
cctgggttca ggagtctc                                                   18

<210> SEQ ID NO 276
<211> LENGTH: 18
<212> TYPE: DNA
<213> ORGANISM: Artificial
<220> FEATURE:
<223> OTHER INFORMATION: Synthetic nucleic acid

<400> SEQUENCE: 276
cctgggttct aggagtct                                                   18

<210> SEQ ID NO 277
<211> LENGTH: 24
<212> TYPE: DNA
<213> ORGANISM: Artificial
<220> FEATURE:
<223> OTHER INFORMATION: Synthetic nucleic acid

<400> SEQUENCE: 277
ttggattcag gttgtaggag tctc                                            24

<210> SEQ ID NO 278
<211> LENGTH: 24
<212> TYPE: DNA
<213> ORGANISM: Artificial
<220> FEATURE:
<223> OTHER INFORMATION: Synthetic nucleic acid

<400> SEQUENCE: 278
aagttggatt catgtaggag tctc                                            24

<210> SEQ ID NO 279
```

<211> LENGTH: 24
<212> TYPE: DNA
<213> ORGANISM: Artificial
<220> FEATURE:
<223> OTHER INFORMATION: Synthetic nucleic acid

<400> SEQUENCE: 279
tcaggatttg catgtaggag tctc                                          24

<210> SEQ ID NO 280
<211> LENGTH: 24
<212> TYPE: DNA
<213> ORGANISM: Artificial
<220> FEATURE:
<223> OTHER INFORMATION: Synthetic nucleic acid

<400> SEQUENCE: 280
tctcaggatt tgtgtaggag tctc                                          24

<210> SEQ ID NO 281
<211> LENGTH: 22
<212> TYPE: DNA
<213> ORGANISM: Artificial
<220> FEATURE:
<223> OTHER INFORMATION: Synthetic nucleic acid

<400> SEQUENCE: 281
agatcggatt cgtaggagtc tc                                            22

<210> SEQ ID NO 282
<211> LENGTH: 22
<212> TYPE: DNA
<213> ORGANISM: Artificial
<220> FEATURE:
<223> OTHER INFORMATION: Synthetic nucleic acid

<400> SEQUENCE: 282
cagagatcgg agtaggagtc tc                                            22

<210> SEQ ID NO 283
<211> LENGTH: 22
<212> TYPE: DNA
<213> ORGANISM: Artificial
<220> FEATURE:
<223> OTHER INFORMATION: Synthetic nucleic acid

<400> SEQUENCE: 283
tcagagatcg ggtaggagtc tc                                            22

<210> SEQ ID NO 284
<211> LENGTH: 24
<212> TYPE: DNA
<213> ORGANISM: Artificial
<220> FEATURE:
<223> OTHER INFORMATION: Synthetic nucleic acid

<400> SEQUENCE: 284
cctgggttca tgccagtata cctt                                          24

<210> SEQ ID NO 285
<211> LENGTH: 24
<212> TYPE: DNA
<213> ORGANISM: Artificial
<220> FEATURE:
<223> OTHER INFORMATION: Synthetic nucleic acid

<400> SEQUENCE: 285

```
cctgggttca tgttccagta tacc                                          24
```

<210> SEQ ID NO 286
<211> LENGTH: 24
<212> TYPE: DNA
<213> ORGANISM: Artificial
<220> FEATURE:
<223> OTHER INFORMATION: Synthetic nucleic acid

<400> SEQUENCE: 286

```
tttgagccaa ttcctgggtt catg                                          24
```

<210> SEQ ID NO 287
<211> LENGTH: 24
<212> TYPE: DNA
<213> ORGANISM: Artificial
<220> FEATURE:
<223> OTHER INFORMATION: Synthetic nucleic acid

<400> SEQUENCE: 287

```
tgtttgagcc aacctgggtt catg                                          24
```

<210> SEQ ID NO 288
<211> LENGTH: 24
<212> TYPE: DNA
<213> ORGANISM: Artificial
<220> FEATURE:
<223> OTHER INFORMATION: Synthetic nucleic acid

<400> SEQUENCE: 288

```
tcctgggaag gtcctgggtt catg                                          24
```

<210> SEQ ID NO 289
<211> LENGTH: 24
<212> TYPE: DNA
<213> ORGANISM: Artificial
<220> FEATURE:
<223> OTHER INFORMATION: Synthetic nucleic acid

<400> SEQUENCE: 289

```
tggtcctggg aacctgggtt catg                                          24
```

<210> SEQ ID NO 290
<211> LENGTH: 21
<212> TYPE: DNA
<213> ORGANISM: Artificial
<220> FEATURE:
<223> OTHER INFORMATION: Synthetic nucleic acid

<400> SEQUENCE: 290

```
cctgggctca gtaggagtct t                                             21
```

<210> SEQ ID NO 291
<211> LENGTH: 25
<212> TYPE: DNA
<213> ORGANISM: Artificial
<220> FEATURE:
<223> OTHER INFORMATION: Synthetic nucleic acid

<400> SEQUENCE: 291

```
cctgggctca tgttgtagga gtctt                                         25
```

<210> SEQ ID NO 292
<211> LENGTH: 26
<212> TYPE: DNA

```
<213> ORGANISM: Artificial
<220> FEATURE:
<223> OTHER INFORMATION: Synthetic nucleic acid

<400> SEQUENCE: 292
gtaggagtct tgcattagaa agtcag                                         26

<210> SEQ ID NO 293
<211> LENGTH: 24
<212> TYPE: DNA
<213> ORGANISM: Artificial
<220> FEATURE:
<223> OTHER INFORMATION: Synthetic nucleic acid

<400> SEQUENCE: 293
cctgggctca tttgtaggag tctt                                           24

<210> SEQ ID NO 294
<211> LENGTH: 24
<212> TYPE: DNA
<213> ORGANISM: Artificial
<220> FEATURE:
<223> OTHER INFORMATION: Synthetic nucleic acid

<400> SEQUENCE: 294
cctgggctca tgaggagtct tgac                                           24

<210> SEQ ID NO 295
<211> LENGTH: 22
<212> TYPE: DNA
<213> ORGANISM: Artificial
<220> FEATURE:
<223> OTHER INFORMATION: Synthetic nucleic acid

<400> SEQUENCE: 295
cacaaacact ggtaggagtc tt                                             22

<210> SEQ ID NO 296
<211> LENGTH: 26
<212> TYPE: DNA
<213> ORGANISM: Artificial
<220> FEATURE:
<223> OTHER INFORMATION: Synthetic nucleic acid

<400> SEQUENCE: 296
ctggtcctgg gaacttgtac cgtctt                                         26

<210> SEQ ID NO 297
<211> LENGTH: 23
<212> TYPE: DNA
<213> ORGANISM: Artificial
<220> FEATURE:
<223> OTHER INFORMATION: Synthetic nucleic acid

<400> SEQUENCE: 297
cctgggctca ttgtaggagt ctt                                            23

<210> SEQ ID NO 298
<211> LENGTH: 22
<212> TYPE: DNA
<213> ORGANISM: Artificial
<220> FEATURE:
<223> OTHER INFORMATION: Synthetic nucleic acid

<400> SEQUENCE: 298
cctgggctca tgtaggagtc tt                                             22
```

<210> SEQ ID NO 299
<211> LENGTH: 20
<212> TYPE: DNA
<213> ORGANISM: Artificial
<220> FEATURE:
<223> OTHER INFORMATION: Synthetic nucleic acid

<400> SEQUENCE: 299
cctgggctcg taggagtctt                                              20

<210> SEQ ID NO 300
<211> LENGTH: 22
<212> TYPE: DNA
<213> ORGANISM: Artificial
<220> FEATURE:
<223> OTHER INFORMATION: Synthetic nucleic acid

<400> SEQUENCE: 300
cctgggctca ttgtaggagt ct                                           22

<210> SEQ ID NO 301
<211> LENGTH: 24
<212> TYPE: DNA
<213> ORGANISM: Artificial
<220> FEATURE:
<223> OTHER INFORMATION: Synthetic nucleic acid

<400> SEQUENCE: 301
tgcctgggct catgtaggag tctt                                         24

<210> SEQ ID NO 302
<211> LENGTH: 24
<212> TYPE: DNA
<213> ORGANISM: Artificial
<220> FEATURE:
<223> OTHER INFORMATION: Synthetic nucleic acid

<400> SEQUENCE: 302
gctgtttgag cctgtaggag tctt                                         24

<210> SEQ ID NO 303
<211> LENGTH: 24
<212> TYPE: DNA
<213> ORGANISM: Artificial
<220> FEATURE:
<223> OTHER INFORMATION: Synthetic nucleic acid

<400> SEQUENCE: 303
cctgggctca tgtgtaggag tctt                                         24

<210> SEQ ID NO 304
<211> LENGTH: 24
<212> TYPE: DNA
<213> ORGANISM: Artificial
<220> FEATURE:
<223> OTHER INFORMATION: Synthetic nucleic acid

<400> SEQUENCE: 304
ctttcatggg tttgtaggag tctt                                         24

<210> SEQ ID NO 305
<211> LENGTH: 25
<212> TYPE: DNA
<213> ORGANISM: Artificial
<220> FEATURE:

<223> OTHER INFORMATION: Synthetic nucleic acid

<400> SEQUENCE: 305
cctgggctca tgtttgtagg agtct                                    25

<210> SEQ ID NO 306
<211> LENGTH: 25
<212> TYPE: DNA
<213> ORGANISM: Artificial
<220> FEATURE:
<223> OTHER INFORMATION: Synthetic nucleic acid

<400> SEQUENCE: 306
gcctgggctc atgtgtagga gtctt                                    25

<210> SEQ ID NO 307
<211> LENGTH: 25
<212> TYPE: DNA
<213> ORGANISM: Artificial
<220> FEATURE:
<223> OTHER INFORMATION: Synthetic nucleic acid

<400> SEQUENCE: 307
ctgggctcat gtctgtagga gtctt                                    25

<210> SEQ ID NO 308
<211> LENGTH: 25
<212> TYPE: DNA
<213> ORGANISM: Artificial
<220> FEATURE:
<223> OTHER INFORMATION: Synthetic nucleic acid

<400> SEQUENCE: 308
cctgggctca tgtgtaggag tcttg                                    25

<210> SEQ ID NO 309
<211> LENGTH: 23
<212> TYPE: DNA
<213> ORGANISM: Artificial
<220> FEATURE:
<223> OTHER INFORMATION: Synthetic nucleic acid

<400> SEQUENCE: 309
tccagtatac cttgtaggag tct                                      23

<210> SEQ ID NO 310
<211> LENGTH: 24
<212> TYPE: DNA
<213> ORGANISM: Artificial
<220> FEATURE:
<223> OTHER INFORMATION: Synthetic nucleic acid

<400> SEQUENCE: 310
catgggtttg attgtaggag tctt                                     24

<210> SEQ ID NO 311
<211> LENGTH: 24
<212> TYPE: DNA
<213> ORGANISM: Artificial
<220> FEATURE:
<223> OTHER INFORMATION: Synthetic nucleic acid

<400> SEQUENCE: 311
gattcaggct gttgtaggag tctt                                     24

```
<210> SEQ ID NO 312
<211> LENGTH: 26
<212> TYPE: DNA
<213> ORGANISM: Artificial
<220> FEATURE:
<223> OTHER INFORMATION: Synthetic nucleic acid

<400> SEQUENCE: 312
ttctcctggt cctaccgtct ttcatg                                          26

<210> SEQ ID NO 313
<211> LENGTH: 26
<212> TYPE: DNA
<213> ORGANISM: Artificial
<220> FEATURE:
<223> OTHER INFORMATION: Synthetic nucleic acid

<400> SEQUENCE: 313
ttctcctggt cctatacctt gtaccg                                          26

<210> SEQ ID NO 314
<211> LENGTH: 25
<212> TYPE: DNA
<213> ORGANISM: Artificial
<220> FEATURE:
<223> OTHER INFORMATION: Synthetic nucleic acid

<400> SEQUENCE: 314
tgtaggagtc ttatatccac agttg                                           25

<210> SEQ ID NO 315
<211> LENGTH: 24
<212> TYPE: DNA
<213> ORGANISM: Artificial
<220> FEATURE:
<223> OTHER INFORMATION: Synthetic nucleic acid

<400> SEQUENCE: 315
cagagatcgg atgttgtagg agtc                                            24

<210> SEQ ID NO 316
<211> LENGTH: 24
<212> TYPE: DNA
<213> ORGANISM: Artificial
<220> FEATURE:
<223> OTHER INFORMATION: Synthetic nucleic acid

<400> SEQUENCE: 316
agagatcgga ttttgtagga gtct                                            24

<210> SEQ ID NO 317
<211> LENGTH: 24
<212> TYPE: DNA
<213> ORGANISM: Artificial
<220> FEATURE:
<223> OTHER INFORMATION: Synthetic nucleic acid

<400> SEQUENCE: 317
tttcagagat cgggtaggag tctt                                            24

<210> SEQ ID NO 318
<211> LENGTH: 24
<212> TYPE: DNA
<213> ORGANISM: Artificial
<220> FEATURE:
<223> OTHER INFORMATION: Synthetic nucleic acid
```

<400> SEQUENCE: 318
tttcagagat cggtgtagga gtct                                          24

<210> SEQ ID NO 319
<211> LENGTH: 24
<212> TYPE: DNA
<213> ORGANISM: Artificial
<220> FEATURE:
<223> OTHER INFORMATION: Synthetic nucleic acid

<400> SEQUENCE: 319
tttcagagat cgggttgtag gagt                                          24

<210> SEQ ID NO 320
<211> LENGTH: 24
<212> TYPE: DNA
<213> ORGANISM: Artificial
<220> FEATURE:
<223> OTHER INFORMATION: Synthetic nucleic acid

<400> SEQUENCE: 320
agagatcgga ttcttgtagg agtc                                          24

<210> SEQ ID NO 321
<211> LENGTH: 24
<212> TYPE: DNA
<213> ORGANISM: Artificial
<220> FEATURE:
<223> OTHER INFORMATION: Synthetic nucleic acid

<400> SEQUENCE: 321
attccagtat actgtaggag tctt                                          24

<210> SEQ ID NO 322
<211> LENGTH: 24
<212> TYPE: DNA
<213> ORGANISM: Artificial
<220> FEATURE:
<223> OTHER INFORMATION: Synthetic nucleic acid

<400> SEQUENCE: 322
tccagtatac cttgtaggag tctt                                          24

<210> SEQ ID NO 323
<211> LENGTH: 374
<212> TYPE: DNA
<213> ORGANISM: Homo sapiens

<400> SEQUENCE: 323
ctgattttct aatgcaagtg gatggaaaac ccaaatgttg cttctttaaa tttagctcta    60
aaatacaata caataaagta gtaaaggccc aactatggat atatttgaga cccgtcgaga   120
ctcctacaac agtgtttgtg caaatcctga gactcatcaa acctatgaaa gacggtacaa   180
ggtatactgg aatccgatct ctgaaacttg acatgaaccc aggcactggt atttggcaga   240
gcattgatgt gaagacagtg ttgcaaaatt ggctcaaaca acctgaatcc aacttaggca   300
ttgaaataaa agctttagat gagaatggtc atgatcttgc tgtaaccttc ccaggaccag   360
gagaagatgg gctg                                                    374

<210> SEQ ID NO 324
<211> LENGTH: 374
<212> TYPE: DNA
<213> ORGANISM: Mus musculus

<400> SEQUENCE: 324

| ctgactttct aatgcaagcg gatggcaagc ccaaatgttg cttttttaaa tttagctcta | 60 |
| aaatacagta caacaaagta gtaaaagccc aactgtggat atatctcaga cccgtcaaga | 120 |
| ctcctacaac agtgtttgtg caaatcctga gactcatcaa acccatgaaa gacggtacaa | 180 |
| ggtatactgg aatccgatct ctgaaacttg acatgagccc aggcactggt atttggcaga | 240 |
| gtattgatgt gaagacagtg ttgcaaaatt ggctcaaaca gcctgaatcc aacttaggca | 300 |
| ttgaaatcaa agctttggat gagaatggcc atgatcttgc tgtaaccttc ccaggaccag | 360 |
| gagaagatgg gctg | 374 |

<210> SEQ ID NO 325
<211> LENGTH: 384
<212> TYPE: DNA
<213> ORGANISM: Homo sapiens

<400> SEQUENCE: 325

| tcatttatag ctgattttct aatgcaagtg gatggaaaac ccaaatgttg cttcttttaaa | 60 |
| tttagctcta aaatacaata caataaagta gtaaaggccc aactatggat atatttgaga | 120 |
| cccgtcgaga ctcctacaac agtgtttgtg caaatcctga gactcatcaa acctatgaaa | 180 |
| gacggtacaa ggtatactgg aatccgatct ctgaaacttg acatgaaccc aggcactggt | 240 |
| atttggcaga gcattgatgt gaagacagtg ttgcaaaatt ggctcaaaca acctgaatcc | 300 |
| aacttaggca ttgaaataaa agctttagat gagaatggtc atgatcttgc tgtaaccttc | 360 |
| ccaggaccag gagaagatgg gctg | 384 |

<210> SEQ ID NO 326
<211> LENGTH: 384
<212> TYPE: DNA
<213> ORGANISM: Mus musculus

<400> SEQUENCE: 326

| tcctttgtag ctgactttct aatgcaagcg gatggcaagc ccaaatgttg cttttttaaa | 60 |
| tttagctcta aaatacagta caacaaagta gtaaaagccc aactgtggat atatctcaga | 120 |
| cccgtcaaga ctcctacaac agtgtttgtg caaatcctga gactcatcaa acccatgaaa | 180 |
| gacggtacaa ggtatactgg aatccgatct ctgaaacttg acatgagccc aggcactggt | 240 |
| atttggcaga gtattgatgt gaagacagtg ttgcaaaatt ggctcaaaca gcctgaatcc | 300 |
| aacttaggca ttgaaatcaa agctttggat gagaatggcc atgatcttgc tgtaaccttc | 360 |
| ccaggaccag gagaagatgg gctg | 384 |

<210> SEQ ID NO 327
<211> LENGTH: 55
<212> TYPE: DNA
<213> ORGANISM: Homo sapiens

<400> SEQUENCE: 327

| tcatttatag ctgattttct aatgcaagtg gatggaaaac ccaaatgttg cttct | 55 |

<210> SEQ ID NO 328
<211> LENGTH: 55
<212> TYPE: DNA
<213> ORGANISM: Homo sapiens

<400> SEQUENCE: 328
aactatggat atatttgaga cccgtcgaga ctcctacaac agtgtttgtg caaat                55

<210> SEQ ID NO 329
<211> LENGTH: 35
<212> TYPE: DNA
<213> ORGANISM: Homo sapiens

<400> SEQUENCE: 329
cctgagactc atcaaaccta tgaaagacgg tacaa                                     35

<210> SEQ ID NO 330
<211> LENGTH: 44
<212> TYPE: DNA
<213> ORGANISM: Homo sapiens

<400> SEQUENCE: 330
atgatcttgc tgtaaccttc ccaggaccag gagaagatgg gctg                           44

<210> SEQ ID NO 331
<211> LENGTH: 41
<212> TYPE: DNA
<213> ORGANISM: Mus musculus

<400> SEQUENCE: 331
tcctttgtag ctgactttct aatgcaagcg gatggcaagc c                              41

<210> SEQ ID NO 332
<211> LENGTH: 52
<212> TYPE: DNA
<213> ORGANISM: Mus musculus

<400> SEQUENCE: 332
cccgtcaaga ctcctacaac agtgtttgtg caaatcctga gactcatcaa ac                  52

<210> SEQ ID NO 333
<211> LENGTH: 30
<212> TYPE: DNA
<213> ORGANISM: Mus musculus

<400> SEQUENCE: 333
tgaaagacgg tacaaggtat actggaatcc                                           30

<210> SEQ ID NO 334
<211> LENGTH: 44
<212> TYPE: DNA
<213> ORGANISM: Mus musculus

<400> SEQUENCE: 334
atgatcttgc tgtaaccttc ccaggaccag gagaagatgg gctg                           44

<210> SEQ ID NO 335
<211> LENGTH: 41
<212> TYPE: DNA
<213> ORGANISM: Homo sapiens

<400> SEQUENCE: 335
tcatttatag ctgattttct aatgcaagtg gatggaaaac c                              41

<210> SEQ ID NO 336
<211> LENGTH: 30
<212> TYPE: DNA
<213> ORGANISM: Homo sapiens

<400> SEQUENCE: 336

```
cccgtcgaga ctcctacaac agtgtttgtg                                       30

<210> SEQ ID NO 337
<211> LENGTH: 55
<212> TYPE: DNA
<213> ORGANISM: Homo sapiens

<400> SEQUENCE: 337
tcatttatag ctgattttct aatgcaagtg gatggaaaac ccaaatgttg cttct          55

<210> SEQ ID NO 338
<211> LENGTH: 45
<212> TYPE: DNA
<213> ORGANISM: Homo sapiens

<400> SEQUENCE: 338
aactatggat atatttgaga cccgtcgaga ctcctacaac agtgt                     45

<210> SEQ ID NO 339
<211> LENGTH: 35
<212> TYPE: DNA
<213> ORGANISM: Homo sapiens

<400> SEQUENCE: 339
ctcctacaac agtgtttgtg caaatcctga gactc                                35

<210> SEQ ID NO 340
<211> LENGTH: 45
<212> TYPE: DNA
<213> ORGANISM: Homo sapiens

<400> SEQUENCE: 340
tgaaagacgg tacaaggtat actggaatcc gatctctgaa acttg                     45

<210> SEQ ID NO 341
<211> LENGTH: 30
<212> TYPE: DNA
<213> ORGANISM: Homo sapiens

<400> SEQUENCE: 341
aaacttgaca tgaacccagg cactggtatt                                      30

<210> SEQ ID NO 342
<211> LENGTH: 49
<212> TYPE: DNA
<213> ORGANISM: Homo sapiens

<400> SEQUENCE: 342
tggtcatgat cttgctgtaa ccttcccagg accaggagaa gatgggctg                 49

<210> SEQ ID NO 343
<211> LENGTH: 75
<212> TYPE: DNA
<213> ORGANISM: Mus musculus

<400> SEQUENCE: 343
tcctttgtag ctgactttct aatgcaagcg gatggcaagc ccaaatgttg ctttttaaa     60 tttagctcta aaata                                                      75

<210> SEQ ID NO 344
<211> LENGTH: 45
<212> TYPE: DNA
```

<213> ORGANISM: Mus musculus

<400> SEQUENCE: 344
aactgtggat atatctcaga cccgtcaaga ctcctacaac agtgt    45

<210> SEQ ID NO 345
<211> LENGTH: 35
<212> TYPE: DNA
<213> ORGANISM: Mus musculus

<400> SEQUENCE: 345
ctcctacaac agtgtttgtg caaatcctga gactc    35

<210> SEQ ID NO 346
<211> LENGTH: 60
<212> TYPE: DNA
<213> ORGANISM: Mus musculus

<400> SEQUENCE: 346
gactcatcaa acccatgaaa gacggtacaa ggtatactgg aatccgatct ctgaaacttg    60

<210> SEQ ID NO 347
<211> LENGTH: 38
<212> TYPE: DNA
<213> ORGANISM: Mus musculus

<400> SEQUENCE: 347
gatctctgaa acttgacatg agcccaggca ctggtatt    38

<210> SEQ ID NO 348
<211> LENGTH: 49
<212> TYPE: DNA
<213> ORGANISM: Mus musculus

<400> SEQUENCE: 348
tggccatgat cttgctgtaa ccttcccagg accaggagaa gatgggctg    49

<210> SEQ ID NO 349
<211> LENGTH: 29
<212> TYPE: DNA
<213> ORGANISM: Homo sapiens

<400> SEQUENCE: 349
atagctgatt ttctaatgca agtggatgg    29

<210> SEQ ID NO 350
<211> LENGTH: 20
<212> TYPE: DNA
<213> ORGANISM: Homo sapiens

<400> SEQUENCE: 350
ccgtcgagac tcctacaaca    20

<210> SEQ ID NO 351
<211> LENGTH: 15
<212> TYPE: DNA
<213> ORGANISM: Homo sapiens

<400> SEQUENCE: 351
aacagtgttt gtgca    15

<210> SEQ ID NO 352
<211> LENGTH: 38

<212> TYPE: DNA
<213> ORGANISM: Homo sapiens

<400> SEQUENCE: 352
aagacggtac aaggtatact ggaatccgat ctctgaaa                      38

<210> SEQ ID NO 353
<211> LENGTH: 20
<212> TYPE: DNA
<213> ORGANISM: Homo sapiens

<400> SEQUENCE: 353
tgacatgaac ccaggcactg                                          20

<210> SEQ ID NO 354
<211> LENGTH: 35
<212> TYPE: DNA
<213> ORGANISM: Homo sapiens

<400> SEQUENCE: 354
atgatcttgc tgtaaccttc ccaggaccag gagaa                         35

<210> SEQ ID NO 355
<211> LENGTH: 18
<212> TYPE: DNA
<213> ORGANISM: Mus musculus

<400> SEQUENCE: 355
ctgactttct aatgcaag                                            18

<210> SEQ ID NO 356
<211> LENGTH: 18
<212> TYPE: DNA
<213> ORGANISM: Mus musculus

<400> SEQUENCE: 356
gtcaagactc ctacaaca                                            18

<210> SEQ ID NO 357
<211> LENGTH: 11
<212> TYPE: DNA
<213> ORGANISM: Mus musculus

<400> SEQUENCE: 357
cagtgtttgt g                                                   11

<210> SEQ ID NO 358
<211> LENGTH: 47
<212> TYPE: DNA
<213> ORGANISM: Mus musculus

<400> SEQUENCE: 358
aacccatgaa agacggtaca aggtatactg gaatccgatc tctgaaa            47

<210> SEQ ID NO 359
<211> LENGTH: 15
<212> TYPE: DNA
<213> ORGANISM: Mus musculus

<400> SEQUENCE: 359
acatgagccc aggca                                               15

<210> SEQ ID NO 360

```
<211> LENGTH: 20
<212> TYPE: DNA
<213> ORGANISM: Artificial
<220> FEATURE:
<223> OTHER INFORMATION: Synthetic nucleic acid

<400> SEQUENCE: 360
ttcgtctgga aacagctcct                                          20

<210> SEQ ID NO 361
<211> LENGTH: 20
<212> TYPE: DNA
<213> ORGANISM: Artificial
<220> FEATURE:
<223> OTHER INFORMATION: Synthetic nucleic acid

<400> SEQUENCE: 361
agagggtaac gacagcatcg                                          20

<210> SEQ ID NO 362
<211> LENGTH: 35
<212> TYPE: DNA
<213> ORGANISM: Homo sapiens

<400> SEQUENCE: 362
cctgagactc atcaaaccta tgaaagacgg tacaa                         35

<210> SEQ ID NO 363
<211> LENGTH: 44
<212> TYPE: DNA
<213> ORGANISM: Homo sapiens

<400> SEQUENCE: 363
atgatcttgc tgtaaccttc ccaggaccag gagaagatgg gctg               44

<210> SEQ ID NO 364
<211> LENGTH: 30
<212> TYPE: DNA
<213> ORGANISM: Mus musculus

<400> SEQUENCE: 364
aaattggctc aaacagcctg aatccaactt                               30

<210> SEQ ID NO 365
<211> LENGTH: 12
<212> TYPE: DNA
<213> ORGANISM: Mus musculus

<400> SEQUENCE: 365
ggctcaaaca gc                                                  12

<210> SEQ ID NO 366
<211> LENGTH: 25
<212> TYPE: DNA
<213> ORGANISM: Mus musculus

<400> SEQUENCE: 366
tgtaaccttc ccaggaccag gagaa                                    25

<210> SEQ ID NO 367
<211> LENGTH: 26
<212> TYPE: DNA
<213> ORGANISM: Artificial
<220> FEATURE:
<223> OTHER INFORMATION: Synthetic nucleic acid
```

```
<400> SEQUENCE: 367
ttcagagatc ggattgtagg agtctt                                          26

<210> SEQ ID NO 368
<211> LENGTH: 26
<212> TYPE: DNA
<213> ORGANISM: Artificial
<220> FEATURE:
<223> OTHER INFORMATION: Synthetic nucleic acid

<400> SEQUENCE: 368
ccatcttctc ctgcttgtac cgtctt                                          26

<210> SEQ ID NO 369
<211> LENGTH: 25
<212> TYPE: DNA
<213> ORGANISM: Artificial
<220> FEATURE:
<223> OTHER INFORMATION: Synthetic nucleic acid

<400> SEQUENCE: 369
tgtaggagtc ttgatatatc cacag                                           25

<210> SEQ ID NO 370
<211> LENGTH: 24
<212> TYPE: DNA
<213> ORGANISM: Artificial
<220> FEATURE:
<223> OTHER INFORMATION: Synthetic nucleic acid

<400> SEQUENCE: 370
cagagatcgg attgtaggag tctt                                            24

<210> SEQ ID NO 371
<211> LENGTH: 20
<212> TYPE: DNA
<213> ORGANISM: Artificial
<220> FEATURE:
<223> OTHER INFORMATION: Synthetic nucleic acid

<400> SEQUENCE: 371
ttcagagatc taggagtctc                                                 20

<210> SEQ ID NO 372
<211> LENGTH: 20
<212> TYPE: DNA
<213> ORGANISM: Artificial
<220> FEATURE:
<223> OTHER INFORMATION: Synthetic nucleic acid

<400> SEQUENCE: 372
tcagagatcg taggagtctc                                                 20

<210> SEQ ID NO 373
<211> LENGTH: 20
<212> TYPE: DNA
<213> ORGANISM: Artificial
<220> FEATURE:
<223> OTHER INFORMATION: Synthetic nucleic acid

<400> SEQUENCE: 373
cagagatcgg taggagtctc                                                 20
```

```
<210> SEQ ID NO 374
<211> LENGTH: 22
<212> TYPE: DNA
<213> ORGANISM: Artificial
<220> FEATURE:
<223> OTHER INFORMATION: Synthetic nucleic acid

<400> SEQUENCE: 374
tttcagagat ctgtaggagt ct                                             22

<210> SEQ ID NO 375
<211> LENGTH: 22
<212> TYPE: DNA
<213> ORGANISM: Artificial
<220> FEATURE:
<223> OTHER INFORMATION: Synthetic nucleic acid

<400> SEQUENCE: 375
ttcagagatc gtgtaggagt ct                                             22

<210> SEQ ID NO 376
<211> LENGTH: 22
<212> TYPE: DNA
<213> ORGANISM: Artificial
<220> FEATURE:
<223> OTHER INFORMATION: Synthetic nucleic acid

<400> SEQUENCE: 376
tttcagagat cggagtctcg ac                                             22

<210> SEQ ID NO 377
<211> LENGTH: 22
<212> TYPE: DNA
<213> ORGANISM: Artificial
<220> FEATURE:
<223> OTHER INFORMATION: Synthetic nucleic acid

<400> SEQUENCE: 377
tcagagatcg tgtaggagtc tc                                             22

<210> SEQ ID NO 378
<211> LENGTH: 20
<212> TYPE: DNA
<213> ORGANISM: Artificial
<220> FEATURE:
<223> OTHER INFORMATION: Synthetic nucleic acid

<400> SEQUENCE: 378
tgacagcagt gatggctctt                                                20

<210> SEQ ID NO 379
<211> LENGTH: 20
<212> TYPE: DNA
<213> ORGANISM: Artificial
<220> FEATURE:
<223> OTHER INFORMATION: Synthetic nucleic acid

<400> SEQUENCE: 379
ccaaaggctt caaaatcgac                                                20
```